（12）United States Patent
Hartley et al.

(10) Patent No.: US 12,171,622 B2
(45) Date of Patent: Dec. 24, 2024

(54) HEAT EXCHANGE AND TEMPERATURE SENSING DEVICE AND METHOD OF USE

(71) Applicant: Boston Scientific Medical Device Limited, Ballybrit (IE)

(72) Inventors: Amanda Hartley, Caledon (CA); Gareth Davies, Toronto (CA); Amanda Centazzo-Colella, Toronto (CA); Noah Yang, Ottawa (CA); Hamed Avari, Toronto (CA); Yasir Al-Saffar, Oakville (CA); Kishan Shah, Etobicoke (CA); Andrew Herbert-Copley, Toronto (CA); Ramunas Wierzbicki, Toronto (CA); Dmitry Gerber, Toronto (CA)

(73) Assignee: Boston Scientific Medical Device Limited, Galway (IE)

( * ) Notice: Subject to any disclaimer, the term of this patent is extended or adjusted under 35 U.S.C. 154(b) by 956 days.

(21) Appl. No.: 16/637,315

(22) PCT Filed: Aug. 10, 2018

(86) PCT No.: PCT/IB2018/056059
§ 371 (c)(1),
(2) Date: Feb. 7, 2020

(87) PCT Pub. No.: WO2019/030733
PCT Pub. Date: Feb. 14, 2019

(65) Prior Publication Data
US 2020/0253682 A1    Aug. 13, 2020

Related U.S. Application Data

(60) Provisional application No. 62/543,635, filed on Aug. 10, 2017.

(51) Int. Cl.
*A61B 90/00* (2016.01)
*A61B 5/00* (2006.01)
(Continued)

(52) U.S. Cl.
CPC .............. *A61B 90/04* (2016.02); *A61B 5/01* (2013.01); *A61B 5/6853* (2013.01); *A61B 18/02* (2013.01);
(Continued)

(58) Field of Classification Search
CPC ............ A61B 18/02; A61B 2018/0022; A61B 2018/00839; A61B 90/04;
(Continued)

(56) References Cited

U.S. PATENT DOCUMENTS

| 175,254 | A | 3/1876 | Oberly |
| 827,626 | A | 7/1906 | Gillet |

(Continued)

FOREIGN PATENT DOCUMENTS

| EP | 2952162 A1 | 12/2015 |
| WO | 2006/055286 A2 | 5/2006 |

(Continued)

OTHER PUBLICATIONS

International Search Report and Written Opinion received for PCT Patent Application No. PCT/IB2018/056059, mailed on Mar. 21, 2019, 31 pages.

(Continued)

*Primary Examiner* — Eun Hwa Kim
(74) *Attorney, Agent, or Firm* — Nelson Mullins Riley & Scarborough LLP

(57) ABSTRACT

A method and apparatus are disclosed for regulating a temperature of an esophagus when heat or cold is delivered to a left atrium, the method including altering a heat exchange device from an insertable configuration to a heat exchanging configuration which conforms and corresponds with a cross-section of an inside of the esophagus such that the esophagus is maintained in its natural shape and location. In some embodiments the heat exchange device has a (Continued)

heating/cooling balloon which is inflated to be in the heat exchanging configuration. Some alternative embodiments includes altering the configuration of the balloon to conform to or correspond with the cross section of an esophagus by means other than inflation.

18 Claims, 45 Drawing Sheets

(51) Int. Cl.
*A61B 5/01* (2006.01)
*A61B 18/02* (2006.01)
*A61B 18/04* (2006.01)
*A61F 7/00* (2006.01)
*A61F 7/12* (2006.01)
*A61B 5/287* (2021.01)
*A61B 17/00* (2006.01)
*A61B 18/00* (2006.01)
*A61F 7/10* (2006.01)
*A61M 25/10* (2013.01)
*A61N 1/05* (2006.01)
*A61N 1/362* (2006.01)

(52) U.S. Cl.
CPC ............ *A61B 18/04* (2013.01); *A61F 7/0085* (2013.01); *A61F 7/12* (2013.01); *A61F 7/123* (2013.01); *A61B 5/287* (2021.01); *A61B 2017/00557* (2013.01); *A61B 2018/00023* (2013.01); *A61B 2018/00035* (2013.01); *A61B 2018/0022* (2013.01); *A61B 2018/00357* (2013.01); *A61B 2018/00488* (2013.01); *A61B 2018/00577* (2013.01); *A61B 2018/00791* (2013.01); *A61B 2018/00797* (2013.01); *A61B 2018/00839* (2013.01); *A61B 2018/0091* (2013.01); *A61B 2018/0212* (2013.01); *A61B 2090/0418* (2016.02); *A61B 2090/0463* (2016.02); *A61B 2090/061* (2016.02); *A61B 2090/374* (2016.02); *A61B 2090/3762* (2016.02); *A61B 2090/3966* (2016.02); *A61B 2090/3983* (2016.02); *A61F 2007/0054* (2013.01); *A61F 2007/0056* (2013.01); *A61F 2007/0075* (2013.01); *A61F 2007/0091* (2013.01); *A61F 2007/0096* (2013.01); *A61F 2007/101* (2013.01); *A61F 2007/126* (2013.01); *A61M 25/1002* (2013.01); *A61M 2025/1013* (2013.01); *A61M 2025/1043* (2013.01); *A61M 2025/1084* (2013.01); *A61M 2210/105* (2013.01); *A61N 1/0517* (2013.01); *A61N 1/362* (2013.01)

(58) Field of Classification Search
CPC ......... A61B 2017/00557; A61F 7/0085; A61F 7/12; A61F 7/123
See application file for complete search history.

(56) References Cited

U.S. PATENT DOCUMENTS

| | | |
|---|---|---|
| 848,711 A | 4/1907 | Weaver |
| 1,072,954 A | 9/1913 | Junn |
| 1,279,654 A | 9/1918 | Charlesworth |
| 1,918,094 A | 7/1933 | Geekas |
| 1,996,986 A | 4/1935 | Weinberg |
| 2,021,989 A | 11/1935 | De Master |
| 2,146,636 A | 2/1939 | Lipchow |
| 3,429,574 A | 2/1969 | Williams |
| 3,448,739 A | 6/1969 | Stark et al. |
| 3,575,415 A | 4/1971 | Fulp et al. |
| 3,595,239 A | 7/1971 | Petersen |
| 4,129,129 A | 12/1978 | Amrine |
| 4,244,362 A | 1/1981 | Anderson |
| 4,401,124 A | 8/1983 | Guess et al. |
| 4,639,252 A | 1/1987 | Kelly et al. |
| 4,641,649 A | 2/1987 | Walinsky et al. |
| 4,669,467 A | 6/1987 | Willett et al. |
| 4,682,596 A | 7/1987 | Bales et al. |
| 4,790,311 A | 12/1988 | Ruiz |
| 4,790,809 A | 12/1988 | Kuntz |
| 4,793,350 A | 12/1988 | Mar et al. |
| 4,807,620 A | 2/1989 | Strul et al. |
| 4,832,048 A | 5/1989 | Cohen |
| 4,840,622 A | 6/1989 | Hardy |
| 4,863,441 A | 9/1989 | Lindsay et al. |
| 4,884,567 A | 12/1989 | Elliott et al. |
| 4,892,104 A | 1/1990 | Ito et al. |
| 4,896,671 A | 1/1990 | Cunningham et al. |
| 4,928,693 A | 5/1990 | Goodin et al. |
| 4,936,281 A | 6/1990 | Stasz |
| 4,960,410 A | 10/1990 | Pinchuk |
| 4,977,897 A | 12/1990 | Hurwitz |
| 4,998,933 A | 3/1991 | Eggers et al. |
| 5,006,119 A | 4/1991 | Acker et al. |
| 5,019,076 A | 5/1991 | Yamanashi et al. |
| 5,047,026 A | 9/1991 | Rydell |
| 5,081,997 A | 1/1992 | Bosley et al. |
| 5,098,431 A | 3/1992 | Rydell |
| 5,112,048 A | 5/1992 | Kienle |
| 5,154,724 A | 10/1992 | Andrews |
| 5,201,756 A | 4/1993 | Horzewski et al. |
| 5,209,741 A | 5/1993 | Spaeth |
| 5,211,183 A | 5/1993 | Wilson |
| 5,221,256 A | 6/1993 | Mahurkar |
| 5,230,349 A | 7/1993 | Langberg |
| 5,281,216 A | 1/1994 | Klicek |
| 5,300,068 A | 4/1994 | Rosar et al. |
| 5,300,069 A | 4/1994 | Hunsberger et al. |
| 5,314,418 A | 5/1994 | Takano et al. |
| 5,318,525 A | 6/1994 | West et al. |
| 5,327,905 A | 7/1994 | Avitall |
| 5,364,393 A | 11/1994 | Auth et al. |
| 5,372,596 A | 12/1994 | Klicek et al. |
| 5,380,304 A | 1/1995 | Parker |
| 5,397,304 A | 3/1995 | Truckai |
| 5,403,338 A | 4/1995 | Milo |
| 5,423,809 A | 6/1995 | Klicek |
| 5,425,382 A | 6/1995 | Golden et al. |
| 5,490,859 A | 2/1996 | Mische et al. |
| 5,497,774 A | 3/1996 | Swartz et al. |
| 5,501,667 A * | 3/1996 | Verduin, Jr. ...... A61M 25/1009 604/101.01 |
| 5,507,751 A | 4/1996 | Goode et al. |
| 5,509,411 A | 4/1996 | Littmann et al. |
| 5,540,681 A | 7/1996 | Strul et al. |
| 5,545,200 A | 8/1996 | West et al. |
| 5,555,618 A | 9/1996 | Winkler |
| 5,571,088 A | 11/1996 | Lennox et al. |
| 5,575,766 A | 11/1996 | Swartz et al. |
| 5,575,772 A | 11/1996 | Lennox |
| 5,599,347 A | 2/1997 | Hart et al. |
| 5,605,162 A | 2/1997 | Mirzaee et al. |
| 5,617,878 A | 4/1997 | Taheri |
| 5,622,169 A | 4/1997 | Golden et al. |
| 5,624,430 A | 4/1997 | Eton et al. |
| 5,667,488 A | 9/1997 | Lundquist et al. |
| 5,673,695 A | 10/1997 | McGee et al. |
| 5,674,208 A | 10/1997 | Berg et al. |
| 5,683,366 A | 11/1997 | Eggers et al. |
| 5,720,744 A | 2/1998 | Eggleston et al. |
| 5,741,249 A | 4/1998 | Moss et al. |
| 5,766,135 A | 6/1998 | Terwilliger |
| 5,779,688 A | 7/1998 | Imran et al. |
| 5,810,764 A | 9/1998 | Eggers et al. |
| 5,814,028 A | 9/1998 | Swartz et al. |
| 5,830,214 A | 11/1998 | Flom et al. |
| 5,836,875 A | 11/1998 | Webster, Jr. |
| 5,849,011 A | 12/1998 | Jones et al. |

(56) References Cited

U.S. PATENT DOCUMENTS

| | | |
|---|---|---|
| 5,851,210 A | 12/1998 | Torossian |
| 5,885,227 A | 3/1999 | Finlayson |
| 5,888,201 A | 3/1999 | Stinson et al. |
| 5,893,848 A | 4/1999 | Negus et al. |
| 5,893,885 A | 4/1999 | Webster, Jr. |
| 5,904,679 A | 5/1999 | Clayman |
| 5,916,210 A | 6/1999 | Winston |
| 5,921,957 A | 7/1999 | Killion et al. |
| 5,931,818 A | 8/1999 | Werp et al. |
| 5,944,023 A | 8/1999 | Johnson et al. |
| 5,951,482 A | 9/1999 | Winston et al. |
| 5,957,842 A | 9/1999 | Littmann et al. |
| 5,964,757 A | 10/1999 | Ponzi |
| 5,967,976 A | 10/1999 | Larsen et al. |
| 5,989,276 A | 11/1999 | Houser et al. |
| 6,007,555 A | 12/1999 | Devine |
| 6,009,877 A | 1/2000 | Edwards |
| 6,013,072 A | 1/2000 | Winston et al. |
| 6,017,340 A | 1/2000 | Cassidy et al. |
| 6,018,676 A | 1/2000 | Davis et al. |
| 6,030,380 A | 2/2000 | Auth et al. |
| 6,032,674 A | 3/2000 | Eggers et al. |
| 6,048,349 A | 4/2000 | Winston et al. |
| 6,053,870 A | 4/2000 | Fulton, III |
| 6,053,904 A | 4/2000 | Scribner et al. |
| 6,056,747 A | 5/2000 | Saadat et al. |
| 6,063,093 A | 5/2000 | Winston et al. |
| 6,093,185 A | 7/2000 | Ellis et al. |
| 6,106,515 A | 8/2000 | Winston et al. |
| 6,106,520 A | 8/2000 | Laufer et al. |
| 6,117,131 A | 9/2000 | Taylor |
| 6,142,992 A | 11/2000 | Cheng et al. |
| 6,146,380 A | 11/2000 | Racz et al. |
| 6,155,264 A | 12/2000 | Ressemann et al. |
| 6,156,031 A | 12/2000 | Aita et al. |
| 6,171,305 B1 | 1/2001 | Sherman |
| 6,179,824 B1 | 1/2001 | Eggers et al. |
| 6,193,676 B1 | 2/2001 | Winston et al. |
| 6,193,715 B1 | 2/2001 | Wrublewski et al. |
| 6,210,408 B1 | 4/2001 | Chandrasekaran et al. |
| 6,217,575 B1 | 4/2001 | Devore et al. |
| 6,221,061 B1 | 4/2001 | Engelson et al. |
| 6,228,076 B1 | 5/2001 | Winston et al. |
| 6,245,054 B1 | 6/2001 | Fuimaono et al. |
| 6,267,758 B1 | 7/2001 | Daw et al. |
| 6,283,983 B1 | 9/2001 | Makower et al. |
| 6,292,678 B1 | 9/2001 | Hall et al. |
| 6,293,945 B1 | 9/2001 | Parins et al. |
| 6,296,615 B1 | 10/2001 | Brockway et al. |
| 6,296,636 B1 | 10/2001 | Cheng et al. |
| 6,302,898 B1 | 10/2001 | Edwards et al. |
| 6,304,769 B1 | 10/2001 | Arenson et al. |
| 6,315,777 B1 | 11/2001 | Comben |
| 6,328,699 B1 | 12/2001 | Eigler et al. |
| 6,360,128 B2 | 3/2002 | Kordis et al. |
| 6,364,877 B1 | 4/2002 | Goble et al. |
| 6,385,472 B1 | 5/2002 | Hall et al. |
| 6,394,976 B1 | 5/2002 | Winston et al. |
| 6,395,002 B1 | 5/2002 | Ellman et al. |
| 6,419,674 B1 | 7/2002 | Bowser et al. |
| 6,428,551 B1 | 8/2002 | Hall et al. |
| 6,450,989 B2 | 9/2002 | Dubrul et al. |
| 6,475,214 B1 | 11/2002 | Moaddeb |
| 6,485,485 B1 | 11/2002 | Winston et al. |
| 6,508,754 B1 | 1/2003 | Liprie et al. |
| 6,524,303 B1 | 2/2003 | Garibaldi |
| 6,530,923 B1 | 3/2003 | Dubrul et al. |
| 6,554,827 B2 | 4/2003 | Chandrasekaran et al. |
| 6,562,031 B2 | 5/2003 | Chandrasekaran et al. |
| 6,562,049 B1 | 5/2003 | Norlander et al. |
| 6,565,562 B1 | 5/2003 | Shah et al. |
| 6,592,612 B1 | 7/2003 | Samson et al. |
| 6,607,529 B1 | 8/2003 | Jones et al. |
| 6,632,222 B1 | 10/2003 | Edwards et al. |
| 6,639,999 B1 | 10/2003 | Cookingham et al. |
| 6,641,603 B2 | 11/2003 | Walker et al. |
| 6,650,923 B1 | 11/2003 | Lesh et al. |
| 6,651,672 B2 | 11/2003 | Roth |
| 6,662,034 B2 | 12/2003 | Segner et al. |
| 6,663,621 B1 | 12/2003 | Winston et al. |
| 6,702,811 B2 | 3/2004 | Stewart et al. |
| 6,709,444 B1 | 3/2004 | Makower |
| 6,723,052 B2 | 4/2004 | Mills |
| 6,733,511 B2 | 5/2004 | Hall et al. |
| 6,740,103 B2 | 5/2004 | Hall et al. |
| 6,752,800 B1 | 6/2004 | Winston et al. |
| 6,755,816 B2 | 6/2004 | Ritter et al. |
| 6,811,544 B2 | 11/2004 | Schaer |
| 6,814,733 B2 | 11/2004 | Schwartz et al. |
| 6,820,614 B2 | 11/2004 | Bonutti |
| 6,834,201 B2 | 12/2004 | Gillies et al. |
| 6,842,639 B1 | 1/2005 | Winston et al. |
| 6,852,109 B2 | 2/2005 | Winston et al. |
| 6,855,143 B2 | 2/2005 | Davison et al. |
| 6,860,856 B2 | 3/2005 | Ward et al. |
| 6,869,431 B2 | 3/2005 | Maguire et al. |
| 6,911,026 B1 | 6/2005 | Hall et al. |
| 6,951,554 B2 | 10/2005 | Johansen et al. |
| 6,951,555 B1 | 10/2005 | Suresh et al. |
| 6,955,675 B2 | 10/2005 | Jain |
| 6,970,732 B2 | 11/2005 | Winston et al. |
| 6,980,843 B2 | 12/2005 | Eng et al. |
| 7,029,470 B2 | 4/2006 | Francischelli et al. |
| 7,056,294 B2 | 6/2006 | Khairkhahan et al. |
| 7,083,566 B2 | 8/2006 | Tornes et al. |
| 7,112,197 B2 | 9/2006 | Hartley et al. |
| 7,335,197 B2 | 2/2008 | Sage et al. |
| 7,618,430 B2 | 11/2009 | Scheib |
| 7,651,492 B2 | 1/2010 | Wham |
| 7,666,203 B2 | 2/2010 | Chanduszko et al. |
| 7,678,081 B2 | 3/2010 | Whiting et al. |
| 7,682,360 B2 | 3/2010 | Guerra |
| 7,828,796 B2 | 11/2010 | Wong et al. |
| 7,900,928 B2 | 3/2011 | Held et al. |
| 8,192,425 B2 | 6/2012 | Mirza et al. |
| 8,257,323 B2 | 9/2012 | Joseph et al. |
| 8,388,549 B2 | 3/2013 | Paul et al. |
| 8,500,697 B2 | 8/2013 | Kurth et al. |
| 9,126,035 B2 * | 9/2015 | Valoir .................. A61N 5/1071 |
| 10,004,550 B2 * | 6/2018 | Ryba ..................... A61B 18/02 |
| 11,339,579 B1 | 5/2022 | Stearns |
| 2001/0012934 A1 | 8/2001 | Chandrasekaran et al. |
| 2001/0021867 A1 | 9/2001 | Kordis et al. |
| 2002/0019644 A1 | 2/2002 | Hastings et al. |
| 2002/0022781 A1 | 2/2002 | McLntire et al. |
| 2002/0022836 A1 | 2/2002 | Goble et al. |
| 2002/0035361 A1 | 3/2002 | Houser et al. |
| 2002/0087153 A1 | 7/2002 | Roschak et al. |
| 2002/0087156 A1 | 7/2002 | Maguire et al. |
| 2002/0111618 A1 | 8/2002 | Stewart et al. |
| 2002/0123749 A1 | 9/2002 | Jain |
| 2002/0147485 A1 | 10/2002 | Mamo et al. |
| 2002/0169377 A1 | 11/2002 | Khairkhahan et al. |
| 2002/0188302 A1 | 12/2002 | Berg et al. |
| 2002/0198521 A1 | 12/2002 | Maguire |
| 2003/0032929 A1 | 2/2003 | McGuckin |
| 2003/0040742 A1 | 2/2003 | Underwood et al. |
| 2003/0040782 A1 | 2/2003 | Walker et al. |
| 2003/0144658 A1 | 7/2003 | Schwartz et al. |
| 2003/0158480 A1 | 8/2003 | Tornes et al. |
| 2003/0163153 A1 | 8/2003 | Scheib |
| 2003/0225392 A1 | 12/2003 | McMichael et al. |
| 2004/0015162 A1 | 1/2004 | McGaffigan |
| 2004/0024396 A1 | 2/2004 | Eggers |
| 2004/0030328 A1 | 2/2004 | Eggers et al. |
| 2004/0044350 A1 | 3/2004 | Martin et al. |
| 2004/0073243 A1 | 4/2004 | Sepetka et al. |
| 2004/0077948 A1 | 4/2004 | Violante et al. |
| 2004/0116851 A1 | 6/2004 | Johansen et al. |
| 2004/0127963 A1 | 7/2004 | Uchida et al. |
| 2004/0133113 A1 | 7/2004 | Krishnan |
| 2004/0133130 A1 | 7/2004 | Ferry et al. |
| 2004/0143256 A1 | 7/2004 | Bednarek |
| 2004/0143312 A1 | 7/2004 | Samson et al. |

(56) References Cited

U.S. PATENT DOCUMENTS

| | | |
|---|---|---|
| 2004/0147950 A1 | 7/2004 | Mueller et al. |
| 2004/0181213 A1 | 9/2004 | Gondo |
| 2004/0210281 A1* | 10/2004 | Dzeng .................. A61F 7/123 607/96 |
| 2004/0230188 A1 | 11/2004 | Cioanta et al. |
| 2005/0004585 A1 | 1/2005 | Hall et al. |
| 2005/0010208 A1 | 1/2005 | Winston et al. |
| 2005/0049628 A1 | 3/2005 | Schweikert et al. |
| 2005/0059966 A1 | 3/2005 | McClurken et al. |
| 2005/0065507 A1 | 3/2005 | Hartley et al. |
| 2005/0085806 A1 | 4/2005 | Auge et al. |
| 2005/0096529 A1 | 5/2005 | Cooper et al. |
| 2005/0101984 A1 | 5/2005 | Chanduszko et al. |
| 2005/0119556 A1 | 6/2005 | Gillies et al. |
| 2005/0123702 A1* | 6/2005 | Beckham ............ A61M 25/104 428/36.3 |
| 2005/0137527 A1 | 6/2005 | Kunin |
| 2005/0149012 A1 | 7/2005 | Penny et al. |
| 2005/0203504 A1 | 9/2005 | Wham et al. |
| 2005/0203507 A1 | 9/2005 | Truckai et al. |
| 2005/0261607 A1 | 11/2005 | Johansen et al. |
| 2005/0288631 A1 | 12/2005 | Lewis et al. |
| 2006/0041253 A1 | 2/2006 | Newton et al. |
| 2006/0074398 A1 | 4/2006 | Whiting et al. |
| 2006/0079769 A1 | 4/2006 | Whiting et al. |
| 2006/0079787 A1 | 4/2006 | Whiting et al. |
| 2006/0079884 A1 | 4/2006 | Manzo et al. |
| 2006/0085054 A1 | 4/2006 | Zikorus et al. |
| 2006/0089638 A1 | 4/2006 | Carmel et al. |
| 2006/0106375 A1 | 5/2006 | Werneth et al. |
| 2006/0135962 A1 | 6/2006 | Kick et al. |
| 2006/0142756 A1 | 6/2006 | Davies et al. |
| 2006/0149166 A1 | 7/2006 | Zvuloni |
| 2006/0189972 A1 | 8/2006 | Grossman |
| 2006/0241586 A1 | 10/2006 | Wilk |
| 2006/0247672 A1 | 11/2006 | Vidlund et al. |
| 2006/0264927 A1 | 11/2006 | Ryan |
| 2006/0276552 A1 | 12/2006 | Barbut et al. |
| 2006/0276710 A1 | 12/2006 | Krishnan |
| 2007/0038277 A1 | 2/2007 | Dae et al. |
| 2007/0055328 A1 | 3/2007 | Mayse et al. |
| 2007/0060879 A1 | 3/2007 | Weitzner et al. |
| 2007/0066975 A1 | 3/2007 | Wong et al. |
| 2007/0118099 A1 | 5/2007 | Trout, III |
| 2007/0123964 A1 | 5/2007 | Davies et al. |
| 2007/0167775 A1 | 7/2007 | Kochavi et al. |
| 2007/0208256 A1 | 9/2007 | Marilla |
| 2007/0225681 A1 | 9/2007 | House |
| 2007/0270791 A1 | 11/2007 | Wang et al. |
| 2008/0039865 A1 | 2/2008 | Shaher et al. |
| 2008/0042360 A1 | 2/2008 | Veikley |
| 2008/0086120 A1 | 4/2008 | Mirza et al. |
| 2008/0097213 A1 | 4/2008 | Carlson et al. |
| 2008/0108987 A1 | 5/2008 | Bruszewski et al. |
| 2008/0146918 A1 | 6/2008 | Magnin et al. |
| 2008/0171934 A1 | 7/2008 | Greenan et al. |
| 2008/0208121 A1 | 8/2008 | Youssef et al. |
| 2008/0243112 A1 | 10/2008 | De Neve |
| 2008/0275439 A1 | 11/2008 | Francischelli et al. |
| 2008/0312644 A1* | 12/2008 | Fourkas ................ A61B 18/02 606/22 |
| 2009/0105742 A1 | 4/2009 | Kurth et al. |
| 2009/0138009 A1 | 5/2009 | Viswanathan et al. |
| 2009/0163850 A1 | 6/2009 | Betts et al. |
| 2009/0177114 A1 | 7/2009 | Chin et al. |
| 2009/0264977 A1 | 10/2009 | Bruszewski et al. |
| 2010/0087789 A1 | 4/2010 | Leeflang et al. |
| 2010/0125282 A1 | 5/2010 | Machek et al. |
| 2010/0168624 A1* | 7/2010 | Sliwa ...................... A61N 7/02 601/3 |
| 2010/0168684 A1 | 7/2010 | Ryan |
| 2010/0179632 A1 | 7/2010 | Bruszewski et al. |
| 2010/0191142 A1 | 7/2010 | Paul et al. |
| 2010/0194047 A1 | 8/2010 | Sauerwine |
| 2011/0046619 A1 | 2/2011 | Ducharme |
| 2011/0082488 A1 | 4/2011 | Niazi |
| 2011/0152716 A1 | 6/2011 | Chudzik et al. |
| 2011/0160592 A1 | 6/2011 | Mitchell |
| 2011/0166633 A1 | 7/2011 | Stull |
| 2011/0190763 A1 | 8/2011 | Urban et al. |
| 2012/0232546 A1 | 9/2012 | Mirza et al. |
| 2012/0265055 A1 | 10/2012 | Melsheimer et al. |
| 2012/0330156 A1 | 12/2012 | Brown et al. |
| 2013/0006139 A1* | 1/2013 | Tiano ................ A61B 18/1233 600/549 |
| 2013/0110098 A1* | 5/2013 | Lalonde ............ A61B 18/1492 606/23 |
| 2013/0184551 A1 | 7/2013 | Paganelli et al. |
| 2013/0184735 A1 | 7/2013 | Fischell et al. |
| 2013/0190796 A1* | 7/2013 | Tilson ................ A61B 18/082 606/192 |
| 2013/0282084 A1 | 10/2013 | Mathur et al. |
| 2014/0206987 A1 | 7/2014 | Urbanski et al. |
| 2014/0277304 A1 | 9/2014 | Stull |
| 2014/0296769 A1 | 10/2014 | Hyde et al. |
| 2015/0165170 A1 | 6/2015 | Beasley et al. |
| 2016/0199224 A1 | 7/2016 | Keller et al. |
| 2016/0220741 A1 | 8/2016 | Garrison et al. |
| 2017/0105871 A1 | 4/2017 | Nierich |
| 2018/0055687 A1 | 3/2018 | Keller et al. |
| 2018/0303663 A1 | 10/2018 | Cattaneo et al. |
| 2018/0360651 A1 | 12/2018 | Brian, III et al. |
| 2019/0021763 A1 | 1/2019 | Zhou et al. |
| 2019/0247035 A1 | 8/2019 | Gittard et al. |

FOREIGN PATENT DOCUMENTS

| | | |
|---|---|---|
| WO | 2017/064134 A1 | 4/2017 |
| WO | 2020/030985 A1 | 2/2020 |

OTHER PUBLICATIONS

International Search Report and Written Opinion received for PCT Patent Application No. PCT/IB2019/051168, mailed on Jun. 3, 2019, 13 pages.

International Search Report and Written Opinion received for PCT Patent Application No. PCT/IB2020/051156, mailed on May 20, 2020, 15 pages.

* cited by examiner

HEAT EXCHANGE AND TEMPERATURE SENSING DEVICE AND METHOD OF USE

TECHNICAL FIELD

The disclosure relates to the field of heating and cooling tissue, in particular the temperature management of tissue using a heat exchange and temperature sensing device.

SUMMARY OF THE DISCLOSURE

The problem of preventing injury to an esophagus caused by heat or cold being delivered to the heart or other nearby tissue may be solved by regulating the temperature of the esophagus using a heat exchange device having a heat exchanger which has a cross section substantially corresponding with the collapsed/relaxed/natural cross section of the inside of the esophagus. In some embodiments, the heat exchanger is a balloon, and inflation of the balloon substantially maintains the esophagus in its natural shape and location (i.e., the esophagus is not displaced towards the left atrium). Some alternative embodiments includes providing a heat exchanger that substantially conforms to or corresponds with the cross section of an esophagus by means other than inflation while substantially maintaining the natural shape and location of the esophagus.

In a first broad aspect, embodiments of the present invention are for a heat exchange and temperature sensing device regulating a temperature of an esophagus when heat or cold is delivered to a left atrium, the method including altering a heat exchange device from an insertable configuration to a heat exchanging configuration which substantially conforms to and corresponds with a cross-section of an inside of the esophagus such that the esophagus is substantially maintained in its natural shape and location, whereby the esophagus is not substantially displaced towards the left atrium.

In a second broad aspect, embodiments of the present invention are for a method of regulating a temperature of an esophagus when heat or cold is delivered to a left atrium, the method including the steps of (a) inflating a heat exchange device from an collapsed configuration to an inflated configuration which substantially conforms to and corresponds with a cross-section of an inside of the esophagus such that the esophagus is substantially maintained in its natural shape and location, whereby the esophagus is not substantially displaced towards the left atrium; and (b) regulating the temperature of the esophagus using the heat exchange device.

In a third broad aspect, embodiments of the present invention are for a method of regulating a temperature of an esophagus when heat or cold is delivered to a left atrium. The method comprises the steps of: (1) measuring the esophagus and selecting a size of a heat exchange device which fits the esophagus; (2) delivering the heat exchange device to a target site; (3) confirming a desired location of the heat exchange device; (4) exchanging heat with the esophagus; (5) confirming that the target site is protected; and (6) retrieving the heat exchange device.

In some embodiments of the third broad aspect, step (1) comprises using imaging such as fluoroscopy, CT, MRI, or EAM.

In some embodiments of the third broad aspect, the heat exchange device comprises a balloon and a main shaft, and the method includes, before step (2), the step of deflating or collapsing the balloon and wrapping or folding the balloon around the main shaft. In some embodiments, wherein the heat exchange device comprises a balloon, the method includes, before step (2), the step of priming the heat exchange device to replace air with fluid. In some embodiments, step (2) comprises advancing the heat exchange device through a nostril. Some embodiments include the heat exchange device further comprising imaging markers and step (2) includes using an imaging system to position the heat exchange device. In some embodiments, step (2) comprises advancing an outer sheath with the heat exchanger and pulling back on the outer sheath when the heat exchanger is positioned to expose the heat exchanger.

In some embodiments of the third broad aspect, step (3) comprises confirming an orientation of the heat exchange device relative to a known anatomical marker by imaging of imaging markers on the heat exchange device. In some such embodiments, the known anatomical marker is the left atrium.

In some embodiments of the third broad aspect, step (4) includes begin circulating a heat exchange fluid through the heat exchange device before heat or cold is delivered to the left atrium. Such embodiments typically include stopping circulating the heat exchange fluid through the heat exchange device after heat or cold is delivered to the left atrium.

In some embodiments, step (5) comprises imaging of a tissue of the esophagus to determine if the tissue has been changed. Some embodiments include step (5) comprising monitoring a physiological parameter which indicates a health factor of a tissue of the esophagus.

Some embodiments of the third broad aspect include prior to step (6), removing the heat exchange fluid from the heat exchange device. In some such embodiments, the heat exchange fluid is removed by vacuuming. Some embodiments include prior to step (6), advancing the outer sheath to cover the heat exchanger, thereby reducing a diameter of the heat exchanger. With typical embodiments of the invention, step (6) includes removing the heat exchange device from a patient.

In a fourth broad aspect, embodiments of the present invention are for a method of monitoring a temperature of a tissue of an esophagus, the method including (a) inflating a device from a collapsed configuration to an inflated configuration which conforms and corresponds with a cross-section of an inside of the esophagus such that the esophagus is maintained in its natural shape and location, whereby the esophagus is not displaced towards a left atrium, and (b) monitoring the temperature of the tissue using sensors on the outside of the device. In some such embodiments, step (b) comprises using sensors on one side of the device.

In a fifth broad aspect, embodiments of the present invention are for a heat exchange and temperature sensing device which regulates the temperature of an esophagus when heat or cold is delivered to a left atrium. The device comprising an insertable configuration and a heat exchanging configuration. In the insertable configuration, the device has a low profile such that it may be readily inserted into an esophagus. In the heat exchanging configuration, an expandable portion of the device may be expanded such that the expandable portion substantially conforms to and corresponds with a cross-section of an inside of the esophagus such that the esophagus is substantially maintained in its natural shape and location, whereby the esophagus is not substantially displaced towards the left atrium.

In some embodiments, the device comprises an elongated shaft comprising a distal end and a proximal end. The elongated shaft defines at least a first lumen and a second lumen. The devices comprises a handle attached to the proximal end of the elongated shaft; and a heat exchanger attached to the distal end of the elongated shaft. The heat exchanger comprises a cavity between a distal end and a proximal end. The cavity is in fluid communication with the first lumen and the second lumen of the elongated shaft.

In some embodiments, the shape of the heat exchanger is constrained by at least one tie which is attached at one end to a posterior surface of the heat exchanger and at the other end to an anterior surface of the heat exchanger.

In some embodiments, the shape of the heat exchanger is constrained by a weld pattern. The weld pattern comprises at least one weld which attaches at least part of an anterior surface of the heat exchanger and a posterior surface of the heat exchanger.

In some embodiments, the at least one weld is a plurality of welds oriented such that heat exchange fluid flowing through the heat exchanger is channeled towards a pair of side edges of the heat exchanger.

In some embodiments, the plurality of welds are oriented as a series of consecutive chevrons along the length of the heat exchanger.

In some embodiments, the plurality of welds are oriented as at least one continuous line running along the length of the heat exchanger.

In some embodiments, the plurality of welds are oriented as a dotted or broken line.

In some embodiments, the heat exchanger comprises at least a pair of parallel tubular members extending between the proximal end and the distal end of the heat exchanger, each parallel tubular member defining a lumen for receiving heat exchange fluid.

In some embodiments, the first lumen comprises a fluid inflow port to allow heat exchange fluid to flow into the heat exchanger.

In some embodiments, the fluid inflow port is proximate a distal end of said heat exchanger.

In some embodiments, the second lumen comprises a fluid outflow port to allow heat exchange fluid to flow out of the heat exchanger.

In some embodiments, the fluid outflow port is proximate a proximal end of said heat exchanger.

In some embodiments, the heat exchanger comprises an anterior surface and a posterior surface, wherein the anterior surface is positioned proximate an anterior wall of the esophagus and the posterior surface is positioned proximate a posterior wall of the esophagus, and wherein the posterior wall comprises a heat insulating layer for insulating the posterior wall of the esophagus from heat exchange fluid circulating through the heat exchanger.

In some embodiments, the heat exchanger further comprises temperature sensors for measuring the temperature of a target site within the esophagus.

In some embodiments, the device comprises at least two radiopaque markers, one of said at least one radiopaque markers being positioned adjacent the proximal end of the heat exchanger, and one of said at least one radiopaque markers being positioned adjacent the distal end of the heat exchanger.

In some embodiments, the device comprises force sensors attached to the heat exchanger for determining the amount of force being applied by the heat exchanger to the esophagus.

In some embodiments, the device comprises at least two electroanatomic mapping electrodes for determining the position of the heat exchanger relative to a target therapy site, one of said at least one electrodes being positioned adjacent the proximal end of the heat exchanger, and one of said at least one electrodes being positioned adjacent the distal end of the heat exchanger.

In some embodiments, the device comprises at least one pacing electrode for delivering a pacing signal to the heart.

In some embodiments, the device comprises at least one electrocardiogram electrode for detecting electrocardiogram signals.

In some embodiments, the device comprises an outer sheath, wherein the outer sheath is movable between a first position and a second position, wherein when the outer sheath is in the first position, the heat exchanger is within the outer sheath, and when the outer sheath is in the second position, the heat exchanger is exposed.

In some embodiments, the cross-sectional shape of the heat exchanger is substantially oblong.

In some embodiments, the device comprises an outer balloon surrounding the heat exchanger.

In some embodiments, the handle comprises a fluid inflow connector in fluid communication with the first lumen for connection with a heat exchange fluid source and a fluid outflow connector in fluid communication with the second lumen for connection with a heat exchange fluid return repository.

In some embodiments, heat exchange fluid is circulated in a closed loop.

In some embodiments, heat exchange fluid is circulated in an open loop.

In some embodiments, the heat exchanger is a balloon.

In some embodiments, the heat exchanger is spaced apart from the distal end of the elongated shaft such that a portion of the elongate shaft extends beyond the heat exchanger. Temperature sensors are attached to the distal end of the elongated shaft for measuring a core body temperature.

In some embodiments, the elongated shaft defines a first lumen, a second lumen, and a third lumen. The cavity of the heat exchanger comprises a first shaping lumen and a heat exchange lumen. The heat exchange lumen is in fluid communication with the first lumen and the second lumen of the elongated shaft. The shaping lumen is in fluid communication with the third lumen of the elongated shaft.

In some embodiments, the third lumen of the elongated shaft allows fluid flow into the shaping lumen of the heat exchanger to inflate the heat exchanger from the insertable configuration to the heat exchanging configuration.

In some embodiments, the handle comprises a shaping lumen connector in communication with the third lumen for connection with a shaping fluid source.

In a sixth broad aspect, embodiments of the present invention are for a heat exchange and temperature sensing device which regulates the temperature of an esophagus when heat or cold is delivered to a left atrium. The device comprises an elongated shaft which comprises a distal end and a proximal end, the elongated shaft defining at least a first lumen, and a second lumen. A heat exchanger is attached to the distal end of the elongated shaft. The heat exchanger comprises a distal end, the distal end comprising a distal blocking member dimensioned in one configuration to substantially conform to and correspond with a cross-section of an inside surface of the esophagus such that the esophagus is substantially maintained in its natural shape and location [NL1]. The heat exchanger comprises at least one irrigation port for dispensing heat exchange fluid within the esophagus, the first lumen being in fluid communication with the at least one irrigation port. The device comprises at least one suction port for removing heat exchange fluid. The at least one suction port is in fluid communication with the second lumen. In use, heat exchange fluid dispensed from the at least one irrigation port is prevented from advancing past the distal blocking member to a stomach.

In some embodiments of the sixth broad aspect, the heat exchanger comprises an insertable configuration and a heat exchanging configuration, where a cross-section of the heat exchanger in the insertable configuration is smaller than a cross-section of the heat exchanger in the heat exchanging configuration.

In some embodiments, the proximal blocking member and the distal blocking member are inflated to provide the heat exchanging configuration, and deflated to provide the insertable configuration.

BRIEF DESCRIPTION OF THE DRAWINGS

In order that the invention may be readily understood, embodiments of the invention are illustrated by way of examples in the accompanying drawings, in which.

DETAILED DESCRIPTION

Figure 1:
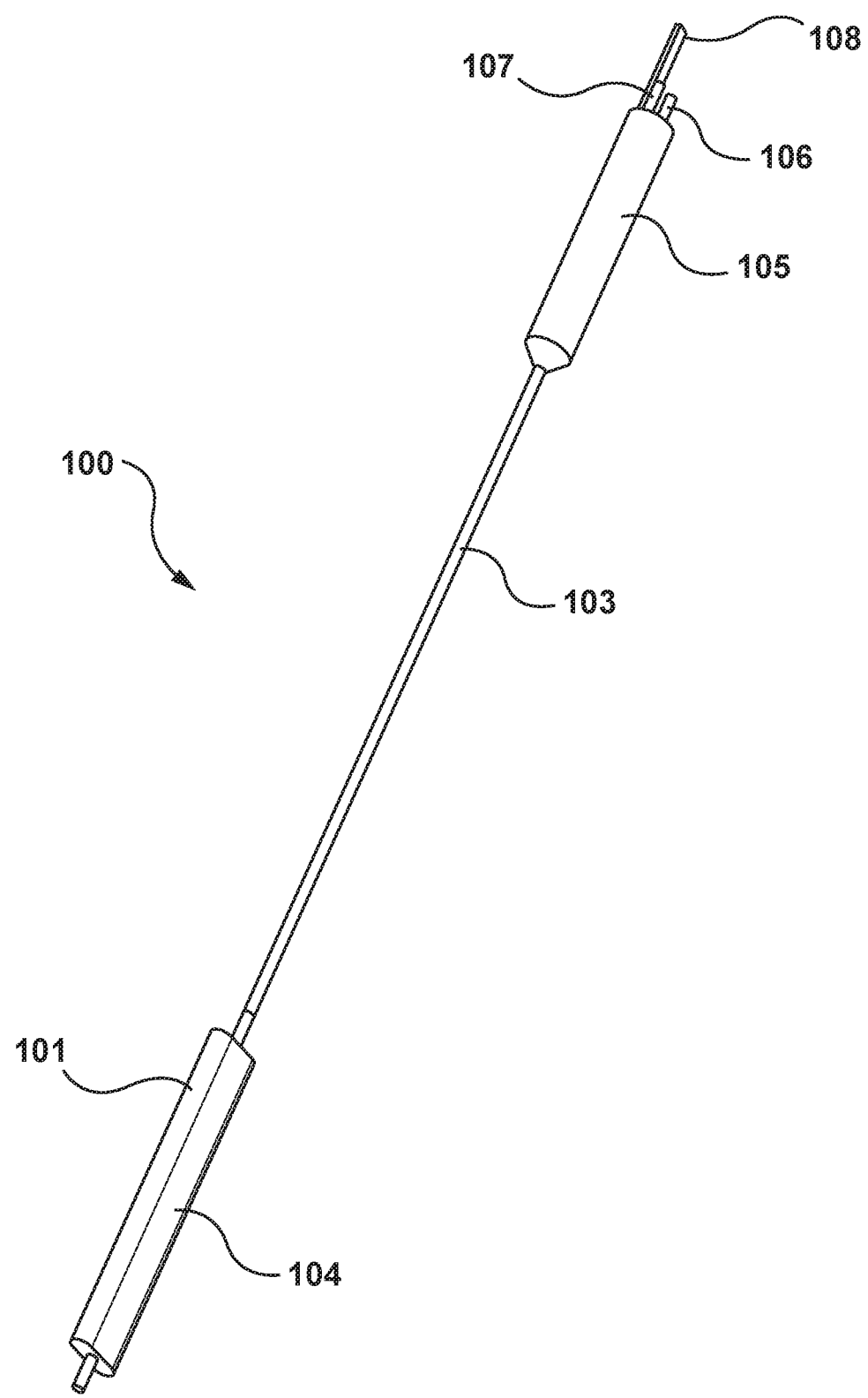
FIG. 1 is an illustration of a heat exchange device.
Figure 2:
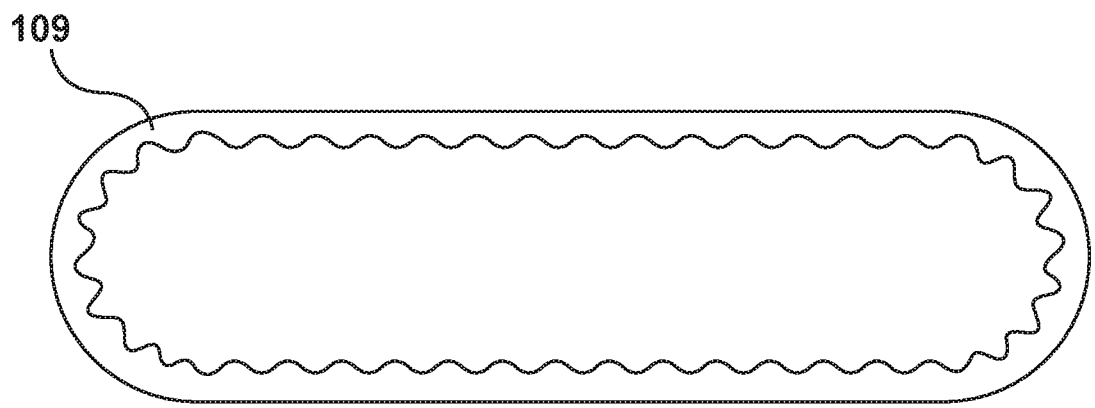
FIG. 2 is an illustration of a cross section of an esophagus.

Inadvertent thermal injury to the esophagus is a dangerous complication of left atrial ablation due to the close proximity of the esophagus to the posterior aspect of the human heart. These thermal injuries can include esophageal mucosal changes, tissue necrosis, ulcer formation, and atrial-esophageal fistula formation.

Current preventative options include reducing the power or duration of ablation when targeting the posterior wall of the left atrium, and monitoring luminal esophageal temperature during ablation so that the ablation can be stopped if there is an unacceptable temperature change in the esophagus. These options may reduce the effectiveness of an ablation treatment.

Attempts have been made in the past to protect the esophagus using cooling balloons. One of the limitations of such balloons is that the balloons typically expand and/or displace the esophagus. Sometimes, a balloon expands and displaces an esophagus to a position closer to the posterior wall of the heart which is the location of heating by delivery of energy for ablation. In such cases, the cooling by the balloon may not be sufficient to protect the esophagus from thermal injury.

The present inventors have conceived of and reduced to practice embodiments of a heat exchange and temperature sensing device and a method of use of said device which is able to prevent injury to an esophagus caused by heat or cold being delivered to the left atrium of the heart. The device regulates the temperature of the esophagus by providing a heat exchanger which can be placed in the esophagus. The heating/cooling balloon has an inflatable cross section corresponding with the collapsed/relaxed/natural cross section of the inside of the esophagus. Inflation of the balloon maintains the esophagus in its natural shape and location such that the esophagus is not displaced towards the left atrium.

In its collapsed or insertable state, the balloon is low in profile and flexible so that it can be inserted into the nose or mouth and advanced to the esophagus. Once positioned in the esophagus, it is expandable to take on a shape with a profile and dimensions corresponding to the collapsed/relaxed/natural cross section of the internal lumen defined by a human esophagus. When fully expanded, the heat exchange balloon makes contact with the endoluminal surface of the esophagus without substantially displacing it from its natural location.

The outer surface of the balloon is in intimate contact with the mucosal layer of the esophagus. It supplies or removes thermal energy in order to keep the esophagus at a desired temperature throughout an ablation procedure. This includes cooling the esophagus during heat-based ablation procedures, (such as radio frequency/RF or high intensity focused ultrasound ablation/HIFU), or warming the esophagus during cold-based ablation procedures (such as cryoablation).

This method and device may be used during left atrial ablation procedures, which are procedures for treating atrial fibrillation in humans. These procedures may include RF/HIFU ablations and cryoablations. In these types of procedures, ablations are performed to create lesions around the ostia of the pulmonary veins, some of which are typically very close to the esophagus. Before the veins are ablated, the balloon portion of the device is positioned in the esophageal lumen and posterior to the left atrium. Once activated, the device either removes thermal energy from the esophagus, or delivers thermal energy to the esophagus to keep it in a desired temperature range throughout the procedure.

The invention can also be used in other cardiac procedures where the temperatures in the heart reach undesired levels. It can also be used in other areas of the body where temperature management is required to protect sensitive structures, for example ablation of the prostate to treat cancer. Additionally, the invention can be used to control patient temperature, for example to induce and maintain hypothermia in critically ill patients, or to warm patients with body temperatures below normal, such as when they are under general anesthesia and undergoing surgery.

With specific reference now to the drawings in detail, it is stressed that the particulars shown are by way of example and for purposes of illustrative discussion of certain embodiments of the present invention only. Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Heat Exchanging Fluid Device

Figure 29:
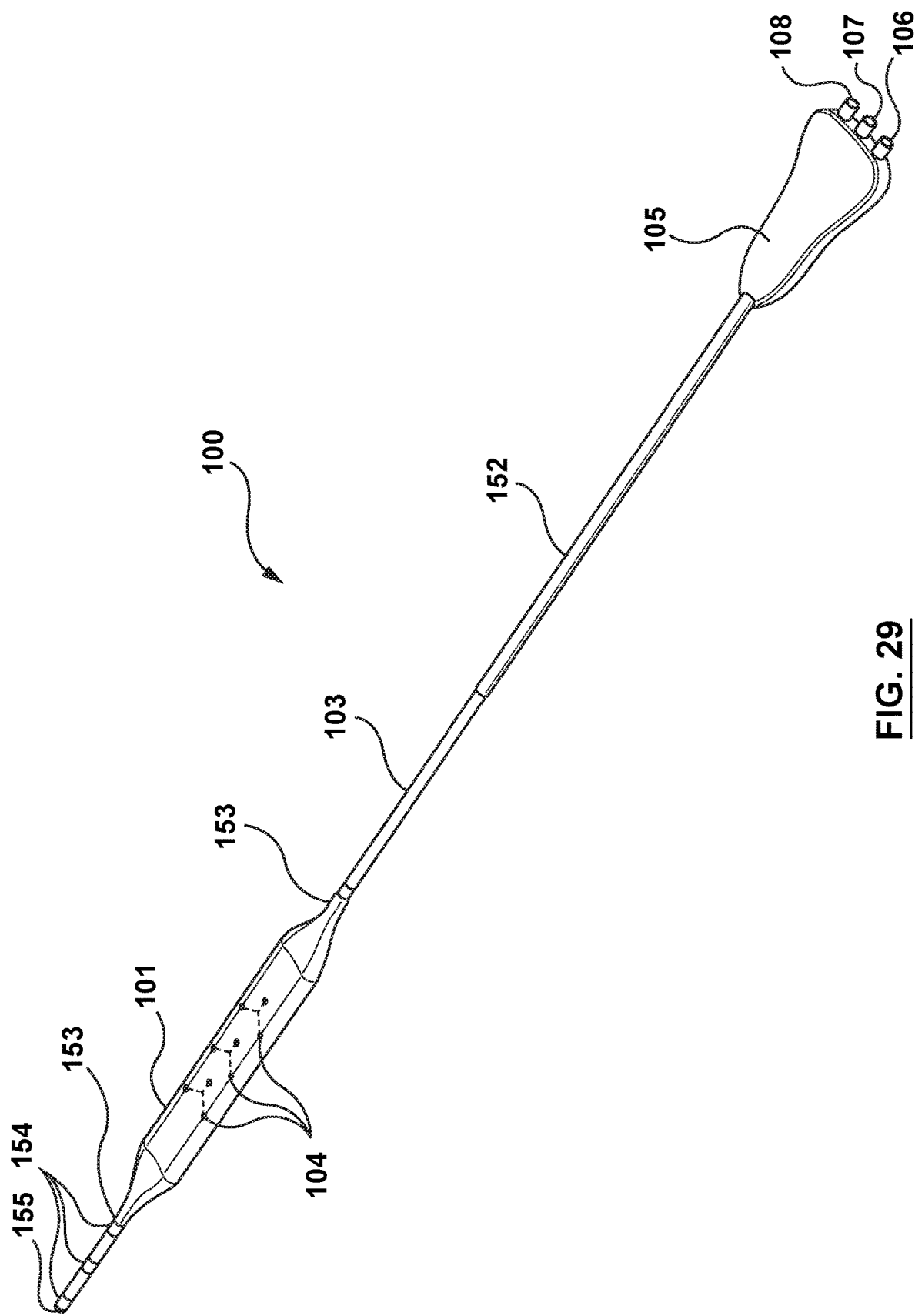
FIG. 29 is another embodiment of a heat exchange device which includes an outer sheath.

An example of a heat exchange and temperature sensing device 100 for use in the method described herein is illustrated in FIG. 1. Heat exchanging fluid device 100 comprises a main shaft 103 which has balloon heat exchanger 101 at one end, with temperature sensor 104 being associated with balloon heat exchanger 101. Handle 105 is at the other end of main shaft 103. The end of heat exchange device 100 having handle 105 also includes fluid inflow 106, fluid outflow 107, and temperature sensor connector 108. Another embodiment of heat exchange and temperature sensing device 100 is shown in FIG. 29. As will be described in more detail below, heat is exchanged by allowing fluid to be circulated through the balloon 101 via fluid inflow 106 and fluid outflow 107.

In one embodiment, the fluid is made substantially of water. For example, the fluid may be distilled water or saline. Alternately, the fluid may be a substance that is not substantially water, such as an oil based or petroleum product. In addition, the fluid may contain additives, for example a disinfectant, or stabilizer. The temperature, flow rate, and pressure of the fluid is managed through an external controller which includes a pump. The heat exchanging fluid device of the present invention is described in greater detail below.

Figure 16:
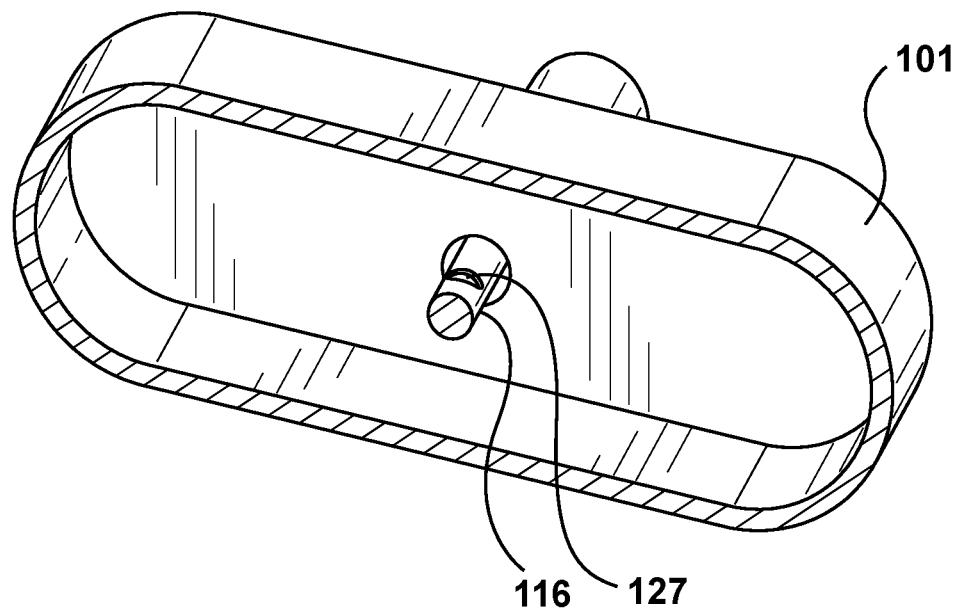
FIG. 16 is an illustration of an inlet port with a single hole.

The heat exchanging fluid device comprises inlet port(s) and outlet port(s). The inlet port(s) is the location where the fluid enters the heat exchanger (e.g. a balloon). There may be one or multiple inlet ports which service different locations in the heat exchanger. In one embodiment, the inlet port 116 is a hole on tube 127 located inside the heat exchanger 101 (e.g. FIG. 16. Inlet port with single hole). The fluid advances through fluid inflow 106 and tube 127 until it reaches the hole 116 and enters the heat exchanger 101. Fluid inflow 106 and tube 127 are in fluid communication to allow fluid to be supplied to the heat exchanger via fluid inflow 106. In some embodiments the tube 127 is made of plastic, possibly reinforced with materials such as a metal coil or braid within the tube wall. The hole 116 may be at the distal end of the heat exchanger 101, or the proximal end of the heat exchanger 101, or at any location in between. In the embodiments depicted in FIGS. 1 and 29, inlet port(s) are in fluid communication with fluid inflow 106. In some embodiments, inlet port(s) are part of fluid inflow 106.

In some embodiments, heat exchange fluid is circulated in a closed loop. After heat exchange fluid leaves the heat exchange device via fluid outflow, the heat exchange fluid is re-heated/re-cooled then introduced back into the heat exchange device via fluid inflow. Heat exchange fluid may thus be continuously recirculated.

In other embodiments, heat exchange fluid is circulated in an open loop. Heat exchange fluid leaving the heat exchange device is discarded or disposed of.

Figure 17:
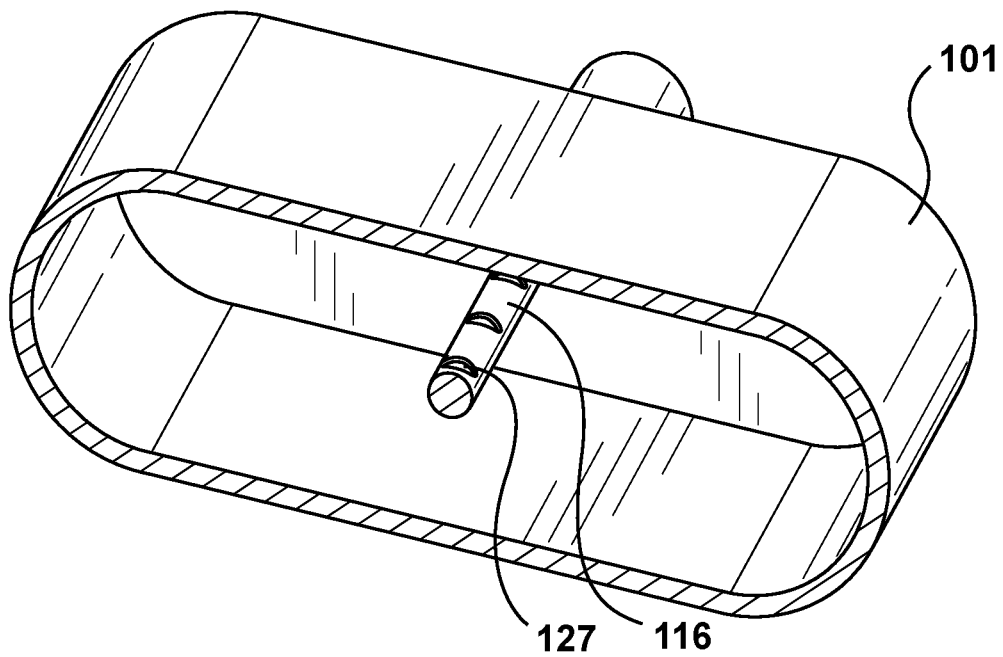
FIG. 17 is an illustration of an inlet port with multiple holes.
Figure 18:
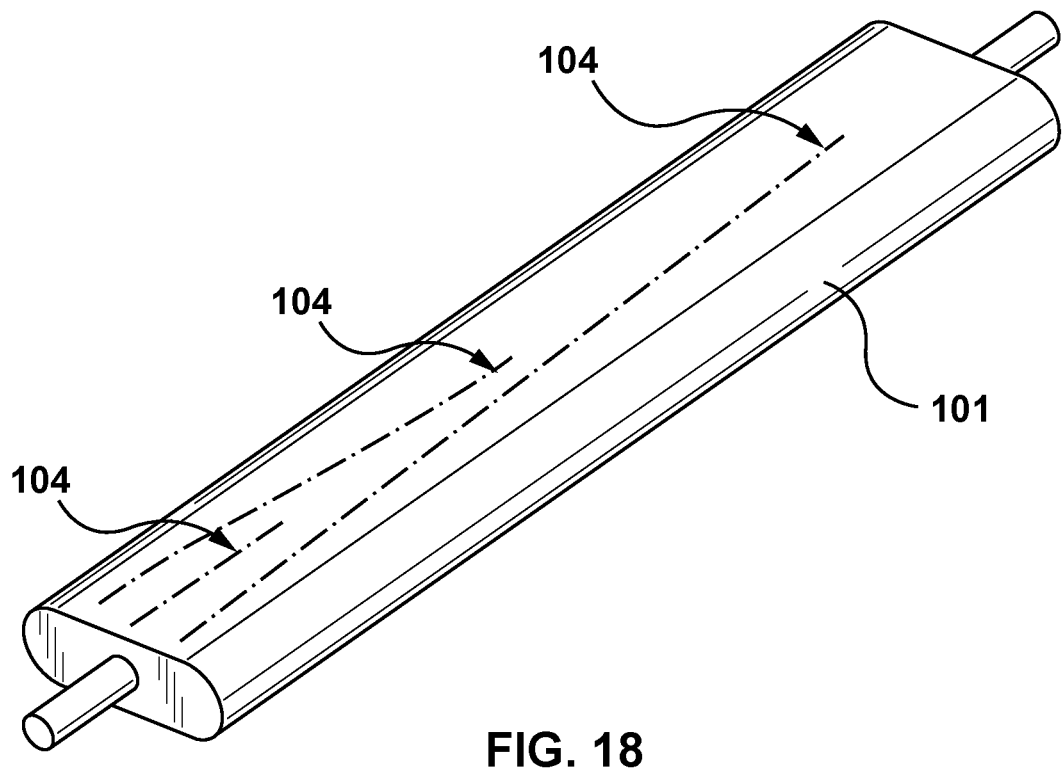
FIG. 18 is an illustration of temperature sensors affixed to balloon surface.
Figure 19:
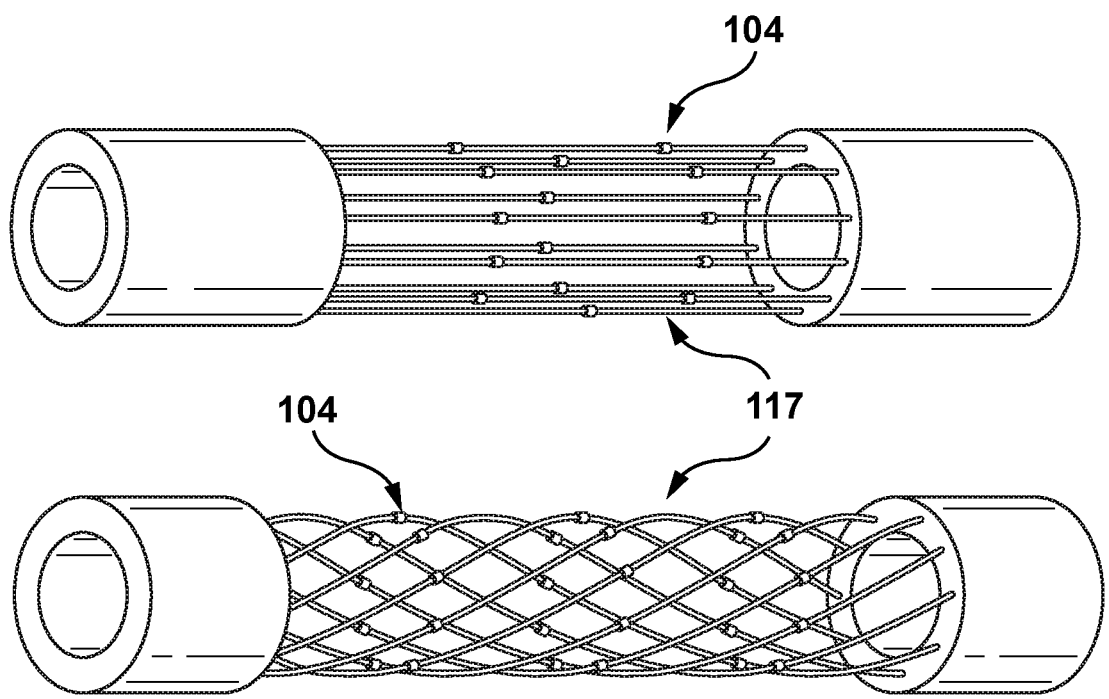
FIG. 19 is an illustration of temperature sensors mounted on the embodiments depicted in FIGS. 13 and 14.

In an alternate embodiment, the tube has multiple holes spaced along the tube (e.g. FIG. 17. Tube 127 with multiple inlet ports 116). The fluid advances through the tube until it reaches one of the multiple holes, and enters the heat exchanger in multiple locations simultaneously. The holes may be spaced linearly at regular intervals, or in a helical pattern around the tube, or in any other type of pattern along the tube. Typically, the holes are located to optimize one of the features of the heat exchange. For example, the holes may be located to maximize the thermal performance of the heat exchanger, or to control pressure inside the heat exchanger.

The outlet port is the location where the fluid exits the heat exchanger. There may be one or multiple outlet ports which service different locations in the heat exchanger. In one embodiment, the outlet port is a tube with a single hole located inside the heat exchanger. The fluid enters the heat exchanger at the inlet port(s), travels through the heat exchanger, and exits at the outlet port. In some embodiments, the tube is made of plastic, possibly reinforced with materials such as a metal coil or braid within the tube wall. The hole may be at the distal end of the heat exchanger, or the proximal end of the heat exchanger, or at any location in between. In the embodiment depicted in FIGS. 1 and 29, outlet port(s) are in fluid communication with fluid outflow 107. In some embodiments, outlet port(s) are part of fluid outflow 107.

In another embodiment, the tube 127 has multiple holes spaced along its length. The fluid in the heat exchanger exits through one of the multiple holes simultaneously. The holes may be spaced linearly at regular intervals, or in a helical pattern around the tube, or in any other type of pattern along the tube. Typically, the holes are located to optimize one of the features of the heat exchange. For example, the holes may be located to maximize the thermal performance of the heat exchanger, or to control pressure inside the heat exchanger.

The heat exchange device 100 may comprise a sheath or sleeve. A sheath 152 is depicted in FIG. 29. As will be discussed in greater detail below, a heat exchanger 101 may be collapsed/wrapped/deflated around a shaft 103 such that the heat exchanger 101 may be received into a sheath 152. Accordingly, sheath 152 is dimensioned to receive heat exchanger 101 when it is in a collapsed/wrapped/deflated configuration. This feature may be provided to avoid damage to the body lumen when the heat exchanger is being advanced therethrough. Heat exchanger 101 may be provided with radiopaque (RO) markers or electroanatomic mapping (EAM) 153 for using imaging techniques to determine the location of the heat exchanger 101 relative to known anatomical markers. The embodiment depicted in FIG. 29 is provided with a body temperature sensor 155. Body temperature sensor 155 is spaced apart from heat exchanger 101 such that the temperature sensed by sensor 155 is of the body lumen and not of the heat exchanger 101. Items 154 are additional electrodes for either pacing or detecting electric signals. For pacing, pacing electrodes would be provided. For detecting electric signals, electrocardiogram electrodes would be provided. The various sensors and electrodes may be connected to one or more external devices through connector 108.

Figure 56:
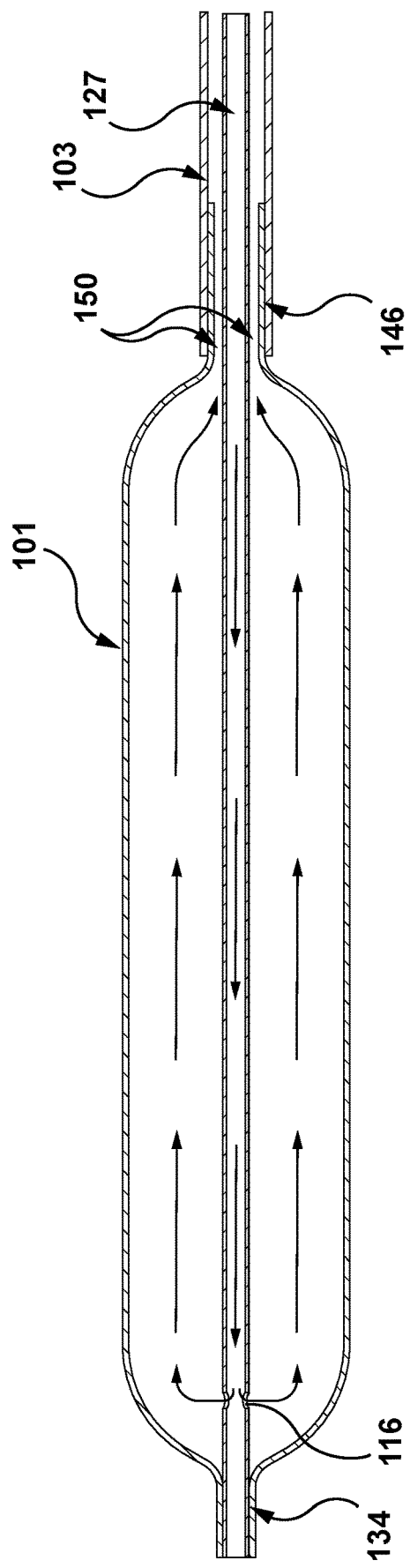
FIG. 56 is a cross-sectional plan view of a heat exchanger attached to a shaft and an inlet tube.

FIG. 56 illustrates an embodiment of heat exchanger 101 with inlet and outlet ports. The heat exchanger 101 comprises proximal neck portion 146 and distal neck portion 134. In this embodiment, inlet ports 116 are positioned proximate the distal end of heat exchanger 101. Fluid travels through tube 127 along the arrows shown in the figure. When the fluid reaches the outlet ports 116, fluid exits tube 127 and enters the heat exchanger 101. The fluid then follows a return path towards a proximal end of the heat exchanger 101 (i.e., towards proximal neck portion 146) and leaves the heat exchanger 101 via outlet ports 150. In this embodiment, outlet ports 150 are formed by providing a circumferential gap between the proximal neck portion 146 of the heat exchanger 101 and the tube 127. The diameter of tube 127 is somewhat narrower than the inner diameter of shaft 103 to permit fluid to flow there between and back towards the fluid outflow 107. Tube 127 is attached via welding or other means to distal neck portion 146 such that fluid is prevented from escaping the heat exchanger 101 out from the distal neck portion 146. Proximal neck portion 146 is attached via welding or other means to shaft 103 such that fluid is prevented from escaping the heat exchanger 101 and shaft 103.

Figure 57:
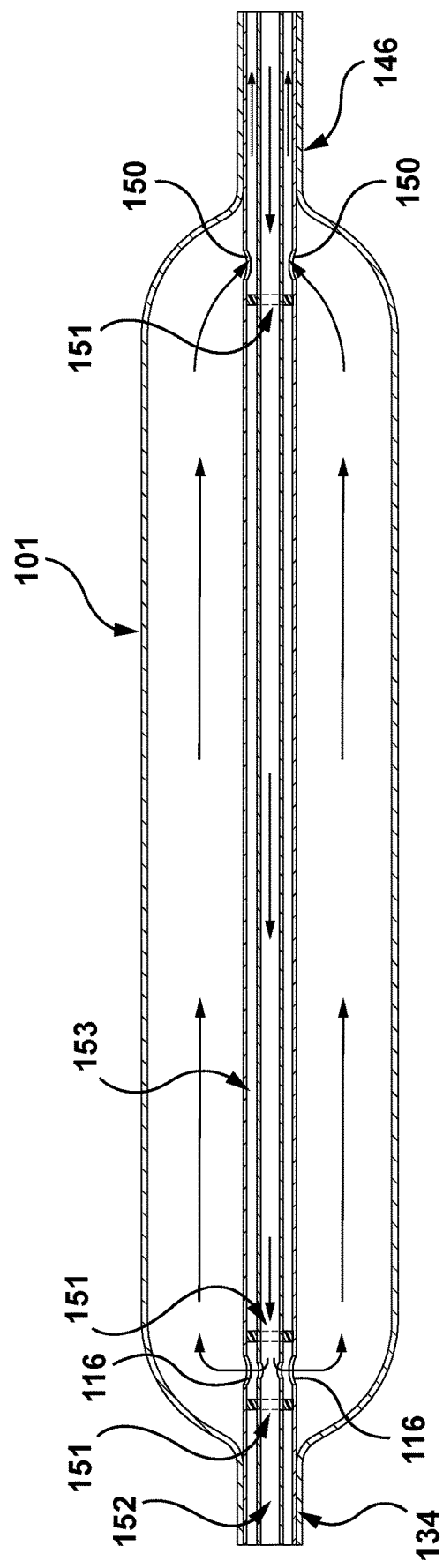
FIG. 57 is a cross-sectional plan view of a heat exchanger attached to a shaft, an inlet tube, and an outlet tube.

FIG. 57 illustrates a further embodiment of a heat exchanger 101 with inlet and outlet ports. In this embodiment, an inner inlet tube 152 and an outer outlet tube 153 are provided. Fluid flows into the heat exchanger 101 via ports 116. Both the inner inlet tube 152 and the outer outlet tube 153 comprise ports 116 to allow fluid to pass therethrough. Means are provided to prevent fluid from flowing into the space between inner inlet tube 152 and outer outlet tube 153. In this embodiment, O-rings 151 are placed on either side of ports 116. The O-rings 151 prevent fluid from flowing into the space between the inner inlet tube 152 and the outer outlet tube 153. Outer outlet tube 153 comprise outlet ports 150. Fluid leaving the heat exchanger 101 flows into the outlet ports 150 and towards a fluid outflow.

(b) A heat exchanger (a cavity for circulation of fluid). In one embodiment, the cavity is a balloon—this embodiment will be described in greater detail below. Some embodiments of balloons are made of a non-compliant material such as Nylon 12 or PET. Alternative balloon embodiments are made of a compliant material such as Pebax® or urethane.

(c) Features augmenting contact. To ensure appropriate heat exchange is occurring at the esophagus, the heat exchanger must maintain adequate contact with the tissue. The heat exchanger having contract with the esophagus also ensures any heat sensors on the heat exchanger are contacting the inner surface of the esophagus. The following optional features may be included for augmenting the contact between the heat exchanger and the tissue:

(c.1) Controllable heat exchanger size. This feature includes the heat exchanger being expandable or contractable to fit the size of the esophagus and promote contact with the tissue. The change in size may be controlled with pressure, such as the internal pressure in a balloon, or external pressure exerted by the anatomy on the device. Alternately, the size may be controlled with a mechanical expansion/contraction mechanism, which may further comprise a feedback loop from the forces exerted on the device (detected via force sensors) to achieve the optimal contact force.

(c.2) Conformable heat exchanger shape. This feature includes the expansion of the heat exchanger being constrained in one or more axes, using the balloon designs outlined above and through the use of compliant and non-compliant materials, thin films with ties or welds, and shape memory materials. In alternative embodiments, the heat exchanger is moldable to the esophagus shape through the use of compliant materials that respond to forces exerted by the tissue.

(c.3) Anchoring feature. The heat exchange device may have an anchoring feature or features such as notches, necks, collars, or hooks that allow the device to engage internally with anatomical features to hold it in place. In alternative embodiments, the device has an anchoring feature such as tape, Velcro, and straps that allow it to engage externally with other devices such as an endotracheal tube or a nasal bridle to hold it in place.

(c.4) Suction feature. The heat exchange device may incorporate suction to hold the tissue against the surface of the device to ensure appropriate tissue contact. Tissue suction may also be used to ensure that tissue is pulled away from the area where heat is being applied. For example, when esophagus tissue is pulled towards the heat exchanger, it may be consequently pulled away from the left atrium of the heart where ablation is taking place.

Also, force may be applied to the esophagus or the device to maintain adequate tissue contact. This may be a force external to the patient, or applied from within the patient from the heat exchange device, or from another device (for example, by suction feature as described above).

An additional technique to ensure proper heat exchange is to assess the amount of tissue contact between the heat exchanger and the tissue at the target site. The heat exchange device may comprise force sensors to measure the amount of force between the tissue and the heat exchanger. This force may be used in a feedback loop in communication with the device to maintain optimal force between the heat exchanger and the tissue.

Yet another technique to ensure proper heat exchange is to use heat flux sensors to measure the heat flux at any given part of the tissue at the target site. A greater heat flux measurement represents greater heat transfer between the tissue and the heat exchanger.

Balloon Heat Exchanger

Some embodiments of the heat exchanging fluid device described herein comprise a balloon heat exchanger 101 (FIG. 1). The balloon 101 comprises a cavity for circulation of fluid. Embodiments of such heat exchange balloons are illustrated in FIGS. 2, 5-15, 18-24, 26-30, 34-35, and 38-50.

Figure 3:
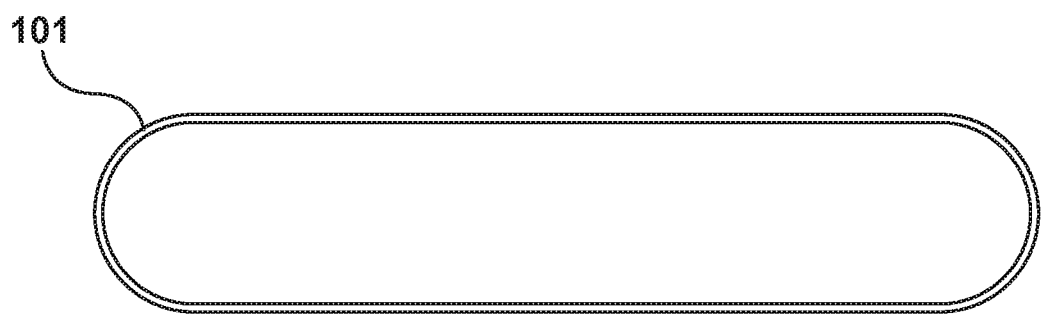
FIG. 3 is an illustration of a cross section of a balloon heat exchanger.
Figure 4:
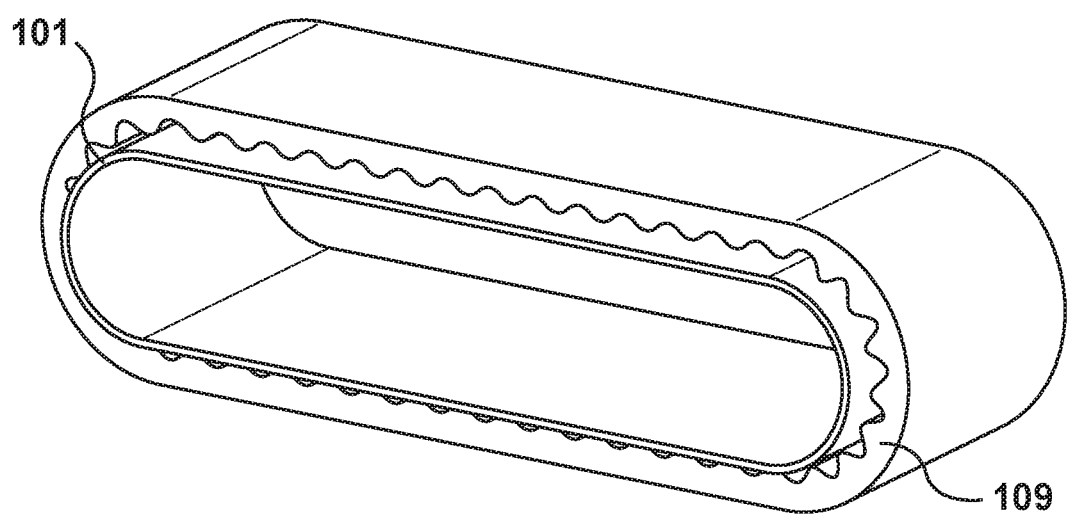
FIG. 4 is an illustration of a balloon heat exchanger expanded in an esophagus.
Figure 5:
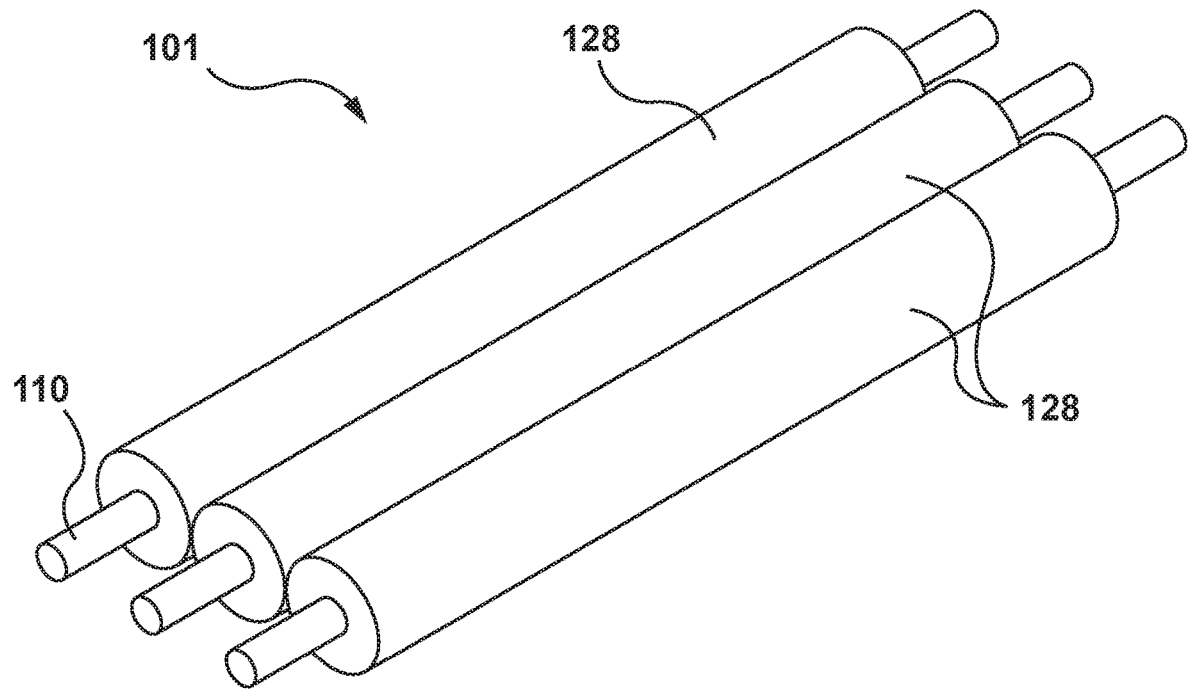
FIG. 5 is an illustration of three balloons side-by-side.
Figure 6:
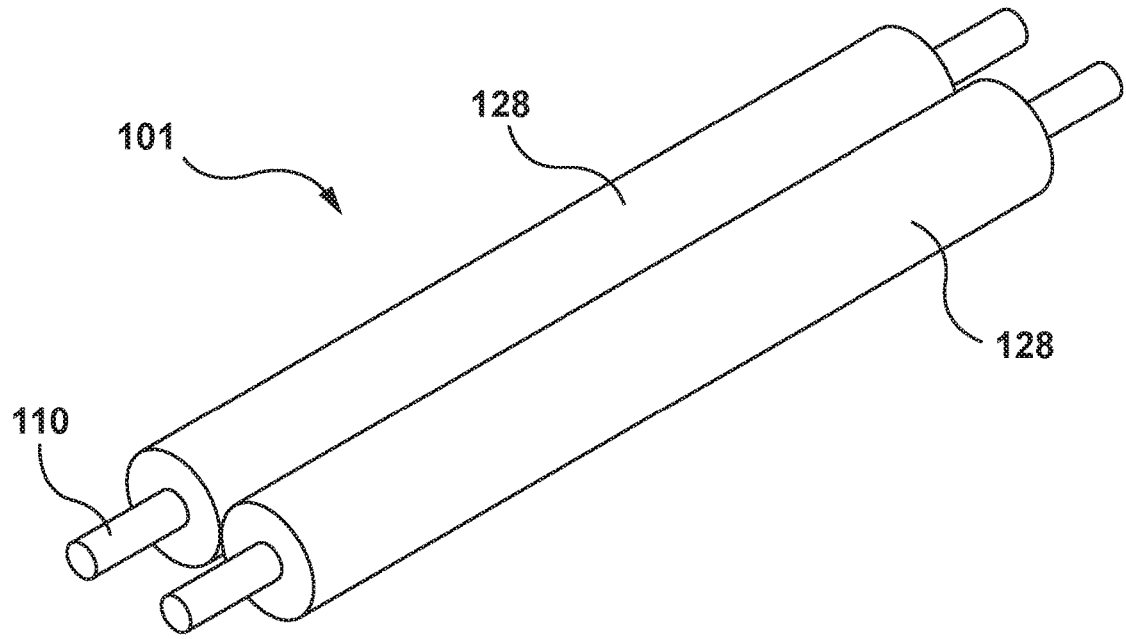
FIG. 6 is an illustration of balloons with centered necks.

The inflated cross-sectional shape of such a balloon mimics the natural shape of the inside of a human esophagus. In its collapsed shape, a human esophagus 109 typically has a cross-section of around 1.5-3 cm wide and around 0-0.5 cm high (e.g. FIG. 2. cross section of esophagus). The balloon of the invention (e.g. FIG. 3. cross section of balloon heat exchanger 101) maintains a cross-section of similar dimensions in order to make intimate contact with the mucosal layer of the esophagus without displacing it, i.e., the balloon is expandable but is restrained in one or more axes to reduce forces exerted on the abutting surfaces of the esophagus (e.g. FIG. 4. balloon heat exchanger 101 expanded in esophagus 109).

The desired shape of the balloon heat exchanger 101 can be realized in a number of ways. In one embodiment (see FIGS. 5-7), at least two cylindrical balloons are abutted and held side-by-side. For example, if 3 balloons (see FIG. 5) with an inflated diameter of 5 mm are placed side-by-side, the overall dimensions of the cross-section of the heat exchanger (when expanded) is approximately 15 mm wide and 5 mm tall. Thus, both the number of cylindrical balloons and the inflated diameter of the balloons can be varied to vary the overall dimensions of the cross-section of the heat exchanger.

Figure 7:
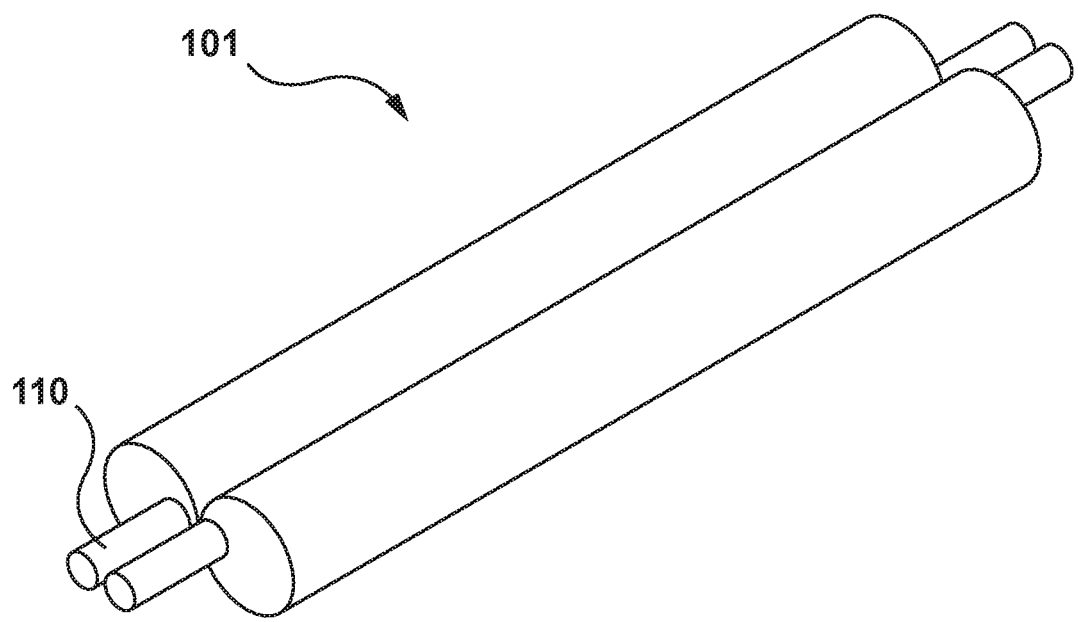
FIG. 7 is an illustration of balloons with offset necks.

This approach may be used with any number of cylindrical balloons abutted side-by-side. In some embodiments, these balloons are cylindrical with balloon necks 110 in the middle of the balloon (FIG. 6. balloons with centered necks), or in some other embodiments, with offset balloon necks 110 located away from the center of the balloon (FIG. 7. balloons with offset necks). Balloon necks 110 may be in fluid communication with the main body of balloon 128. Balloon necks 110 may be connected with input ports or output ports to allow fluid flow through the balloon.

Figure 8:
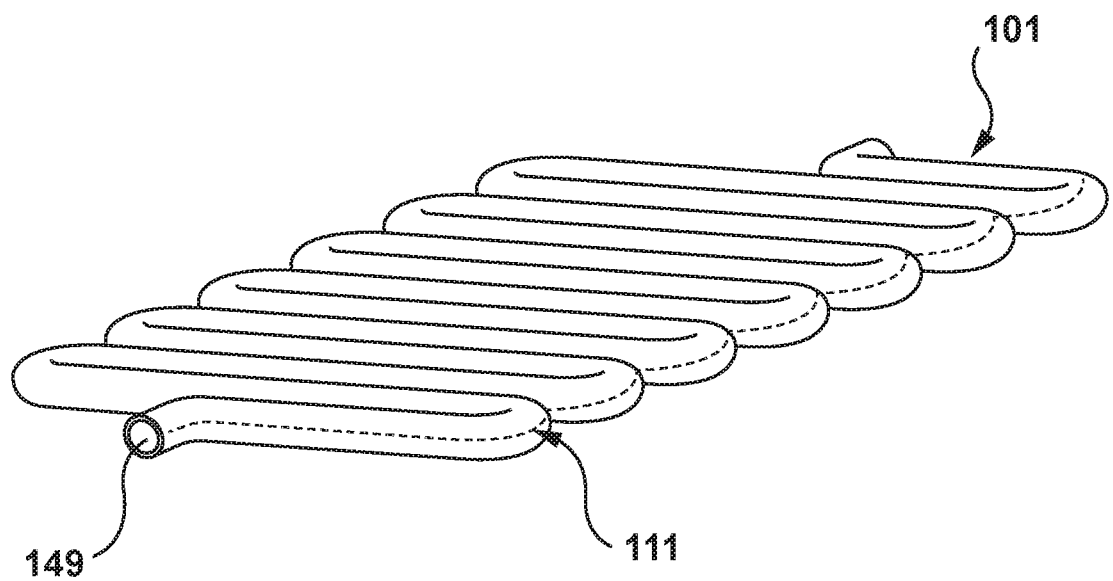
FIG. 8 is an illustration of a serpentine welded balloon.

In another embodiment, the desired shape of the balloon is achieved by welding thin films together. The films may be plastic such as urethane, or another material that is formable in thin film. In one embodiment, the films are welded in a serpentine shape. FIG. 8 illustrates a serpentine welded balloon having top and bottom films (when in the orientation of FIG. 8) welded together along weld lines 111. The top and bottom films, when welded, result in a lumen 149 through which fluid may be circulated to perform the heat exchange.

Figure 9:
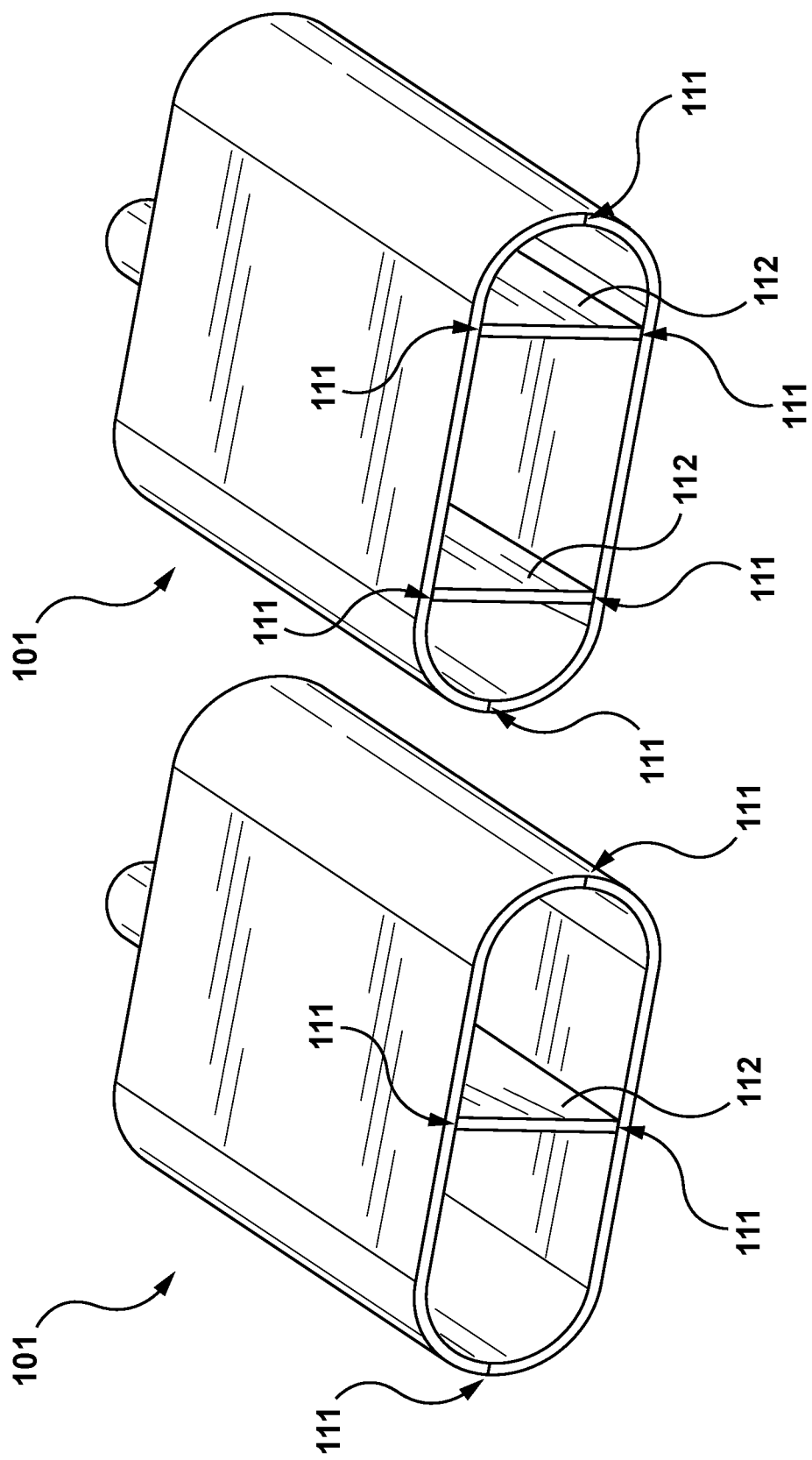
FIG. 9 is an illustration of a welded balloons with ties.
Figure 10:
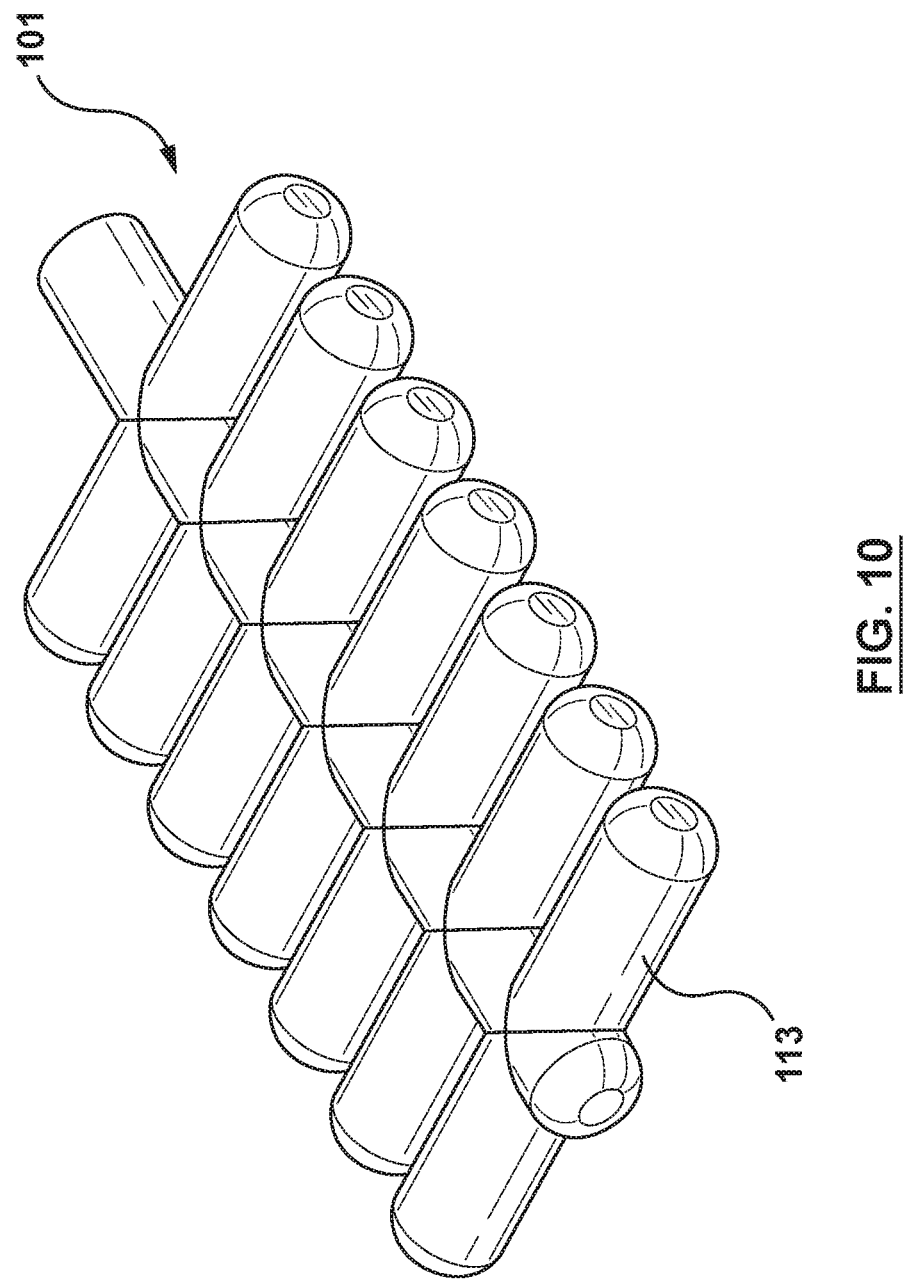
FIG. 10 is an illustration of a welded balloon with fins.

In some embodiments the welding technique is used to add singular or multiple ties inside a balloon to prevent it from expanding in undesired axes. FIG. 9 shows two examples of welded balloons with ties with the balloon on the left having a single tie 112 and the balloon on the right of the figure having two lies. Weld lines 111 weld the ties in place.

In other embodiments a balloon shape is constrained with welds. FIGS. 27-28, 30, and 38-50 feature balloon heat exchangers with a variety of weld patterns. Varying the weld patterns impact the lengthwise and widthwise inflatability and rigidity of the balloon as well as the flow of fluid through the balloon.

Figure 28:
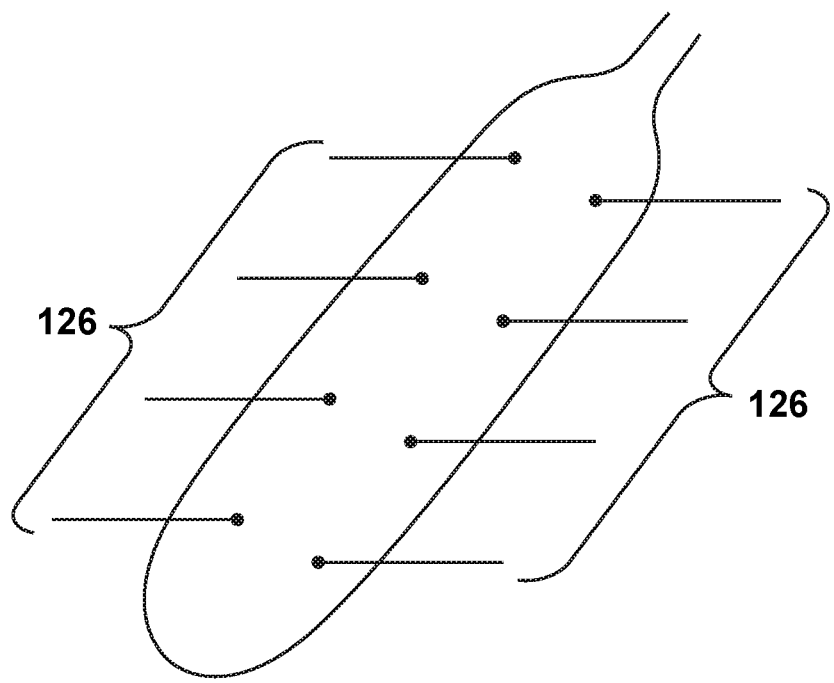
FIG. 28 is an illustration of a balloon with tack welds.
Figure 42:
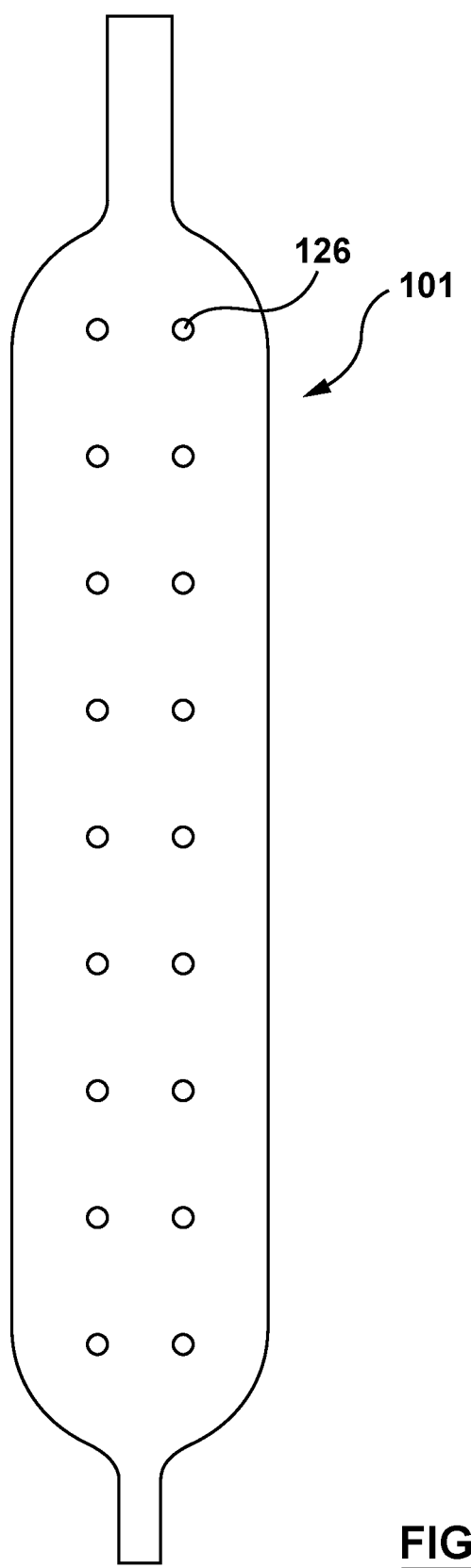
FIG. 42 is an illustration of a further embodiment of a balloon with tack welds.
Figure 43:
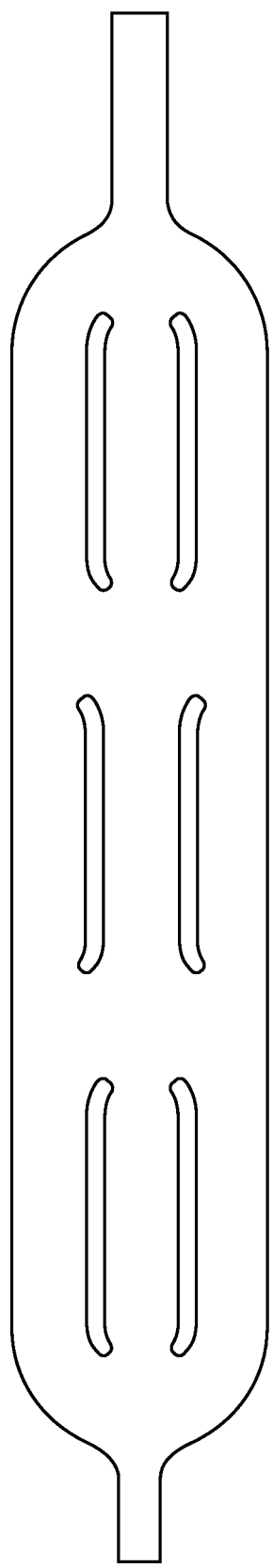
FIG. 43 is an illustration of a balloon with a pair of broken weld lines.
Figure 44:
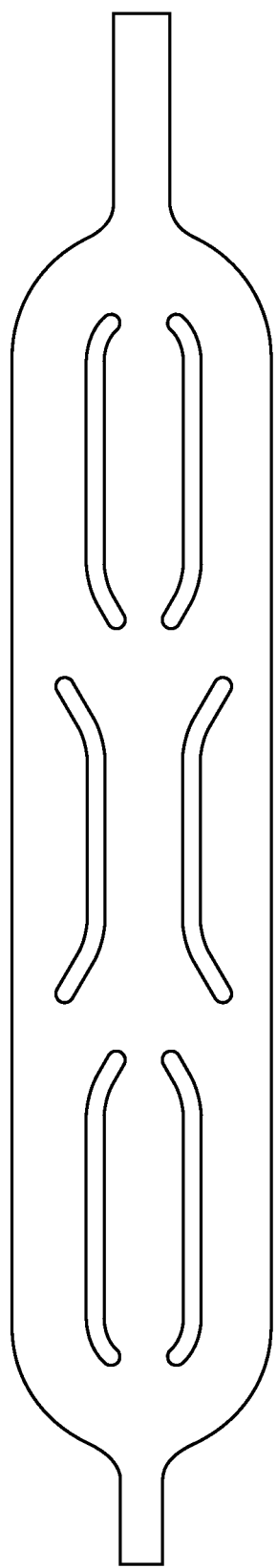
FIG. 44 is an illustration of a further embodiment of a balloon with a pair of broken weld lines.
Figure 45:
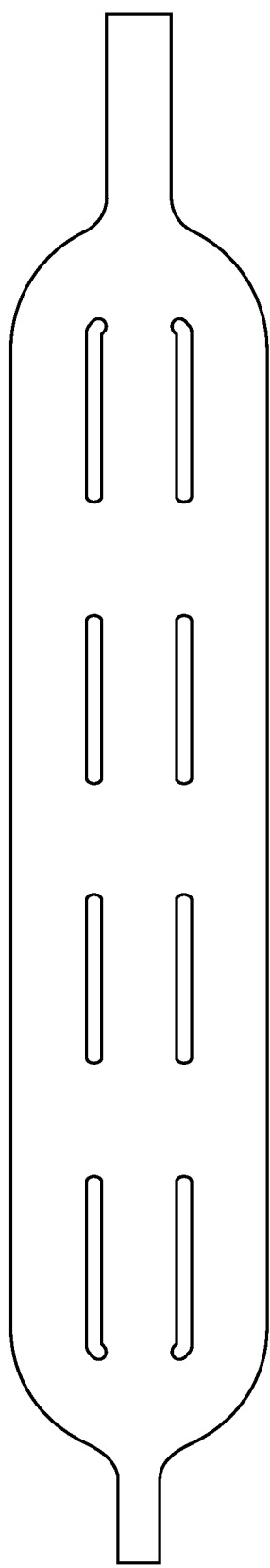
FIG. 45 is an illustration of yet another embodiment of a balloon with a pair of broken weld lines.
Figure 46:
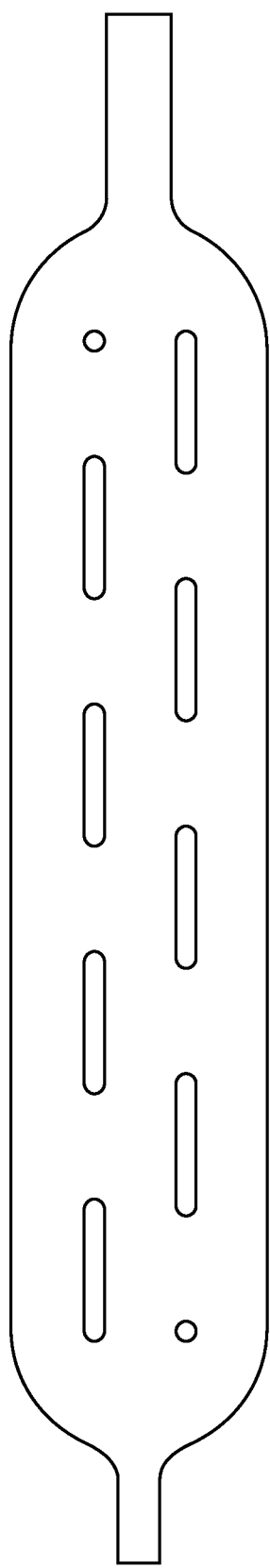
FIG. 46 is an illustration of a balloon with a pair of broken weld lines and a pair of tack welds.

FIGS. 28 and 42 illustrate balloons with tack welds 126 (or spot welds). The weld pattern in this embodiment results in multiple fluid flow channels that extend along the length and the width of the balloon. These channels are "open" such that fluid flowing within one channel may flow to another channel. This allows fluid to flow into any particular area of the balloon, even if the balloon is bent, folded, or otherwise restricted from freely inflating in that area. These fluid channels allow the balloon to be more easily inflated and deployed in applications where the balloon is introduced into the esophagus deflated and wrapped around a central shaft (such as shown in FIG. 29) along the balloon's lengthwise axis. Also, these embodiments allow the mixing of flow amongst the various fluid channels, which promotes heat exchange across the entire surface of the balloon.

Figure 27:
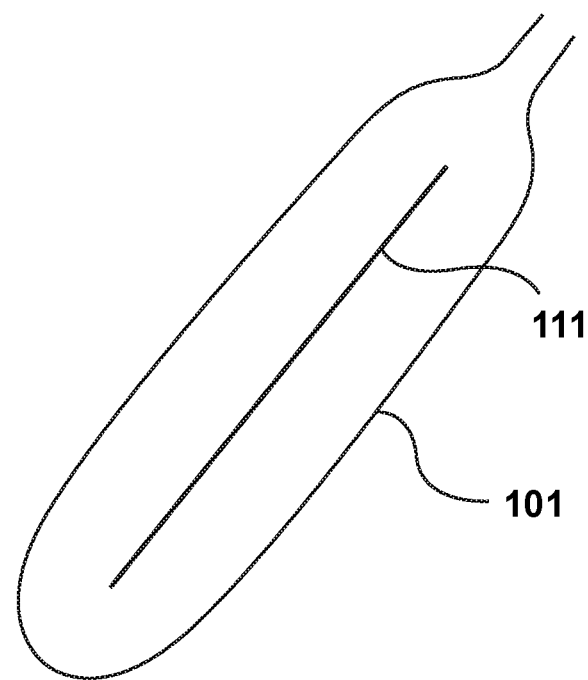
FIG. 27 is an illustration of a balloon with a weld line.
Figure 38:
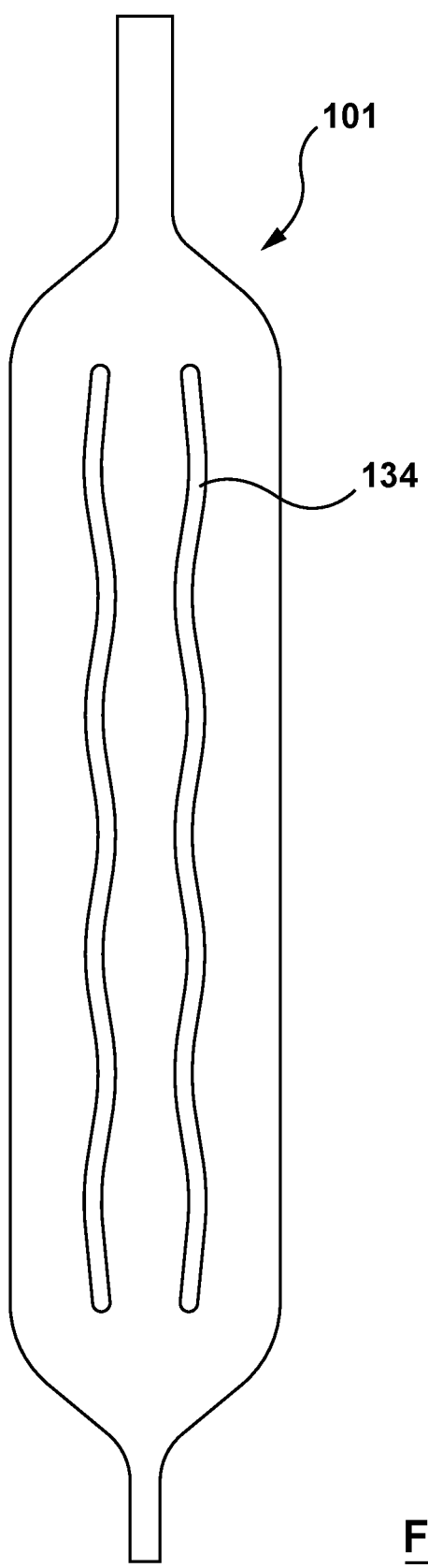
FIG. 38 is an illustration of a balloon with a pair of wavy weld lines.
Figure 39:
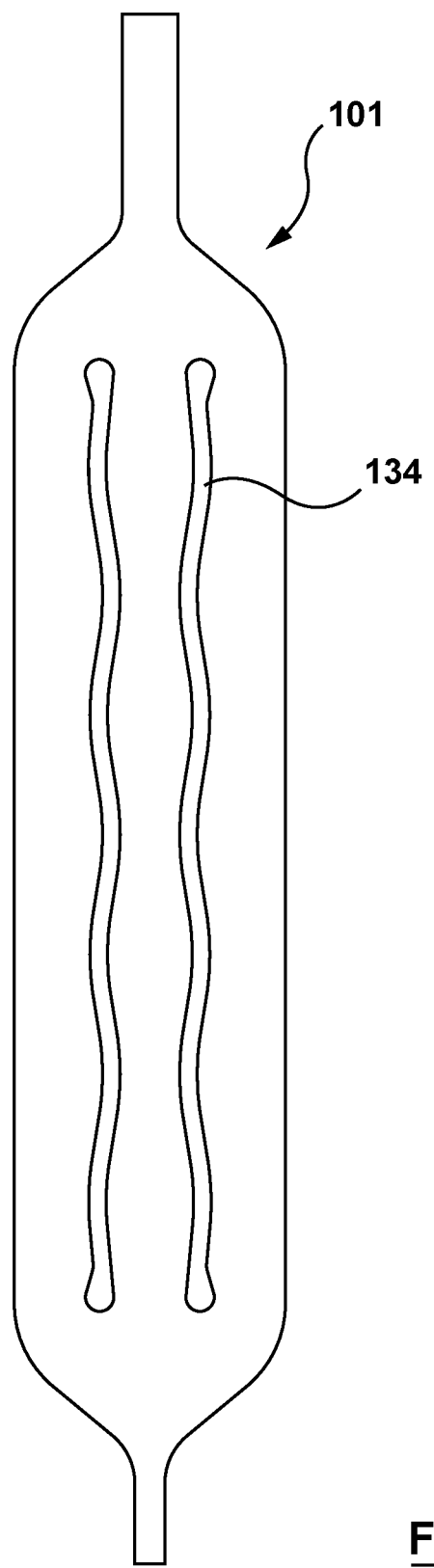
FIG. 39 is an illustration of a further embodiment of a balloon with a pair of wavy weld lines.
Figure 40:
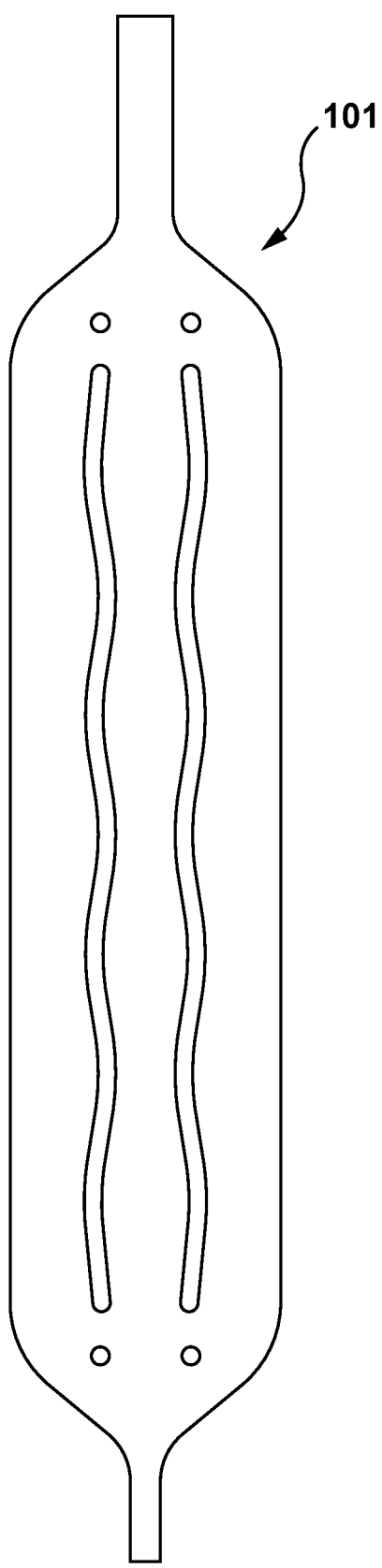
FIG. 40 is an illustration of a balloon with a pair of wavy weld lines and multiple tack welds.
Figure 41:
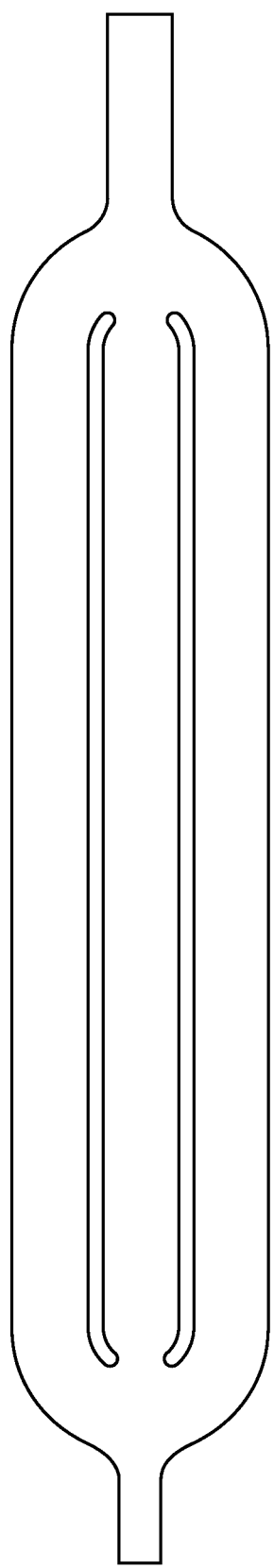
FIG. 41 is an illustration of a balloon with a pair of curved weld lines.

The balloon heat exchanger 101 of FIG. 27 includes a balloon with a weld line 111 creating two fluid flow channels. FIGS. 38, 39, and 40 includes a balloon 101 with two wavy welds creating three fluid flow channels—the wavy welds in these embodiments creates multiple hinge axis, and each axis resists hinge-like behavior giving the balloon added widthwise rigidity when the balloon is inflated, which may be desirable in certain applications. FIG. 41 includes a balloon 101 with two weld lines which are curved at their end. The curved ends correspond with an outer contour of the balloon. By providing these curves, the cross-sectional area at the ends of the balloon 101 are somewhat reduced, thereby reducing the stress on the material when inflated. The embodiments in FIGS. 27, 38, 39, 40, and 41 each create multiple fluid channels along the length of the balloon such that fluid which is introduced at one end (e.g., the distal end) may naturally flow through the channels towards the other end (e.g., the proximal end). Continuous fluid flow through the length of the balloon enables more efficient heat exchange as the target area is continuously provided with heated or cooled fluids.

FIGS. 43, 44, 45, and 46 illustrate balloons with broken line welds. This design enables the mixing of fluid flow between the lengthwise fluid channels, which may be desirable in applications where the fluid in a particular channel is being cooled or heated more than the fluid in the other lumens. These fluid channels are "open" such that fluid from one lengthwise channel may flow to a different lengthwise channel, the balloon may provide more even heat exchange to an area of the esophagus that is experiencing the most extreme temperatures. It also allows the balloon to be more easily inflated within the esophagus because there are multiple pathways for fluid to flow into a given area of the balloon.

Figure 47:
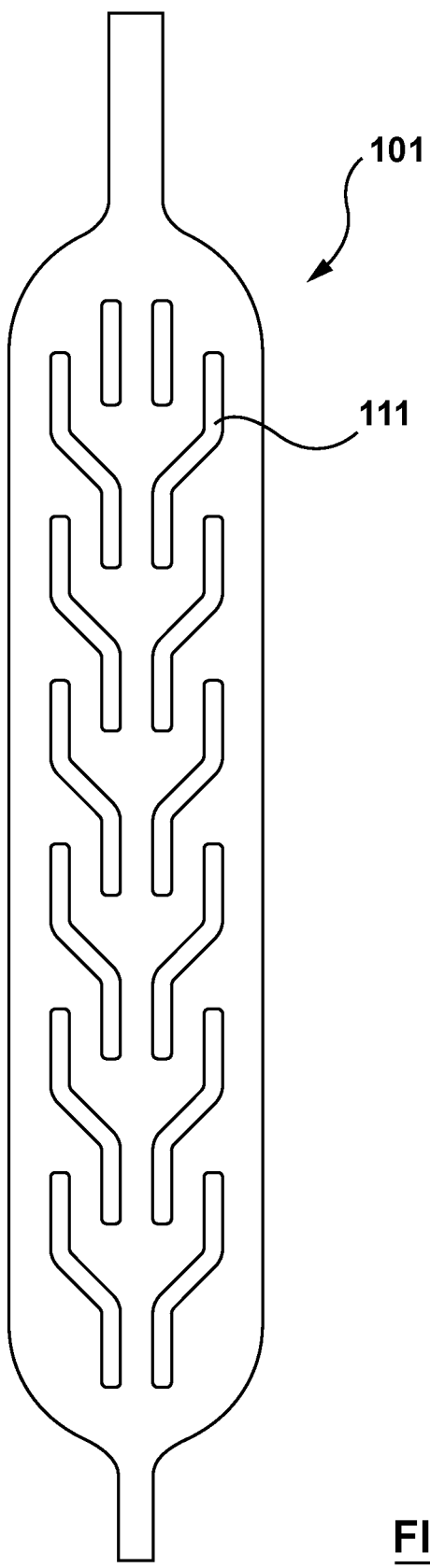
FIG. 47 is an illustration of a balloon with chevron pattern welds.
Figure 48:
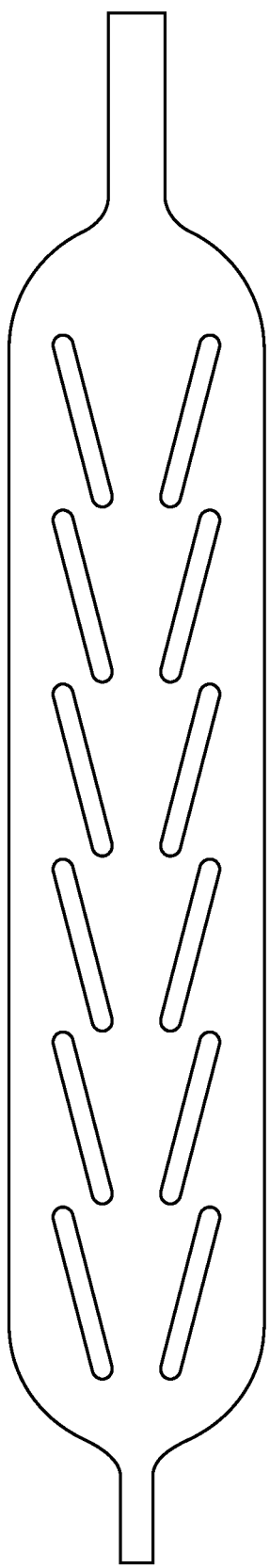
FIG. 48 is an illustration of a further embodiment of a balloon with chevron pattern welds.
Figure 49:
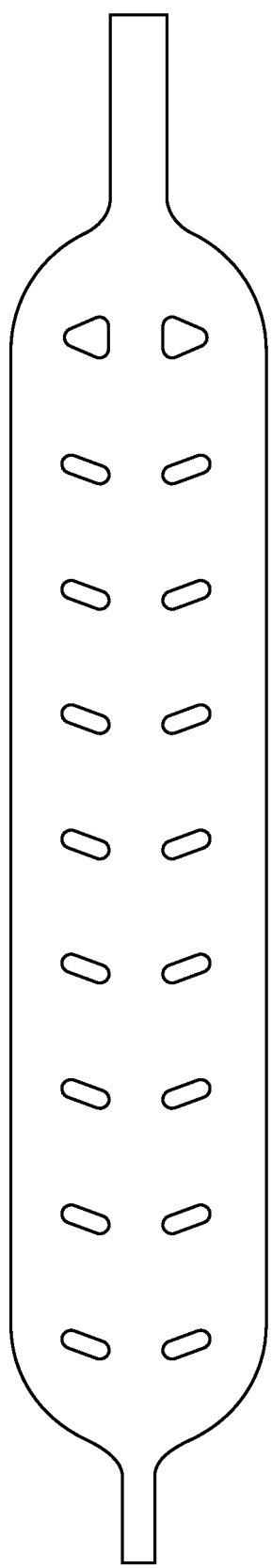
FIG. 49 is an illustration of yet another embodiment of a balloon with chevron pattern welds.
Figure 50:
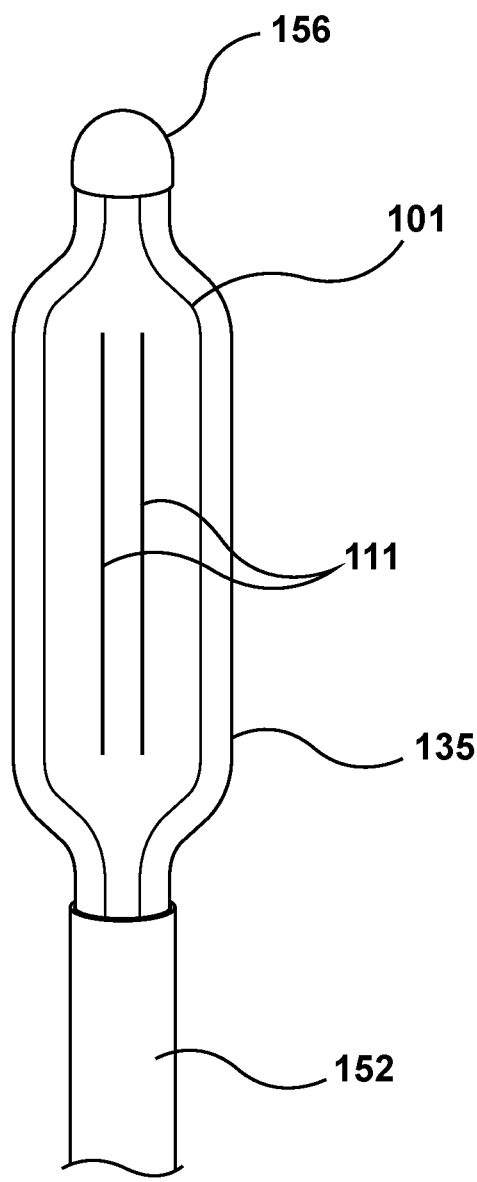
FIG. 50 is an illustration of a welded balloon with an outer balloon.

FIGS. 47, 48, and 49 illustrate balloons with a chevron pattern. This pattern allows fluid flow mixing across the fluid flow channels. The diagonal alignment of the welds increases widthwise rigidity which allows the balloon to be more easily deployed and inflated after being introduced into the esophagus in applications where the balloon is introduced into the esophagus deflated and wrapped around a central shaft along the balloon's lengthwise axis.

Figure 30:
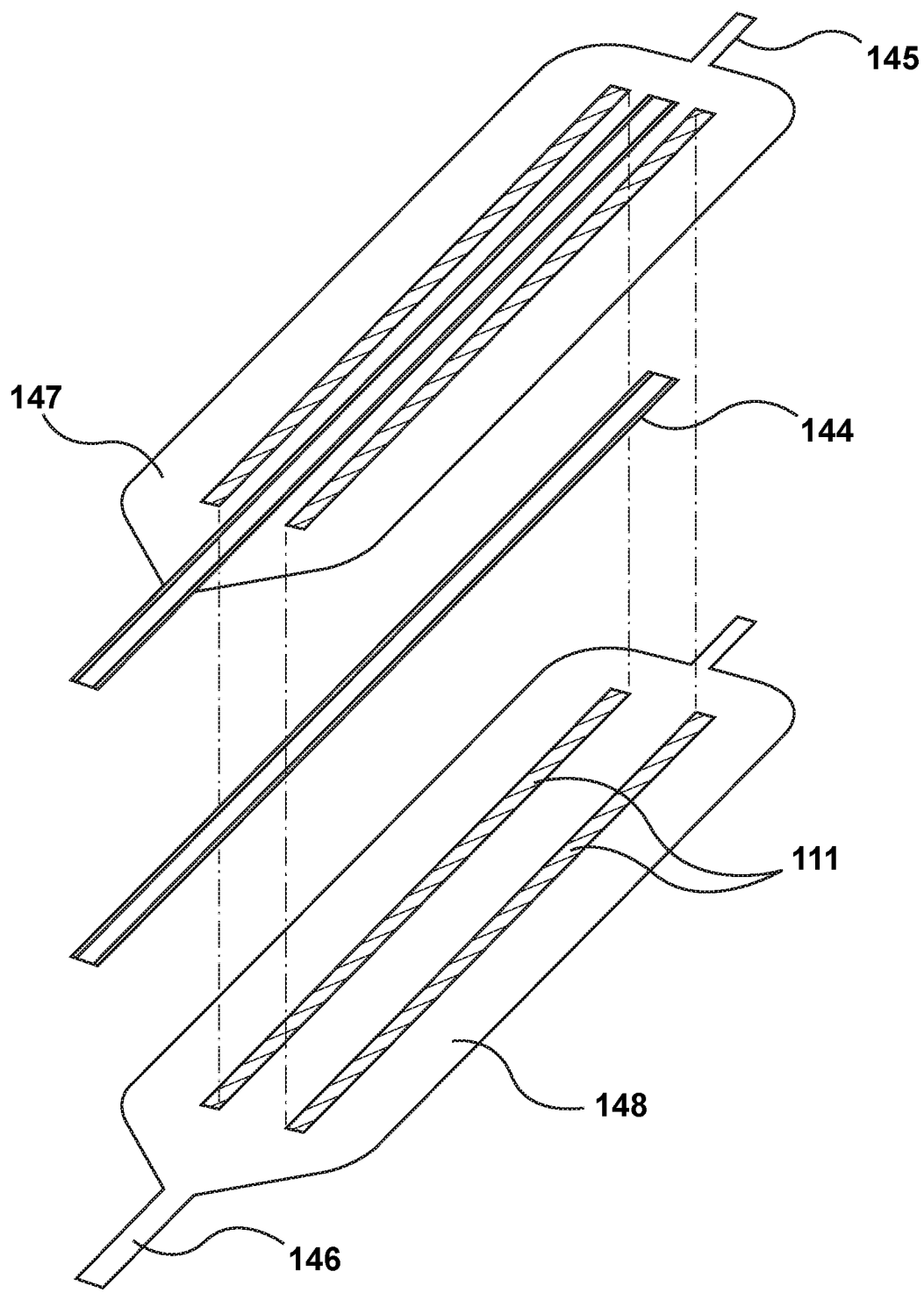
FIG. 30 is an exploded view of a balloon.
Figure 54:
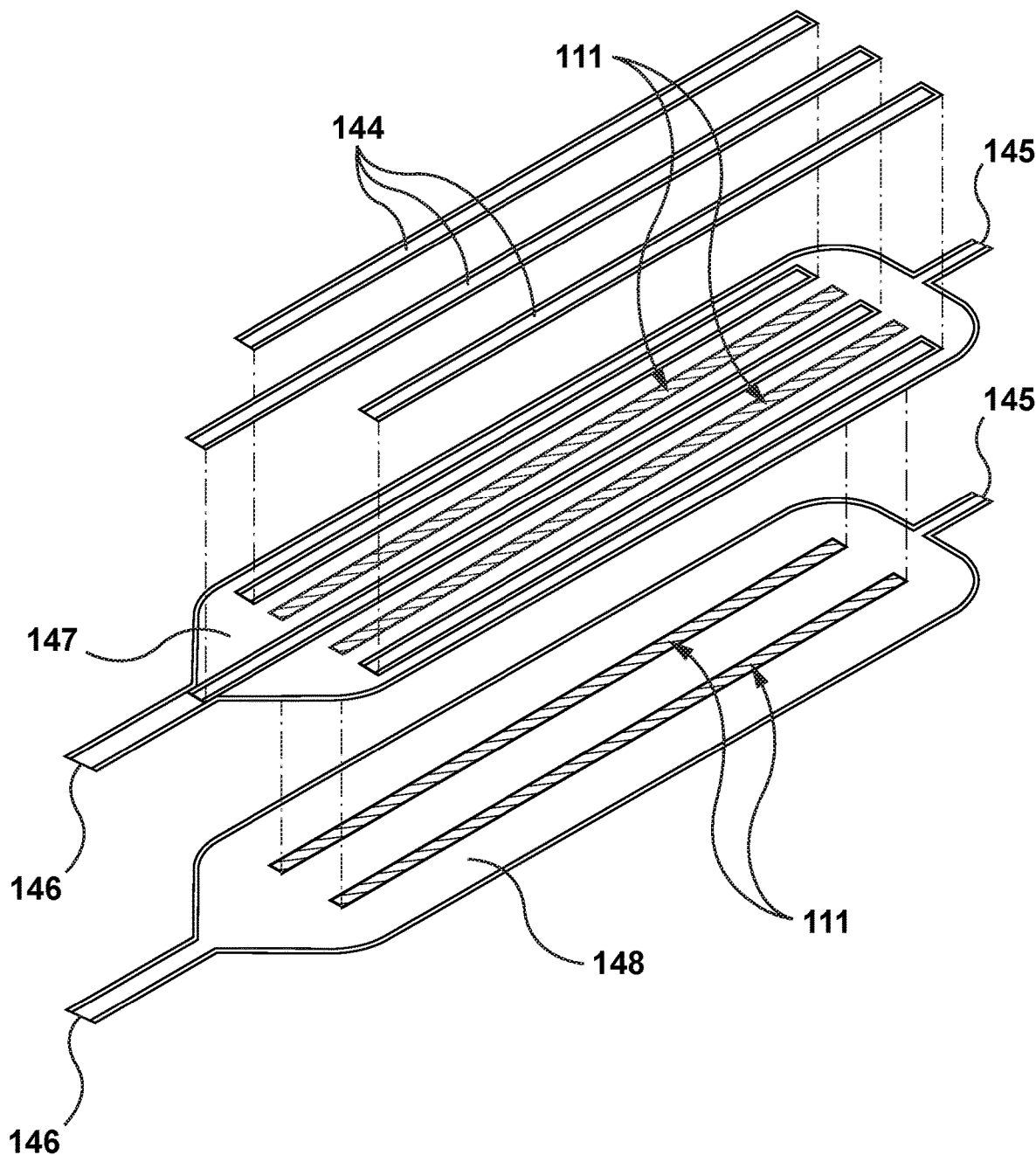
FIG. 54 is an exploded view of a an embodiment.
Figure 55:
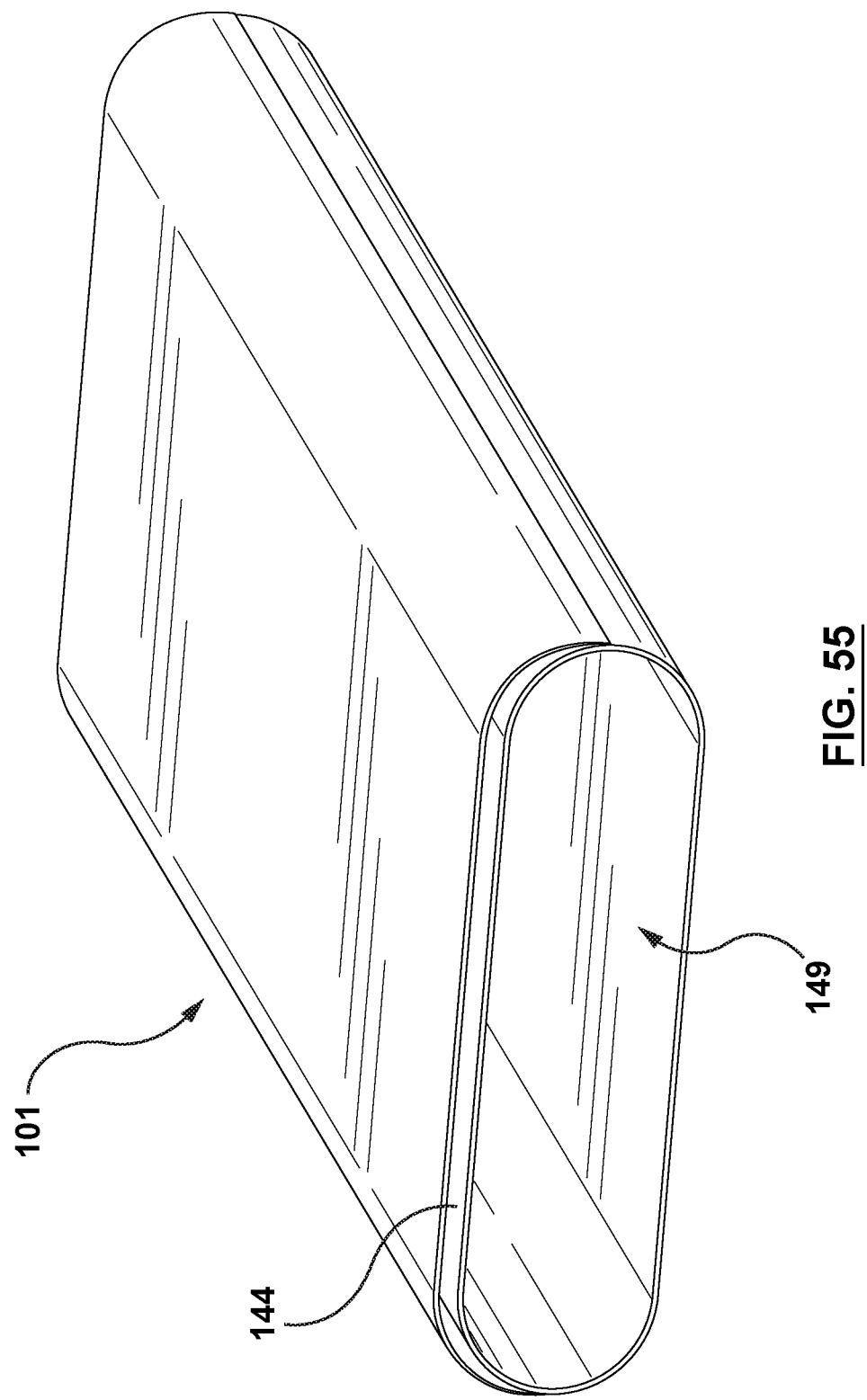
FIG. 55 is an illustration of a heat exchanger comprising a pocket.

FIG. 30 is an exploded view of a balloon 101 before welding. In this embodiment, a pocket 144 is welded in between an anterior balloon surface 147 and a posterior balloon surface 148. This embodiment of balloon 101 further comprises a distal neck portion 145 and a proximal neck portion 146. Pocket 144 may comprise temperature sensors, heat flux sensors, force sensors, or other sensors (not shown). FIG. 54 is an exploded view of a further embodiment of balloon 101 before welding. In this embodiment, three pockets 144 are welded to the outer surface of the anterior balloon surface 147 (i.e., the surface closest to the target area), allowing various sensors to be spread across the width of the balloon. Weld lines 111 are provided creating three fluid flow channels. Pockets 144 are positioned along the fluid flow channels. Positioning pockets 144 on the outer surface of the balloon also allows the sensors to be closer to the target area. Other orientations and combinations of pockets may also be provided. In yet a further embodiment, FIG. 55 depicts a heat exchanger 101 comprising a pocket 144. Pocket 144 may be formed by attaching a piece of material on the outside of the heat exchanger 101, thereby creating a pocket 144 adjacent to lumen 149.

Some alternative embodiments of the heat exchanger 101 have fins or fingers that expand to the desired shape once inflated. The example of FIG. 10 includes a welded balloon with fins 113.

Figure 11:
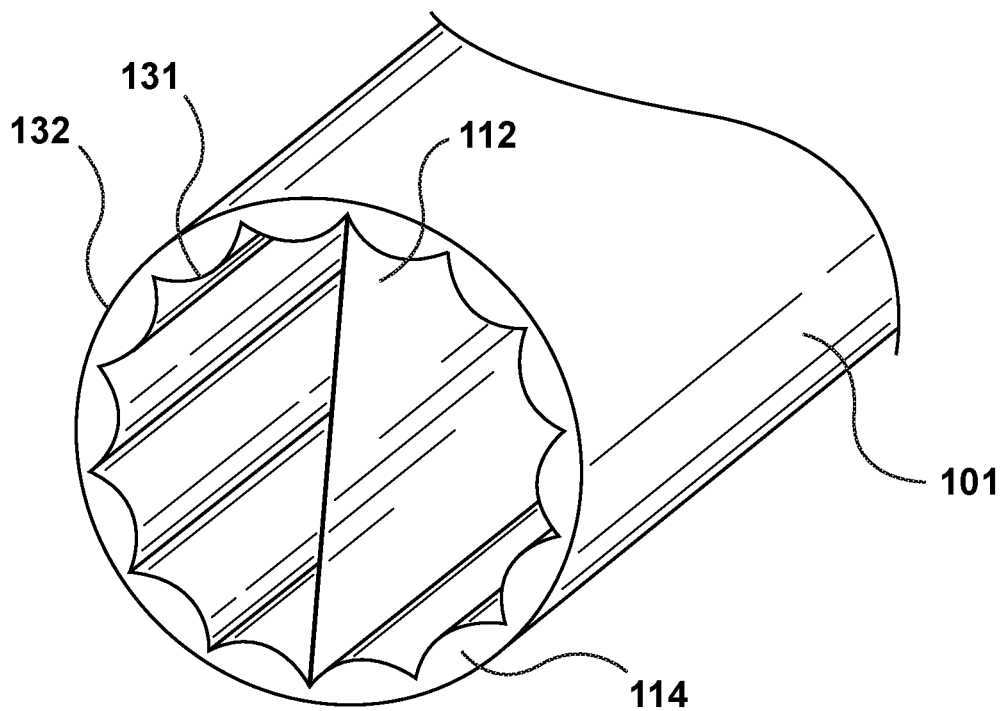
FIG. 11 is an illustration of a welded balloon with pockets.

In other embodiments, multiple pockets are welded along the balloon and brought together with ties to hold the balloon in the desired shape. The FIG. 11 embodiment of balloon heat exchanger 101 comprises an inner film 131, an outer film 132, and a tie 112. The inner film 131 and outer film 132 are welded together to form a series of longitudinal pockets 114 (that is, along the length of the balloon). Fluid flows through the longitudinal pockets in order to perform heat exchange. Tie 112 is attached between two sides of an inner diameter of the balloon heat exchanger 101 to produce a desired cross-sectional shape. In FIG. 11, the cross-sectional shape of the balloon heat exchanger is circular. As previously mentioned, the balloon heat exchanger is more preferably oblong to better conform to the cross-sectional area of the collapsed esophagus and reduce the resulting displacement of the esophagus. The length and position of tie 112 may be adjusted to change the shape of the balloon heat exchanger when it is in its inflated or expanded configuration.

In addition to using welding to construct balloon heat exchangers, other means known to those skilled in the art may also be used. For example, other adhesive techniques or blow molding techniques may be employed.

In the embodiments where the outer edges of the balloon are welded, sometimes the outer edges may become sharp. In such cases, an outer balloon 135 without any sharp edges may be provided and covers the inner welded balloon 101 (see FIG. 50). To avoid air or other fluids to be trapped between the inner balloon and the outer balloon 135, the outer balloon may be perforated or may be vacuum sealed against the inner balloon. The outer balloon may be constructed by flipping a welded balloon inside-out, blow molding, or other techniques known to those skilled in the art. A blunt tip 156 may be provided to prevent damage to the body lumen. In the embodiment shown in FIG. 50, a sheath 152 is also provided for receiving the heat exchanger 101.

In another embodiment, the outer edges of the welded balloon may comprise small cuts along the outer edge. By introducing small cuts along the outer edge, the rigid outer edge is rendered soft, and reduces the likelihood of damage to the esophagus while the balloon is being introduced through the esophagus. Other techniques may be used to blunt or soften the outer edge, including:

The outer edge may be widened such that the welded outer edge is softened.

The outer edge may be folded over and welded, glued, or bonded to create a rounded outer edge.

The outer edge may be melted to blunt the outer edge.

Other materials (sprays or dips) may be added to blunt the outer edge.

Figure 35:
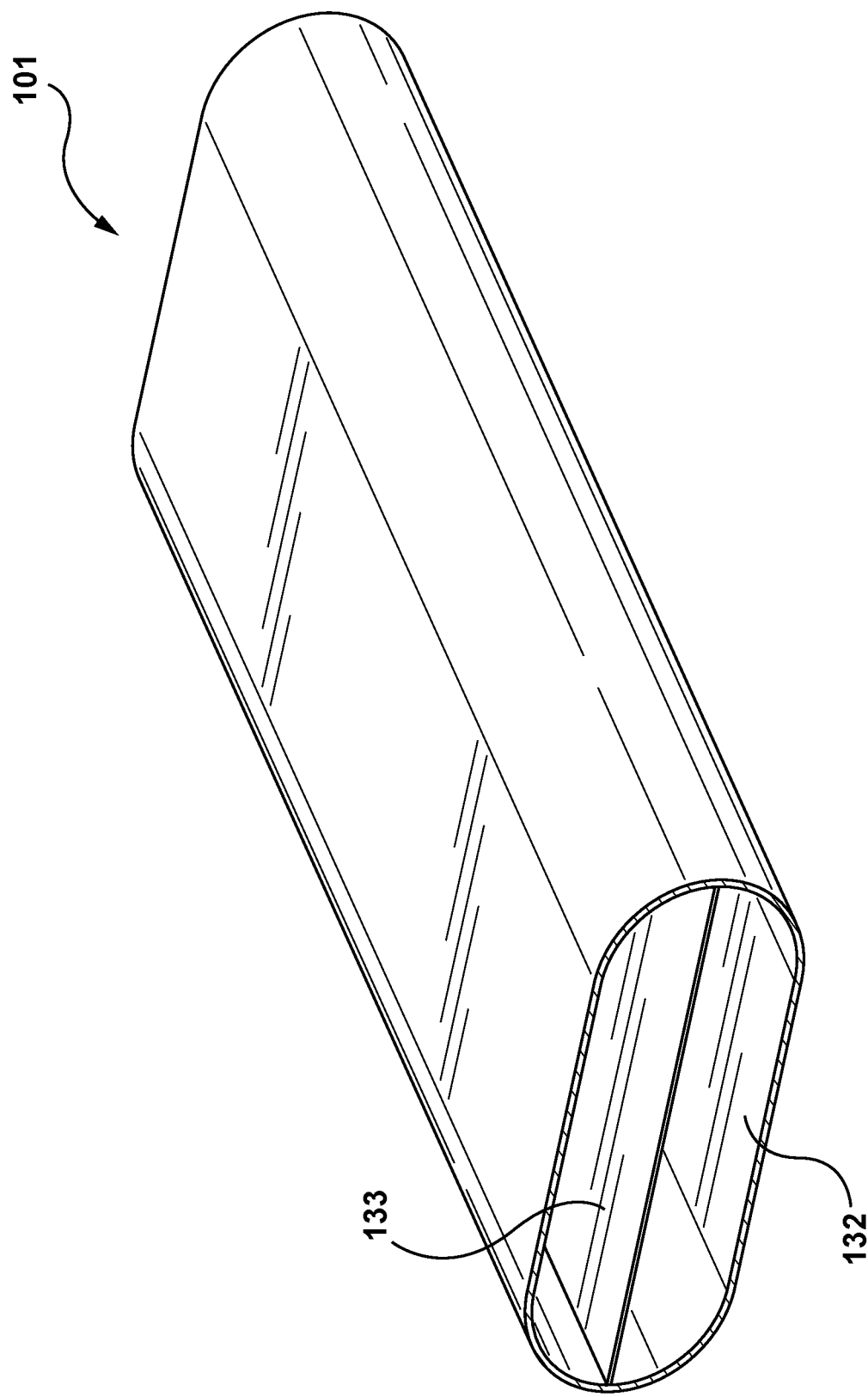
FIG. 35 is an illustration of a heat exchanger with a shaping lumen and a heat exchanging lumen.

FIG. 35 illustrates a further embodiment of a balloon heat exchanger 101. In this embodiment, the balloon 101 comprises a shaping lumen 132 and a heat exchanging lumen 133. The shaping lumen 132 and heat exchanging lumen 133 are isolated from one another such that fluid in one lumen does not flow to or from the other. In operation, fluid flows through the heat exchanging lumen 133. The temperature and flow rate of the fluid may be varied to change the rate at which heat is being exchanged between the heat exchanger 101 and the surrounding environment (i.e., the tissue in the esophagus when the heat exchanger 101 is inserted therein). In this embodiment, balloon 101 further comprises a shaping lumen 132. Shaping lumen 132 may be supplied with a separate fluid (e.g., air or water) which inflates the shaping lumen 132 to its inflated form. Unlike the heat exchanging lumen 133, fluid need not flow through the shaping lumen 132 in order for the shaping lumen 132 to perform its function. Once inflated, it is possible to maintain the shape of the shaping lumen 132 without providing any fluid flow. Thus, the shape of balloon 101 may be controlled independently from the fluid flow rate and pressure inside the heat exchanging lumen 133. Those skilled in the art will appreciate that this allows greater flexibility in varying the parameters to arrive at an appropriate rate of heat exchange.

Tubular Heat Exchanger

In another embodiment of the heat exchanger, the cavity for circulation of fluid is an arrangement of thermally conductive tubes. The tubes are preferably arranged to fill a cross-sectional area with outside dimensions similar to the collapsed state of a human esophagus.

Figure 12:
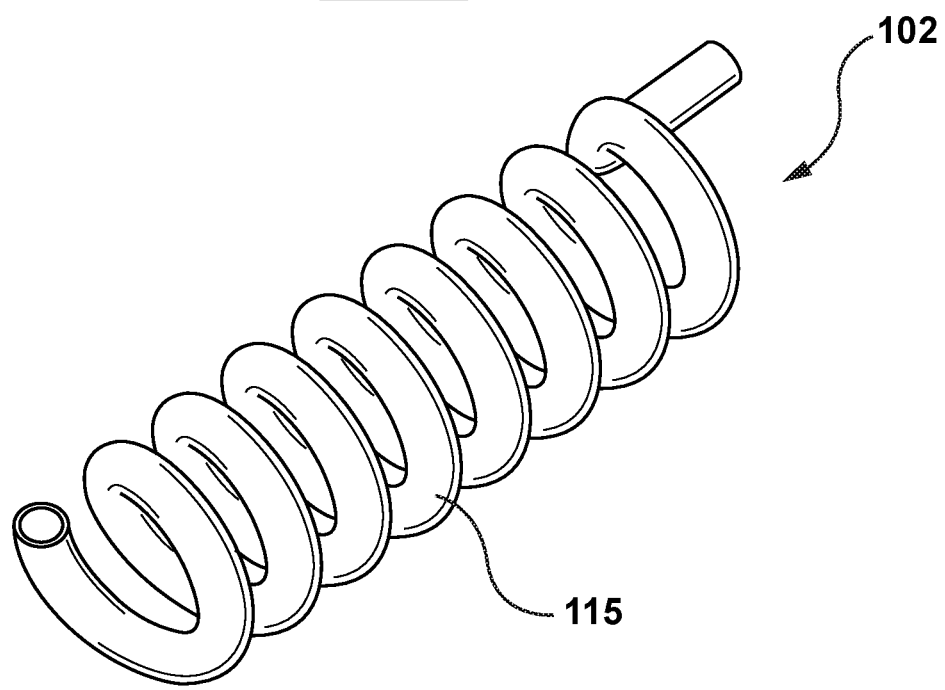
FIG. 12 is an illustration of a coiled tube heat exchanger.

In some embodiments, the tubes are arranged in coils. FIG. 12 illustrates a tubular heat exchanger 102 having coils 115. The profile of the tubular heat exchanger 102 of FIG. 12 is circular.

Figure 13:
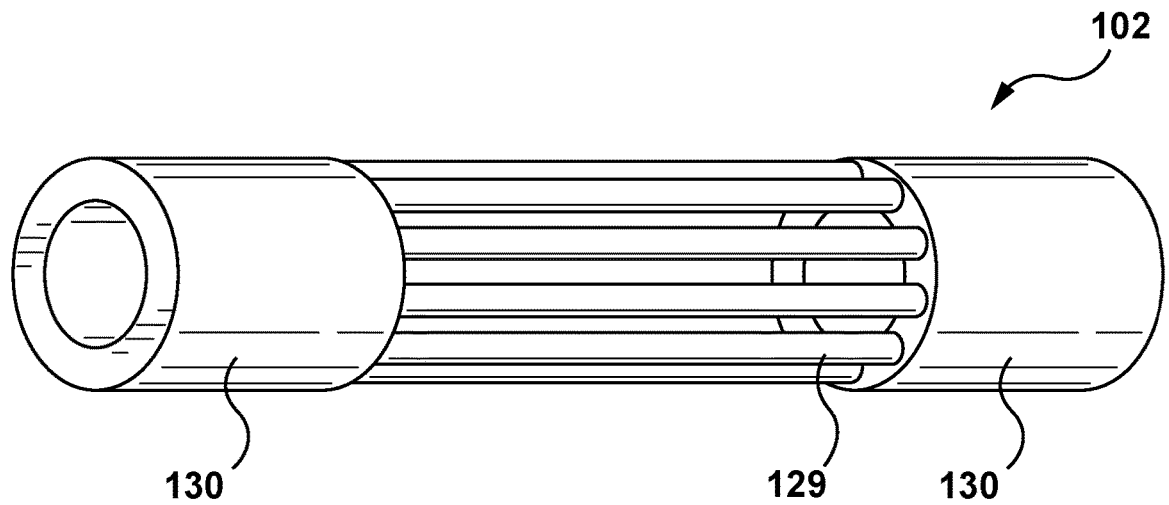
FIG. 13 is an illustration of a multiple-tube heat exchanger.

In some embodiments, the tubes are arranged in parallel and in a circular orientation, such as in the example of tubular heat exchanger 102 FIG. 13. The tubular heat exchanger 102 of FIG. 12 includes a number of exposed tubes 129 while alternative embodiments may include separate lumens in a single tube (not shown).

Figure 14:
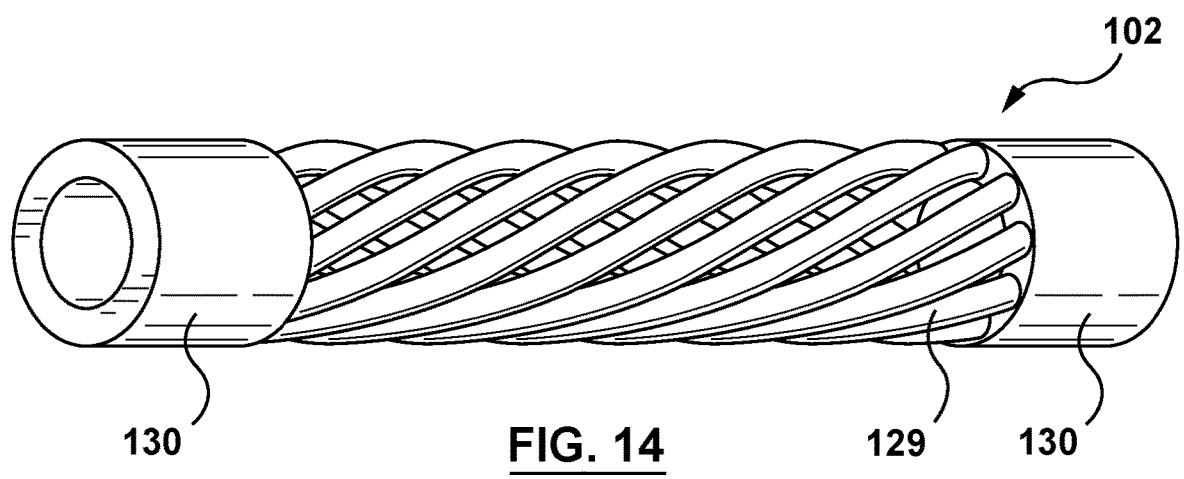
FIG. 14 is an illustration of a helical-tube heat exchanger.

In some embodiments, the tubes 129 are arranged in a helix (e.g. FIG. 14. Helical-tube heat exchanger). In FIG. 14, each tube 129 is spiral-shaped and is helically arranged adjacent to other spiral-shaped tubes. In the embodiments shown in FIGS. 13 and 14, heat exchanger 102 further comprise a pair of end portions 130. Each of the tubes 129 are fixed between the two end portions 130 to maintain the relative orientation between the tubes.

Figure 31:
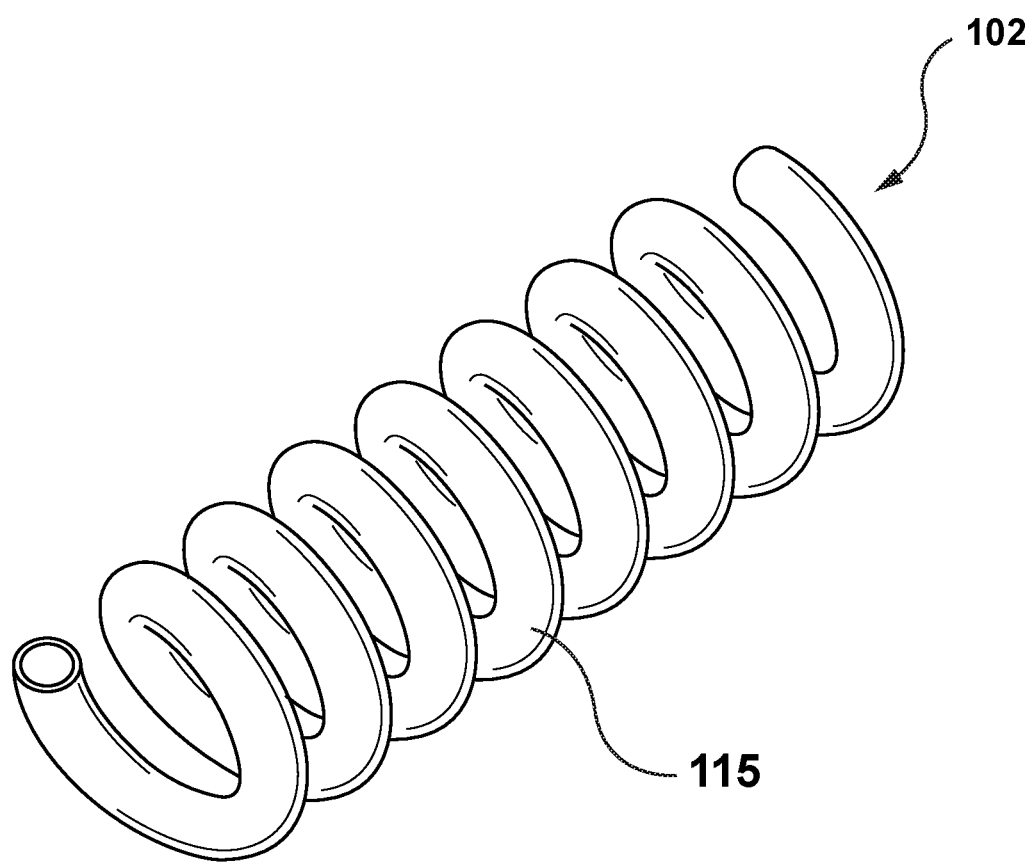
FIG. 31 is an illustration of a coiled tube heat exchanger with an oblong cross-sectional profile.
Figure 32:
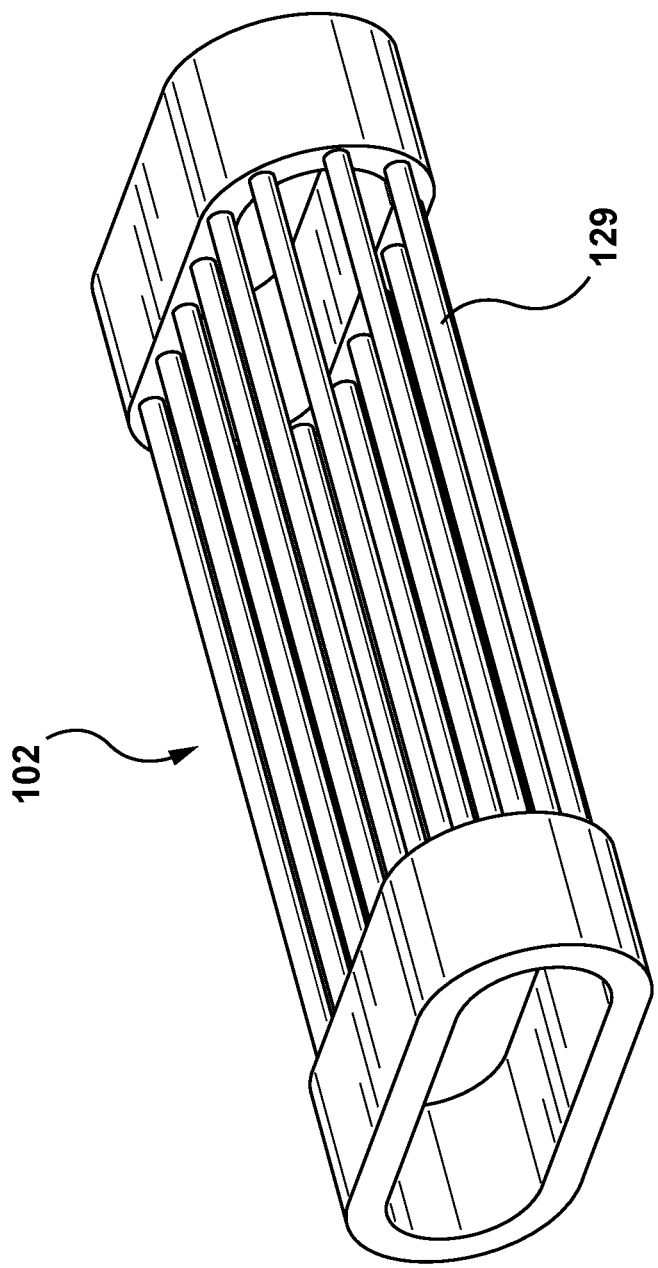
FIG. 32 is an illustration of a multiple-tube heat exchanger with an oblong cross-sectional profile.
Figure 33:
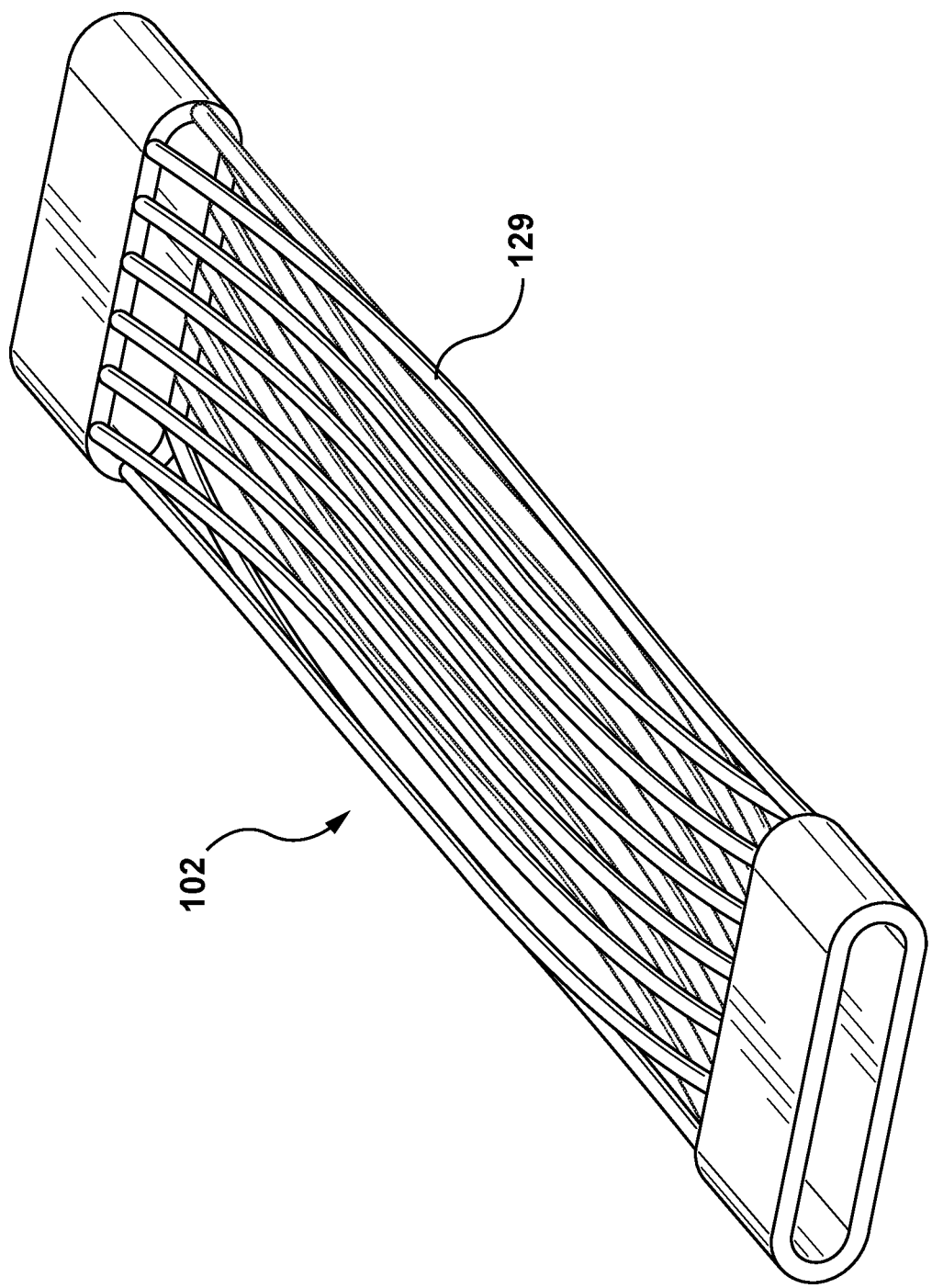
FIG. 33 is an illustration of a helical-tube heat exchanger with an oblong cross-sectional profile.

Each of the embodiments illustrated in FIGS. 12, 13, and 14 comprise a circular cross-sectional profile. More preferably, the cross-sectional profile of the heat exchanger 102 is oblong to better conform to the cross-sectional area of the inside of a collapsed human esophagus. Examples of such embodiments are illustrated in FIGS. 31, 32, and 33.

Figure 15:
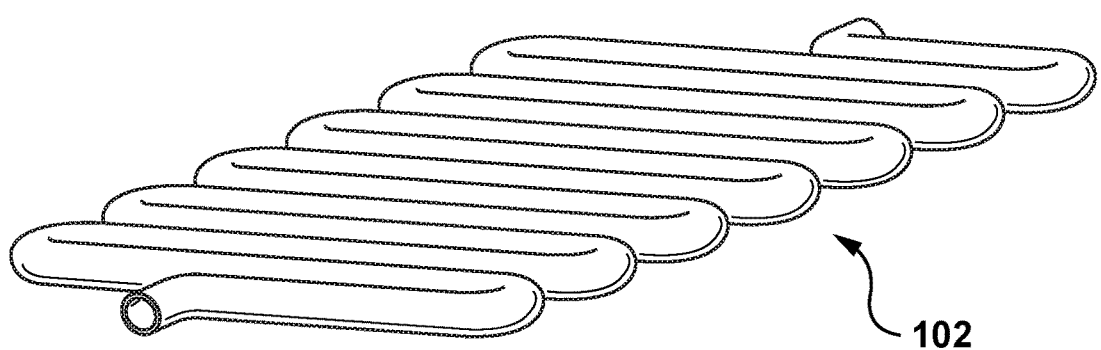
FIG. 15 is an illustration of a serpentine-tube heat exchanger.

Some alternative embodiments have a serpentine-shaped tube, such as shown in FIG. 15.

Typically, the surface of the heat exchanger is thermally conductive to facilitate the transfer of heat at the desired treatment zone. In some examples, the surface is a film substantially thin enough to allow transfer of thermal energy, e.g. with a thickness between around 0.001" to around 0.003". In some alternate embodiments, the surface is made of a thermally conductive material, such as metal foil.

To further promote heat exchange, a thermally conductive gel or coating may be applied to the heat exchanger, or to the target tissue site. This may fill any gaps that might exist between the tissue and the heat exchanger.

Method of Using the Heat Exchanging Fluid Device

A method of regulating a temperature of an esophagus when heat or cold is delivered to a left atrium (FIG. 26) includes the steps of:
  (1) measuring the esophagus and selecting a size of a heat exchange device which fits the esophagus;
  (2) delivering the heat exchange device to a target site;
  (3) confirming a desired location of the heat exchange device;
  (4) exchanging heat with the esophagus;
  (5) confirming that the target site is protected; and
  (6) retrieving the heat exchange device.

The steps of the method are described in more detail herein below.

Step 1: Measuring the Esophagus and Selecting a Size of a Heat Exchange Device which Fits the Esophagus The esophagus is measured in order to select the appropriate device size for the patient. Ways of doing this include:
  (a) Using an internal measurement device. One example is a device that expands until optimal force, impedance, or another parameter indicative of size is measured by the device. Another technique is inserting a series of devices of different sizes into the esophagus until adequate force, impedance, or other parameter is measured by the device.
  (b) Using imaging, such as fluoroscopy, CT, MRI, EAM, etc. Measurements of the anatomy can be taken using methods known to those skilled in these areas of imaging.
  (c) Using a combination of internal measurement devices and imaging. For example, inserting devices of different sizes into the esophagus and viewing them with an imaging modality to determine proper fit. Another technique is inserting an internal ruler device into the esophagus and taking measurements with the imaging system.
  (d) Estimating the size of the esophagus based on external anatomical features.

Once the esophagus size is known, the heat exchange device of best fit can be chosen from a selection of devices that cover the range of most anatomical variations.

Step 2: Delivering the Heat Exchange Device to a Target Site

Delivering the heat exchange device to the target site in the esophagus includes inserting it through a small orifice such as the mouth or nostril, and then advancing the heat exchange device through tortuous path defined by the esophagus until the heat exchange device is positioned at the posterior aspect of the left atrium. A number of features enable the heat exchange device to enter a small orifice.

The heat exchanger may be collapsible, foldable, and wrappable such that it can be delivered through a substantially round hole with a diameter of about 0.2 cm to about 0.6 cm. In one embodiment, the heat exchanger is a balloon that can be deflated and wrapped or folded around a main shaft such that it can be delivered to the desired treatment area through a small orifice. Some embodiments of the heat exchange device 100 have an outer diameter equal to or less than 18 F.

In an alternate embodiment, the heat exchanger is made of tubes that can be twisted, pulled, or otherwise re-arranged such that they maintain an outer diameter in the desired range and be delivered through a small orifice. Alternately, the tubes themselves may collapse when they are evacuated.

Figure 20:
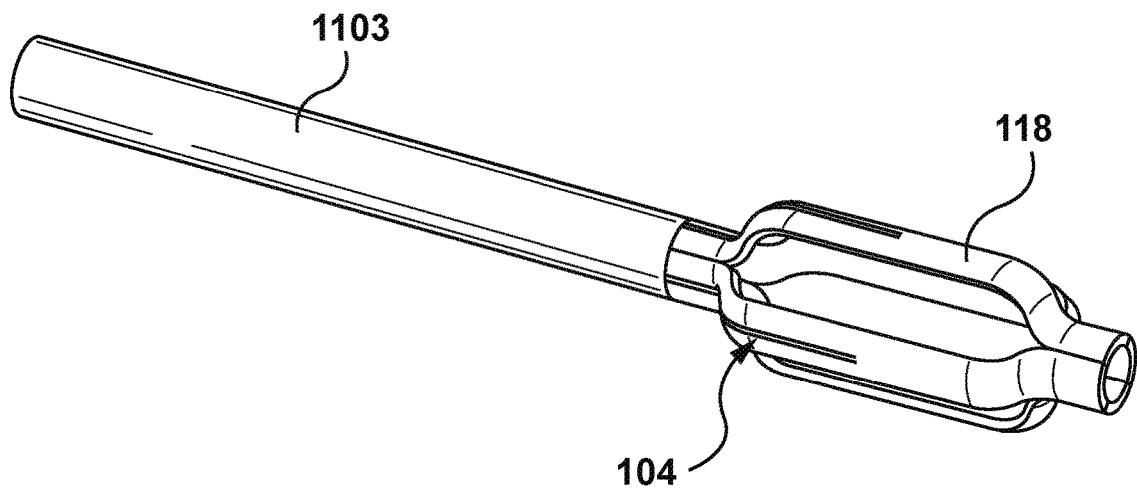
FIG. 20 is an illustration of temperature sensors mounted on struts made from a catheter shaft

Alternately, the heat exchange device could have a folding or collapsing metal structure such as a stent-like configuration (see FIG. 20).

The delivery orifice may be an access point on the patient, such as the nasal or oral passageway. Alternately, the delivery orifice may be a delivery tube. Once collapsed, the heat exchanger can be loaded inside the delivery tube, and the delivery tube delivered through an access point on the patient. Typical embodiments of the heat exchange balloon may be tapered at the ends to promote gradual dilation of the small orifice. Once in the desired treatment area, the heat exchanger (the balloon) can then be advanced to exit the tube. Alternately, instead of advancing the heat exchanger (the balloon) out of the delivery tube, the delivery tube could be retracted to expose the heat exchanger.

In addition to the above features, the delivery of the heat exchange device may be augmented by the addition of a lubricious coating on the outside surface of the heat exchange device or on the inner surface of the small orifice.

In order to advance the heat exchange device along a tortuous path, the flexibility of the device may be modifiable with a selection of features:
  (a) varying stiffness along the body of the device, and
  (b) bend points built into the device. For example, instead of a singular heat exchange balloon there may be a number of heat exchange balloon in series along the body of the device, with bend points between them. Alternately, there may be spring-like joints or bendy-straw style joints at desired bend points along the body of the device.

To overcome the difficulty of navigating a flexible device along a tortuous path, the heat exchange and temperature sensing device may have a selection of features:
  (a) steerable portions,
  (b) weighted portions, and/or
  (c) a stylet that may be removable. The stylet may be super-elastic, have a shape-set memory, may be steerable, or may change the shape of the heat exchange device as it is advanced and retracted within.

To avoid mechanical injury to tissue, the heat exchange device may have features to promote atraumatic delivery. These features may include floppy portions, tapered ends, soft portions, steerable portions, and a soft covering sheath.

If the heat exchange device is collapsed/folded/wrapped, it must be expanded once it reaches the target location of the esophagus. The heat exchange device may be expanded in a number of ways:
  (a) Expanded with pressure, such as with a balloon or tubes inflated with heat exchange fluid. In some embodiments, the device may operate at more than one pressure. For example, fluid provided at a first higher pressure may be used to expand or inflate the balloon or tube. Once the balloon or tubes have been expanded, the heat exchange device may operate at a lower pressure so that the balloon or tubes are less rigid. A balloon or tubes which are less rigid are more likely to make good contact with the esophagus while minimizing displacement of the esophagus.

(b) Expanded with shape memory. The heat exchange device may employ shape memory metals or polymers that may be expanded into the desired shape through thermal or electrical activation.

(c) Expanded with a mechanical mechanism, such as with a stent-like configuration.

(d) With any of these expansion methods, the heat exchange device may expand to perforate a delivery sheath that was holding the folded/collapsed/wrapped portions within.

Step 3: Confirming a Desired Location of the Heat Exchange Device

Once the heat exchange device has been delivered to the target site and expanded (if required) the user confirms that the device is in the correct location. This may be achieved by a number of means:

(a) Device visualization relative to known anatomical markers. This can be achieved by having markers on the device, such as a ruler on the device body, orientation markers on the device body or handle, electrodes visible on an EAM system, or radiopaque markers on the device body (see item 153 in FIG. 29), handle or stylet visible on fluoroscopy. Visualization of markers can be used to confirm the position and orientation of heat exchange device 100. Markers are located on the heat exchange device such that they do not interfere with the desired use of the device, for example, located on the posterior aspect of the heat exchanger.

(b) Measurement of a physiological parameter. Some embodiments of the heat exchange device are capable of measuring a physiological parameter indicative of location in the body through the use of sensors or electrodes. Examples of the parameter which may be measured include ECG, tissue impedance, temperature, blood perfusion rate, oxygen saturation, and others.

Step 4: Exchanging Heat with the Esophagus

Option 1: Using a Heat Exchanging Fluid Device

As discussed above, heat may be exchanged within the esophagus using a heat exchange fluid device, such as those embodiments described above in the section titled "Heat Exchange Fluid Device". In one embodiment, the fluid used in the device is comprised substantially of water. For example, the fluid may be distilled water or saline. Alternatively, the fluid may be a substance that is not substantially water, such as an oil based or petroleum product. In addition, the fluid may contain additives, for example a disinfectant, or stabilizer. The temperature, flow rate, and pressure of the fluid is managed through an external controller which includes a pump.

In operation, fluid flows through an inlet port into the heat exchanger of the heat exchanging fluid device and circulates through the body of the heat exchanger. An outlet port is also provided to allow fluid to flow out of the heat exchanger. Fluid may continuously flow through the heat exchanger so that there is continuous heat exchange with the esophagus.

Option 2 for Exchanging Heat: Open Irrigation

Figure 25:
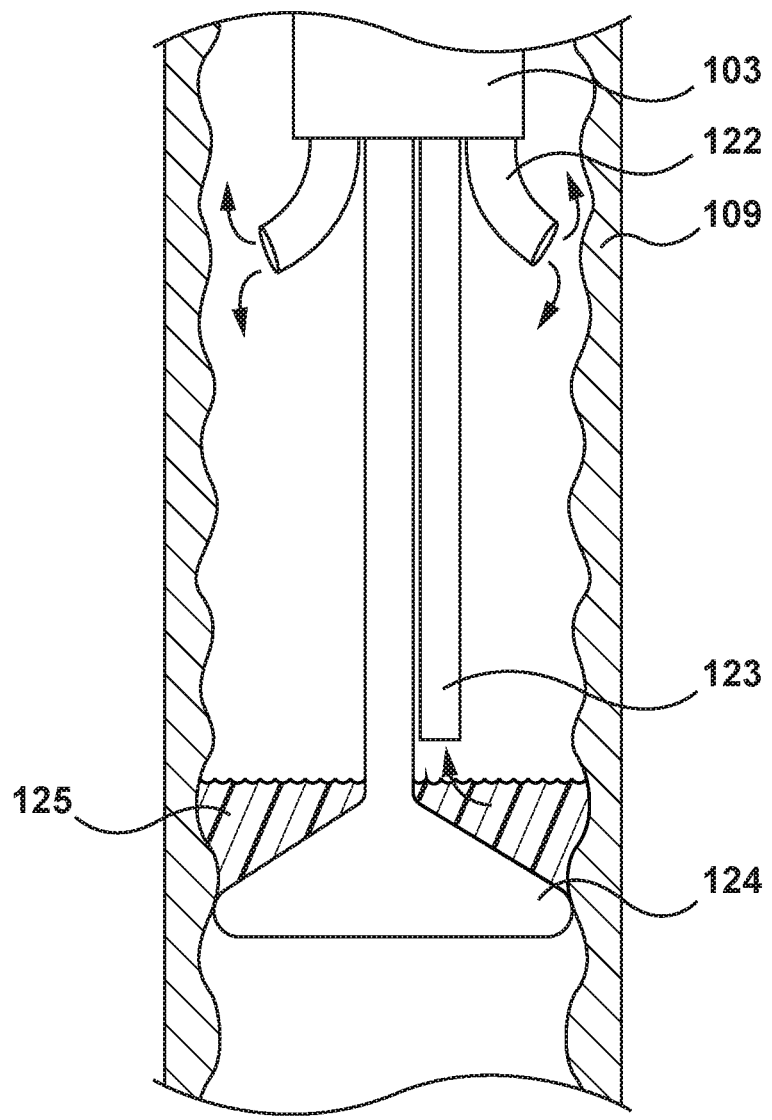
FIG. 25 is an illustration of open irrigation of a fluid with suction.
Figure 26:
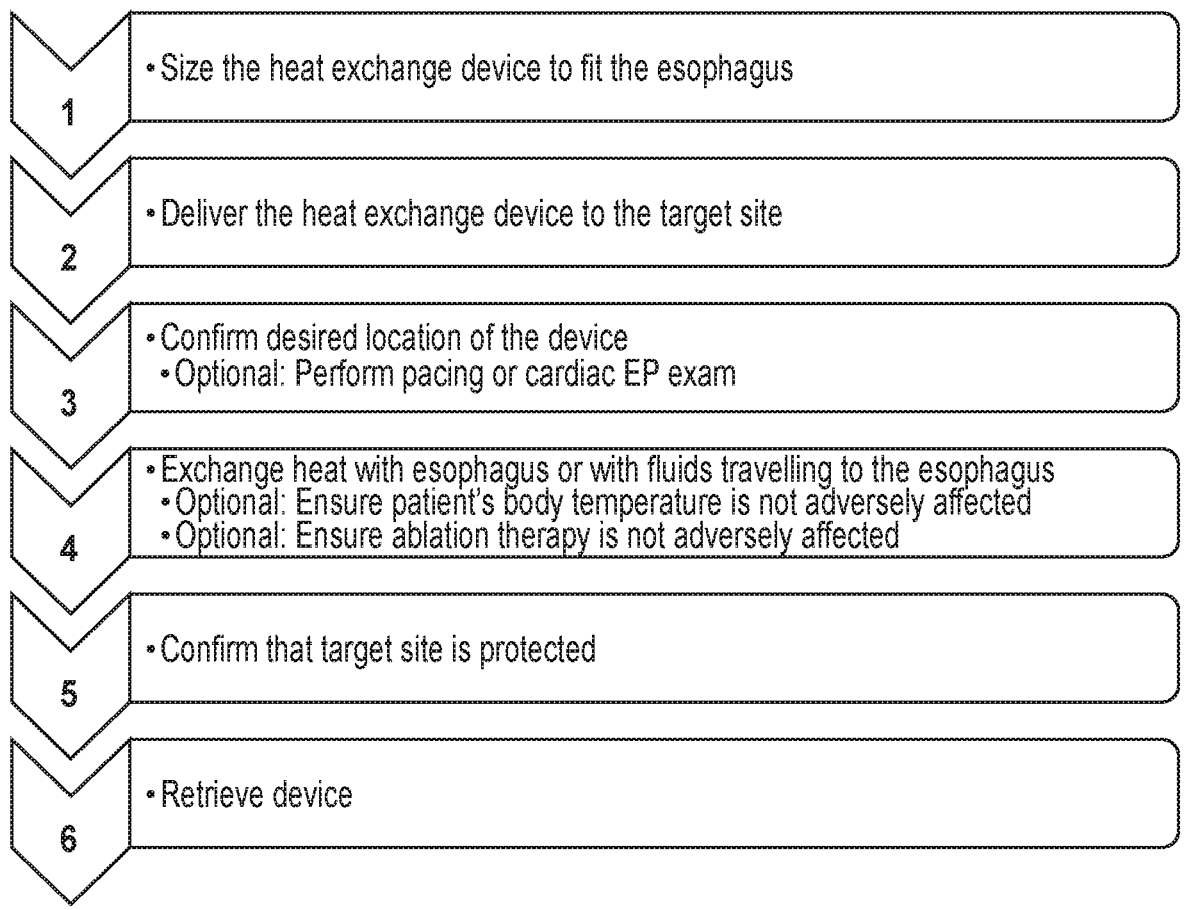
FIG. 26 is a flowchart of a method.

In an alternate embodiment (e.g. FIG. 25 open irrigation of fluid with suction), the heat exchange fluid 125 is delivered directly to the desired treatment zone in an open-irrigated system. In one embodiment, the heat exchange device 100 is connected to an external controller that provides the heat exchange fluid 125. The fluid is delivered through a fluid spray tube 122 and sprayed circumferentially toward the endoluminal surface of the esophagus. Fluid is removed using fluid suction tube 123. In typical embodiments, the tube has multiple holes along its length and around its circumference in order to deliver an even spray of fluid to the desired treatment zone. In one embodiment, the fluid is allowed to travel through the esophagus to the stomach. Alternately, in some embodiments, the esophagus is blocked by an esophageal blocking balloon 124, and the fluid is collected cranial to the blocking balloon 124 and suctioned from the esophagus.

Figure 51:
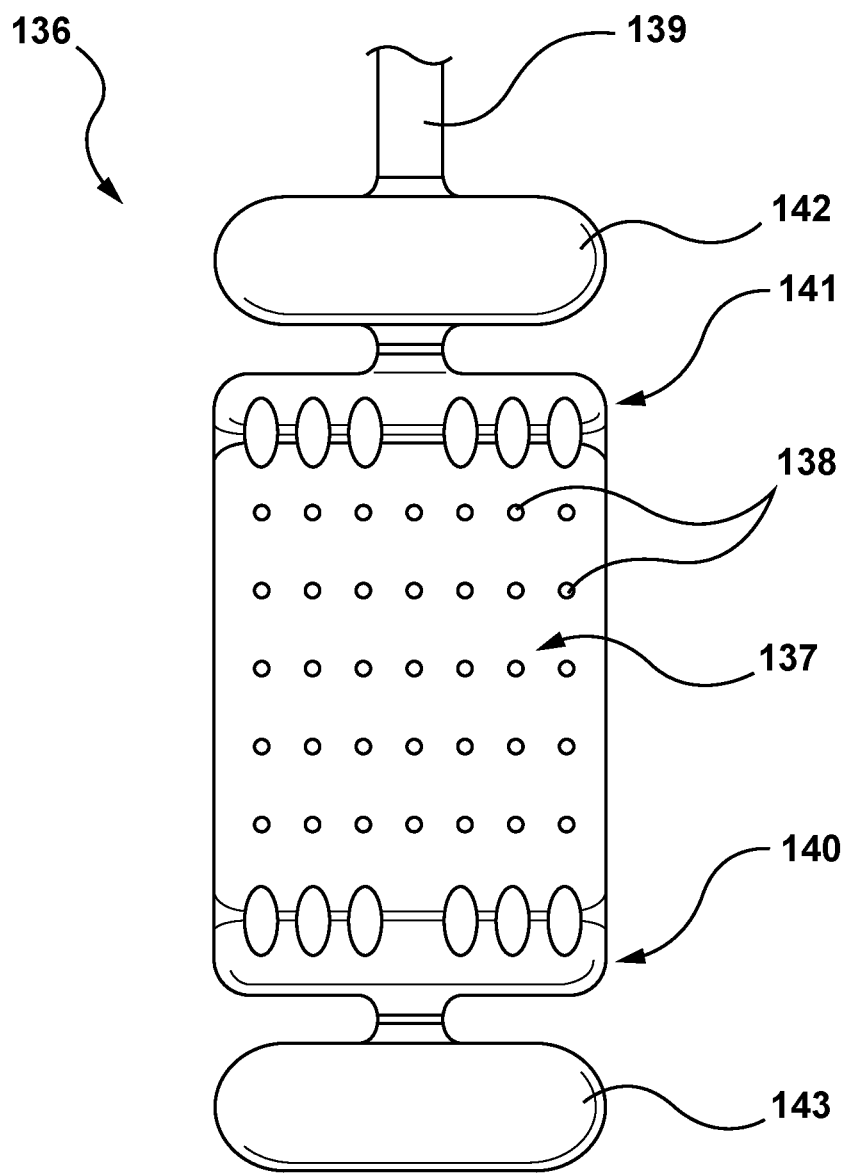
FIG. 51 is an illustration of an irrigation heat exchanger.
Figure 52:
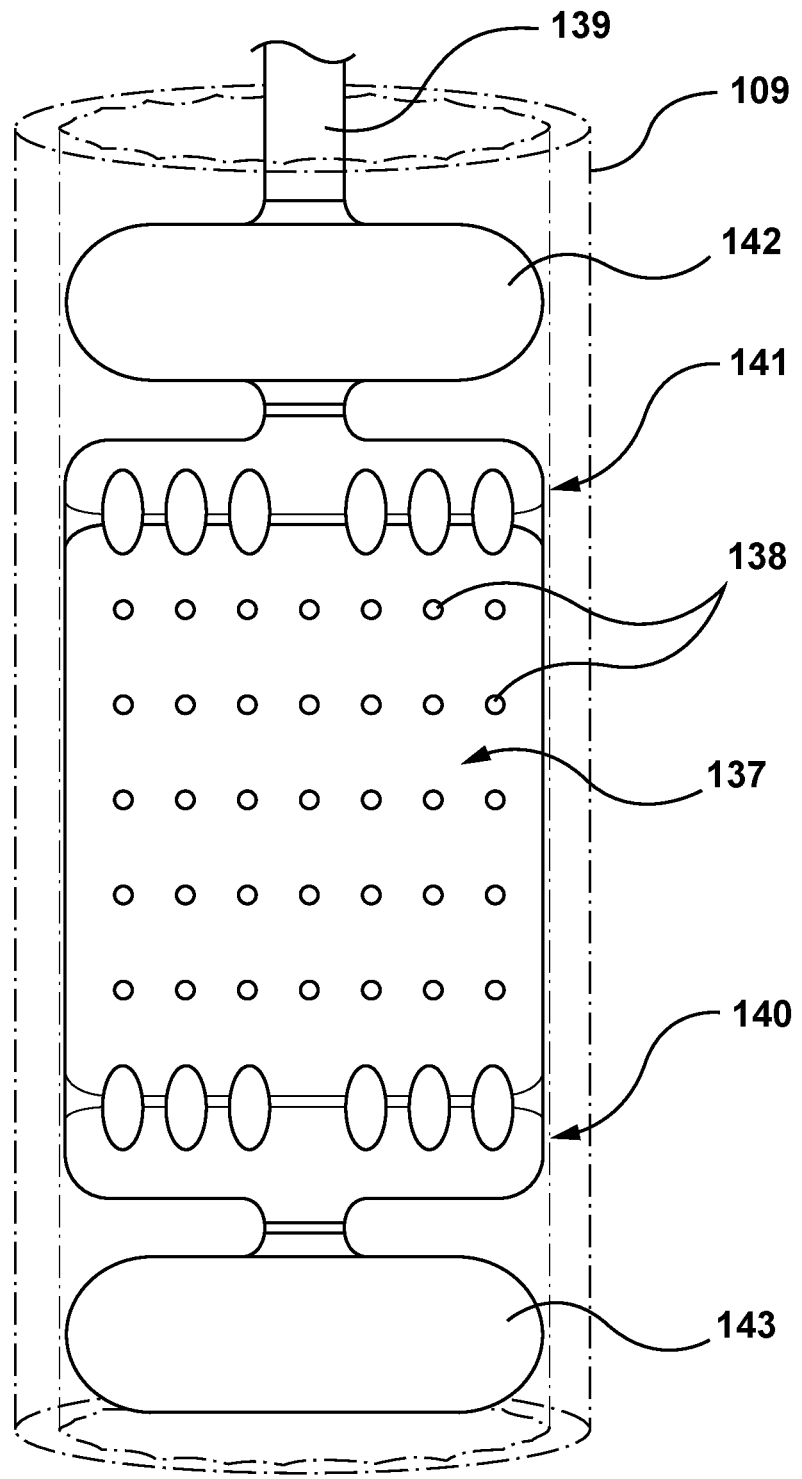
FIG. 52 is an illustration of the embodiment of FIG. 51 disposed in a body lumen.
Figure 53:
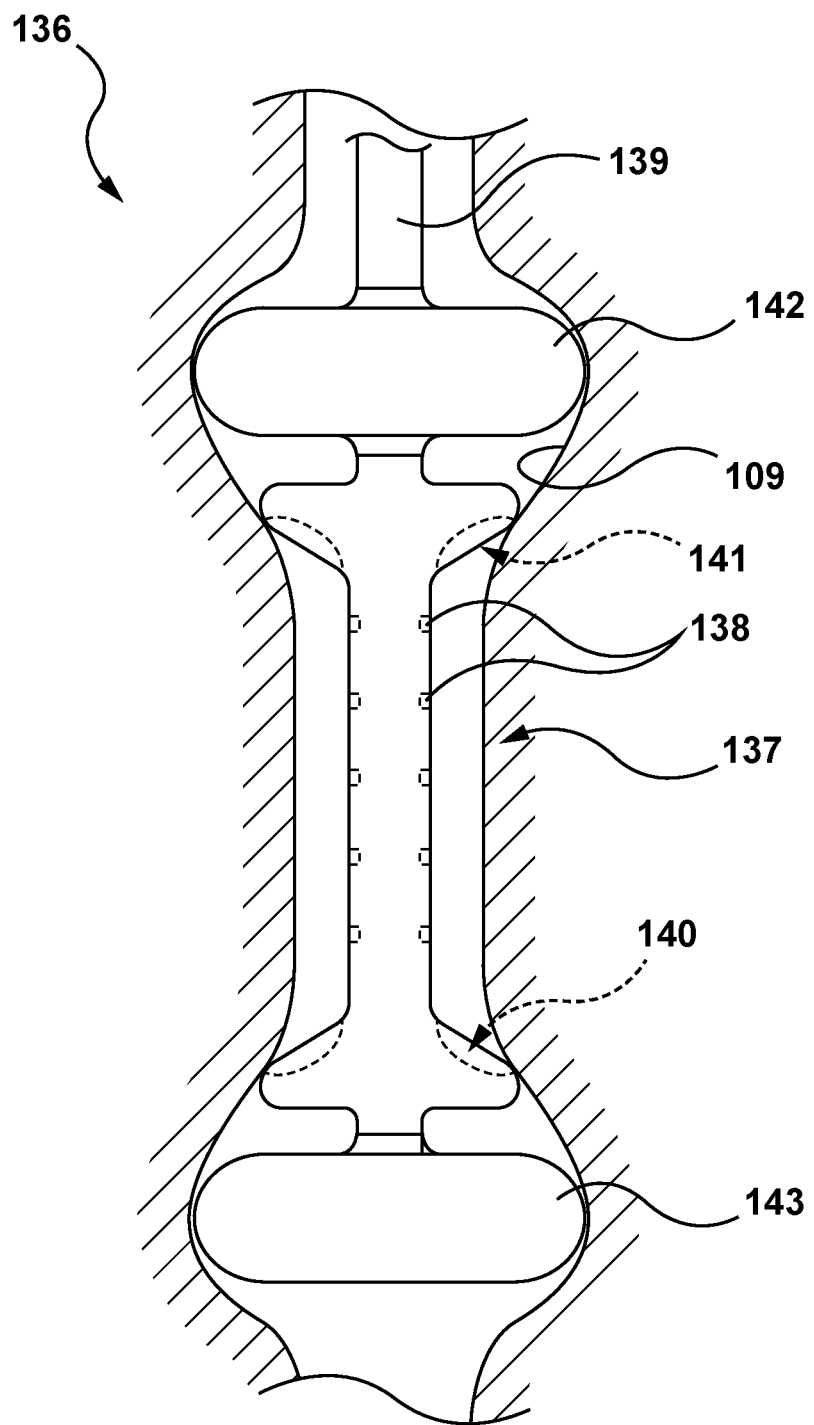
FIG. 53 is a side view of the embodiment depicted in FIG. 52.

A further alternative embodiment is depicted in FIGS. 51-53. Similar to the embodiment depicted in FIG. 25, heat exchange fluid 125 is delivered directly to the desired treatment zone. The irrigation heat exchanger 136 delivers heat exchange fluid through an irrigation surface 137 with a series of irrigation ports 138 from which heat exchange fluid is sprayed. The heat exchanger 136 may further comprise a proximal blocking balloon 142 and a distal blocking balloon 143 which prevents fluid from escaping into the stomach or the larynx respectively. The heat exchanger 136 may further comprise a distal suction component 140 and a proximal suction 141 component which captures fluid after it has been sprayed from the irrigation ports 138. The heat exchanger 136 may be connected to or integral with a tube 139. Tube 139 may comprise an inlet tube and outlet tube (not depicted) for supplying fluid to and removing fluid from the desired treatment zone. The other end of tube 139 may be connected with an external controller that provides heat exchange fluid 125.

Option 3 for Exchanging Heat: Using a Thermoelectric Heat Exchange Device

In some embodiments, the heat exchanger is a Peltier device which may heat or cool the esophagus with thermoelectric heat exchange. The heat exchange device is connected to an external controller that powers the Peltier device.

Option 4 for Exchanging Heat: Using an Evaporative Cooling Device

An alternate method of cooling the esophagus is to deliver a coolant directly to the endoluminal surface of the esophagus. In one embodiment, the heat exchange device is connected to an external controller that provides the coolant. The coolant is sprayed in a mist mixed with a gas such as air or oxygen to the surface of the esophagus. The coolant rapidly evaporates due to the gas flow. The esophageal surface is cooled as a result of the evaporation.

Option 5 for Exchanging Heat: Using a Vortex Tube Heat Exchange

Some embodiments of the heat exchanger make use of a vortex tube, a mechanical device that separates a compressed gas into a hot stream and a cold stream. Either stream could be used for heat exchange, so this type of heat exchanger could be used to either warm or cool the esophagus.

Option 6 for Exchanging Heat: Endothermic/Exothermic Chemical Reaction.

Step 5: Confirming that the Target Site is Protected

Once the heat exchanger is positioned at the target site and adequate heat exchange is occurring between the esophagus and the heat exchanger, the user confirms that the tissue is protected.

There are a number of options to make this confirmation:

(a) Imaging modalities such as MRI or ultrasound may be used to monitor tissue changes in the esophagus. An absence of lesion growth or tissue changes supports the lack of tissue damage.

(b) Monitoring a physiological parameter indicative of tissue viability/health. Examples of physiological parameters may include temperature, tissue impedance, blood perfusion rate, oxygen saturation, or nerve function (for example vagus or phrenic nerve). Some embodiments of the heat exchange device comprise a means to measure these parameters. The heat exchange device may be connected to an external controller that interprets/displays/analyses the signals produced from the heat exchange device. The measured physiological parameters may be used in a control loop to alert the user of unsafe levels. The control loop may be connected to the ablation therapy device to stop ablation before a critical level is reached. The control loop may include a mathematical model of changes in the physiological parameter that can predict when irreversible damage may occur, and stop the ablation energy before the dangerous levels are reached.

There are a number of options for measuring temperature. The temperature measured may be one of a number of temperatures, including the temperature of the desired treatment area, or the patient's core body temperature. Temperature may be measured by any of a number of sensors, including thermocouples, thermistors, fiber optics, or by another method such as ultrasound, MRI, infrared, or microwave radiometry.

In one embodiment, the means of measuring temperature is affixed to the heat exchange surface. For example, individual thermocouple pairs, or a flexible circuit containing thermocouples and/or thermistors, or a fiber optic cable may be affixed to the surface of the heat exchanger with adhesives. Alternately, the temperature sensors may be spray or dip coated onto the surface of the heat exchanger with a flexible material such as urethane. Alternately, the temperature sensors may be laminated onto the surface of the heat exchange surface with a thin film, or they may be laminated between two thin film layers, which may then be used to create the heat exchanger. Alternately, the temperature sensors may be positioned inside pockets welded to the surface of the heat exchanger. When positioned on the surface of the heat exchanger, the temperature sensors measure the temperature of the desired treatment area once the heat exchanger makes contact with the desired treatment area (e.g. FIG. 18. Temperature sensors 104 affixed to balloon surface of balloon heat exchanger 101).

In another embodiment, the temperature sensors are drawn onto the surface of the balloon with conductive ink. For example, the temperature sensors of some embodiments are thermocouples made by crossing a line of conductive silver ink with a line of conductive nickel ink.

In another embodiment, the temperature sensors are affixed to the shaft with adhesives, thermal welding, or another means. For example, a temperature sensor may be added to the distal end of the shaft, which is positioned in the patient's stomach to monitor core body temperature.

In another embodiment, the temperature sensors 104 are mounted on a frame 117 that is separate from the heat exchanger. For example, the frame 117 may be made of expandable and collapsible struts that can be deployed around the heat exchanger to measure the temperature of the desired treatment area (e.g. FIG. 19 temperature sensors mounted on frame separate from heat exchanger). The struts may be in one of a number of configurations, such as linear (top of FIG. 19), helical (bottom of FIG. 19), intersecting, or asymmetrical. The struts may be expanded and collapsed with the use of a mechanical mechanism such as a pull wire. The struts may be made of a number of materials, for example, a flexible metal such as Nitinol, or a plastic such as Pebax, or a shape memory alloy or shape memory polymer. The shape memory polymer may be activated to take on the desired shape by thermal or electrical inputs.

In another embodiment, the struts may be part of the shaft. The embodiment of FIG. 20 includes temperature sensors 104 mounted on struts 118 made from main shaft 103.

Figure 36:
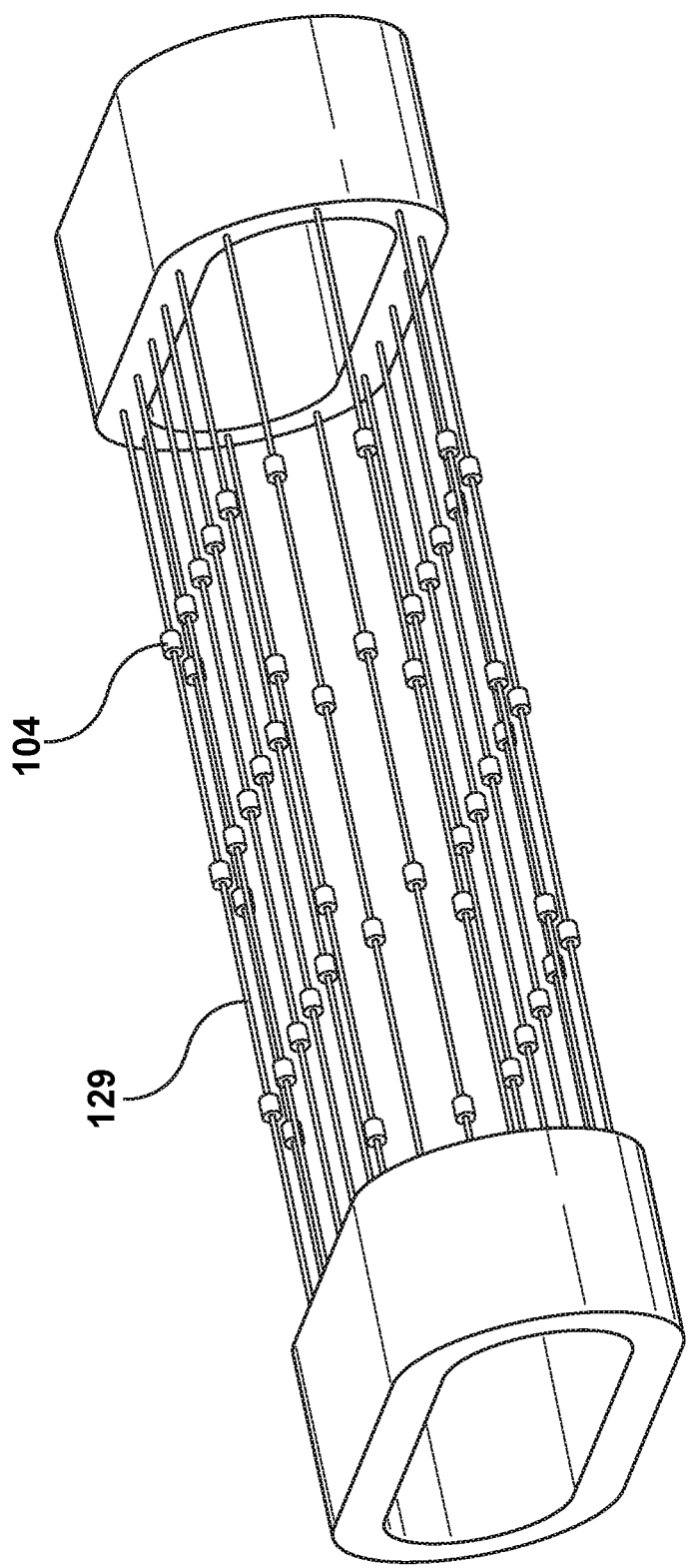
FIG. 36 is an illustration of temperature sensors mounted on the embodiment depicted in FIG. 32.
Figure 37:
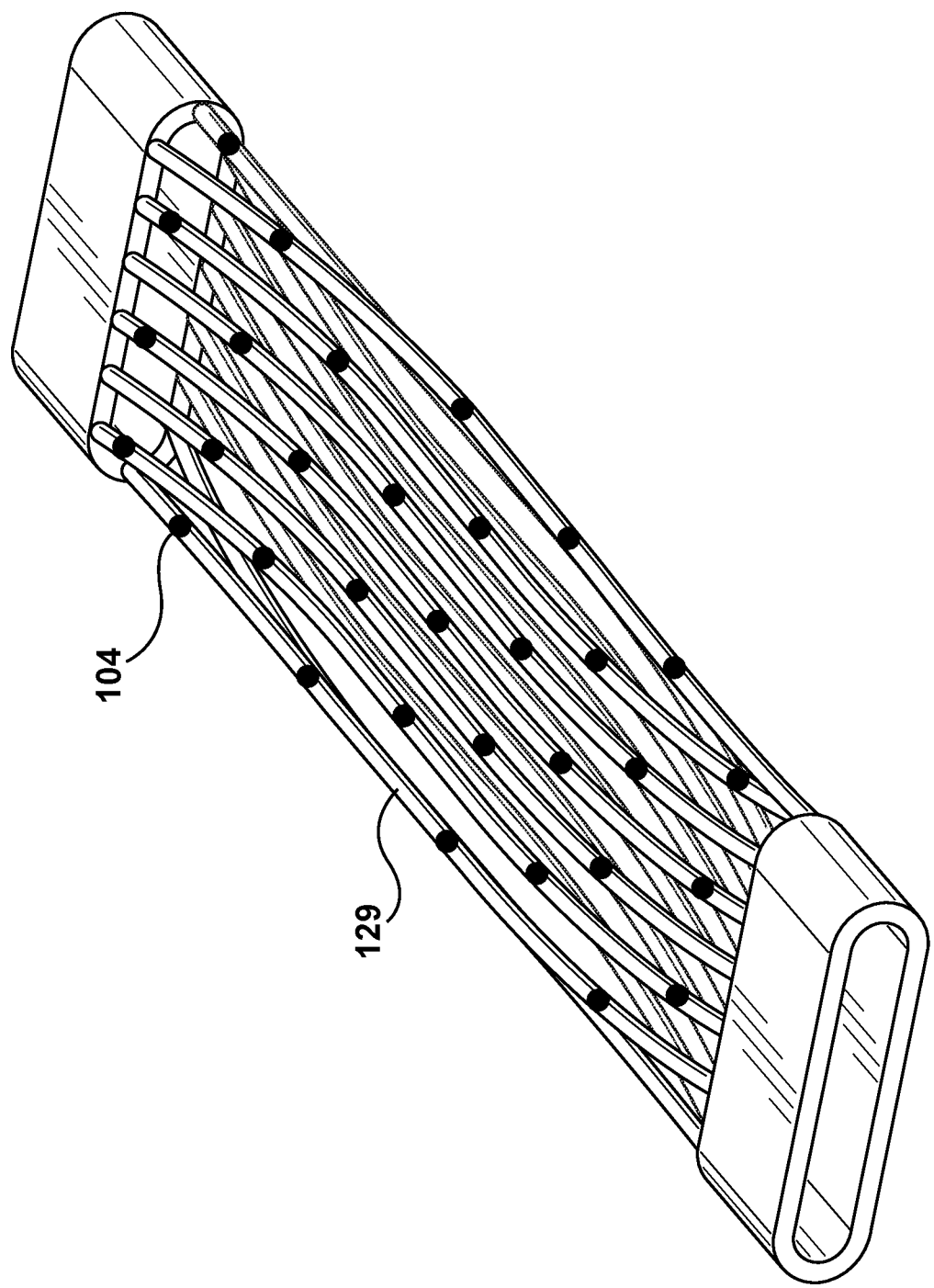
FIG. 37 is an illustration of temperature sensors mounted on the embodiment depicted in FIG. 33.

As previously mentioned, the balloon heat exchanger is more preferably oblong to better conform to the cross-sectional area of the collapsed esophagus and reduce the resulting displacement of the esophagus. Accordingly, the embodiments illustrated in FIGS. 19 and 20 may be provided with a more oblong cross-sectional shape. For example, FIGS. 36 and 37 illustrate further embodiments comprising tubes 129 and temperature sensors 104 which feature a more oblong cross-sectional profile.

Figure 21:
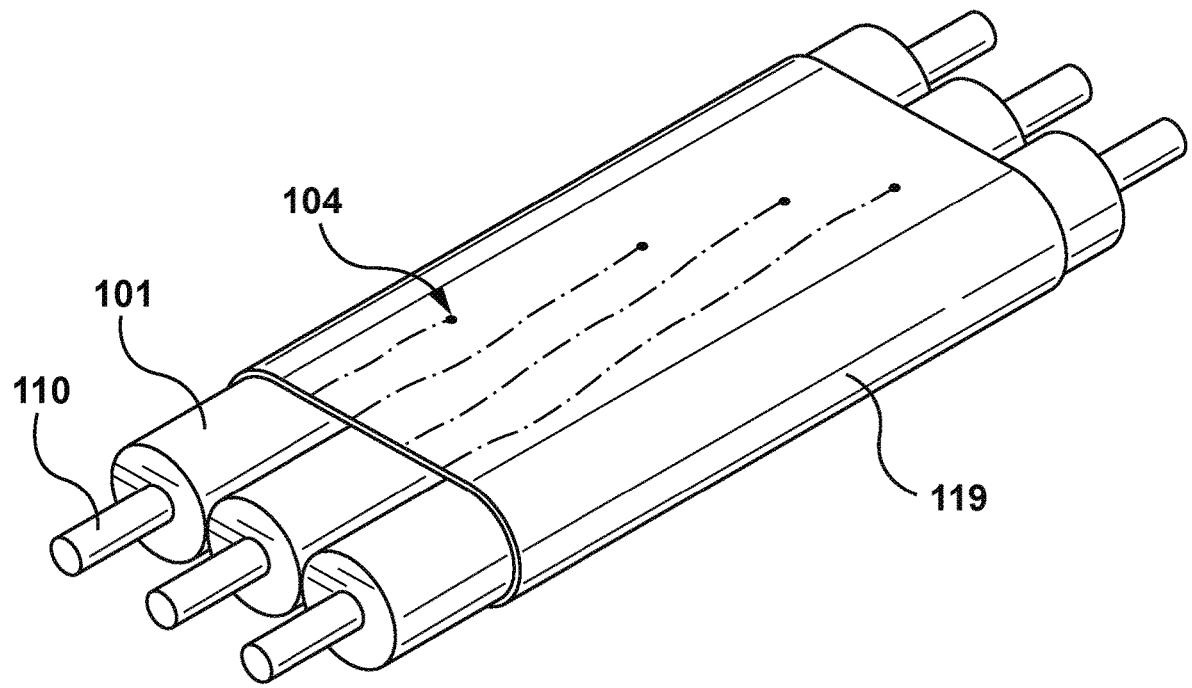
FIG. 21 is an illustration of temperature sensors affixed to textile.
Figure 22:
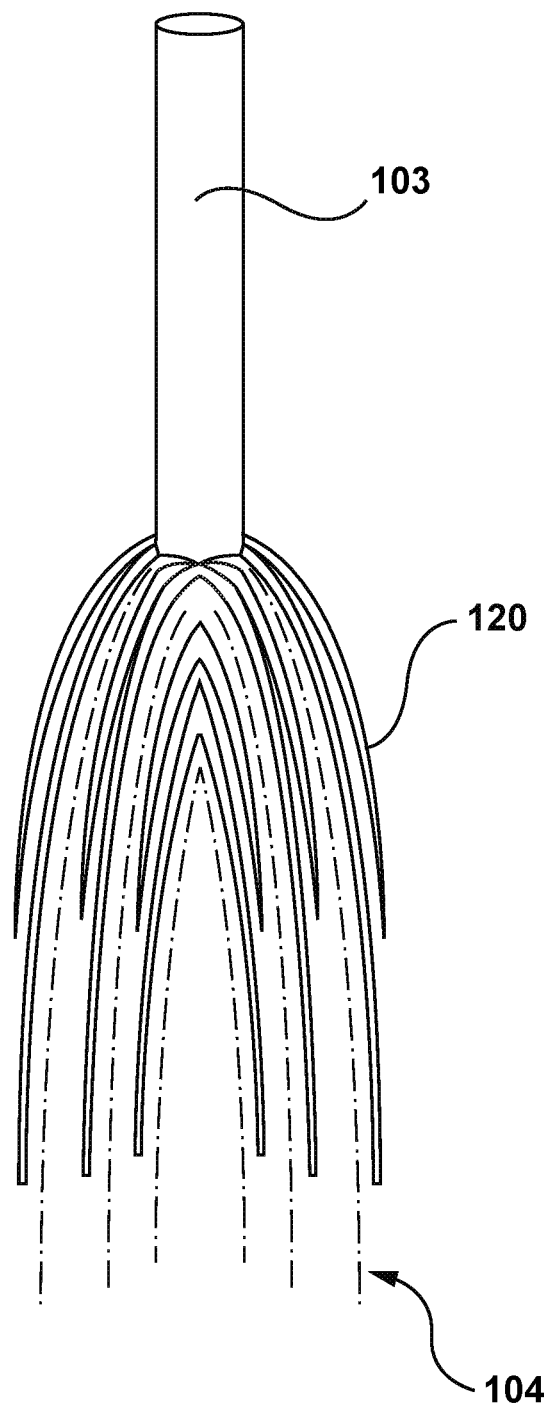
FIG. 22 is an illustration of temperature sensors affixed to strands.

In another embodiment, the temperature sensors 104 are affixed to or woven into a textile 119 (i.e. a fabric material) that surrounds the heat exchanger (e.g. FIG. 21 temperature sensors affixed to textile). When the heat exchanger is expanded into its desired shape, the fabric may expand around it, allowing the temperature sensors to make contact with and measure the temperature of the desired treatment area.

In another embodiment, the temperature sensors 104 are affixed to strands 120 connected at one end of the heat exchanger so that they hang freely about the other end of the heat exchanger. The example of FIG. 22 includes temperature sensors 104 affixed to strands 120 which are attached to main shaft 103. Strands 120 are flexible and atraumatic such that as they are advanced through the esophagus, the esophagus is not damaged.

In order to obtain meaningful temperature data, an array of temperature sensors may be used. The sensors may be positioned in such a way that an algorithm may be used to interpolate the temperatures between the sensors in order to produce a temperature map of the esophageal surface. Alternately, a temperature map may be produced using IR or microwave temperature measuring modalities.

One concern some users may have with respect to the sensors is what is known as the antenna effect. There is some published literature indicating that metal electrodes in the esophagus may promote thermal injury as a result of electrical or thermal interactions with the ablation catheter. To eliminate this risk, the electrodes on some embodiments of the heat exchange device are insulated, or made of a non-conductive material. Alternately, the electrodes may be positioned such that the electrical or thermal interactions will not affect them, for example, the electrodes may be located on the posterior wall of the heat exchanger so that the heat exchanger insulates the electrodes from the interactions. In addition, filters may be built into the external device where the signals are interpreted and displayed to eliminate these interactions.

Step 6: Retrieving the Heat Exchange Device

After treatment, the heat exchanger is typically collapsed for removal from the patient. In one embodiment, the heat exchanger is evacuated by pulling a vacuum at the outlet port or the inlet port. Once evacuated, the heat exchanger can be pulled back through the delivery orifice and removed from the patient. In alternative embodiments, the heat exchanger is collapsed using a sleeve around the heat exchanger. This sleeve may comprise a fabric mesh structure, a metal structure, such as a structure similar to a stent, or a polymer cage. In some embodiments the sleeve is a sheath. In one embodiment, the sleeve is collapsed using a mechanical mechanism. In another embodiment, the sleeve is collapsed using shape memory material properties.

Once the heat exchanger is collapsed, the heat exchange device may be pulled into the delivery orifice, or the delivery orifice may be advanced over the heat exchange device. The heat exchange device may be inverted (inside-out) as it is pulled into the delivery orifice. In some embodiments of the method, the delivery orifice is the patient's nose or mouth. In another embodiment, the delivery orifice is a sheath separate from the device. The sheath may have a telescoping feature. The sheath may be integrated with the heat exchange device. For example, it may comprise expanding and contracting struts that are part of the body of the heat exchange device, or it may be a translating portion of the heat exchange device body.

Once inside the delivery orifice, the heat exchange device is removed from the patient.

Patient's Body Core Temperature

The user may be concerned about affecting the patient's core body temperature as a result of exchanging heat in the esophagus. There are a number of optional features and surgical techniques to mitigate this risk.

(a) Focus heat exchange at areas of highest risk. This may be achieved by monitoring a physiological parameter at different locations on the esophagus and using a control loop in the external controller to determine the high-risk areas and focus heat exchange in those areas.

(b) Counteract heat exchange at esophagus with opposite and optionally equal heat exchange at another body location. This may be achieved by measuring the amount of heat exchanged by the heat exchange device in the esophagus and using a separate device (such as a warming or cooling blanket) to exchange an equal and opposite amount of heat at a location distinct from the esophagus. A control loop may be used to automatically balance the heat exchanged. Alternatively, the heat exchange device may be used to supply opposite and optionally equal heat exchange while the ablation therapy is not being applied.

(c) Only exchange heat at the esophagus while an ablation is being performed. This may be achieved by a communication link between the ablation therapy device and the heat exchange device. The heat exchange device is activated only when the ablation therapy is applied.

Figure 23:
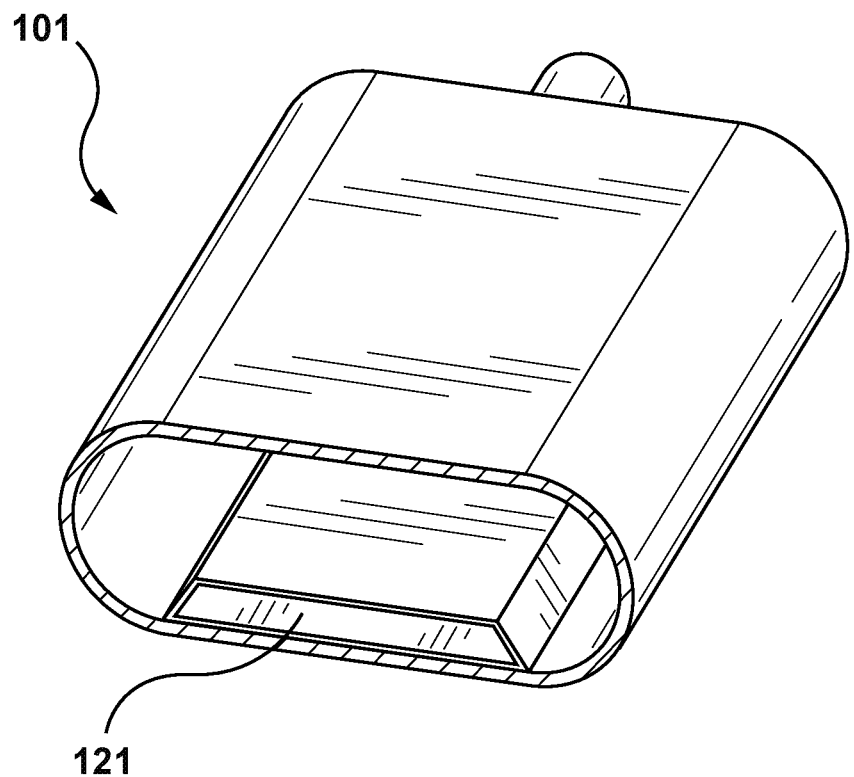
FIG. 23 is an illustration of a heat exchanger with an insulating air balloon inside.
Figure 24:
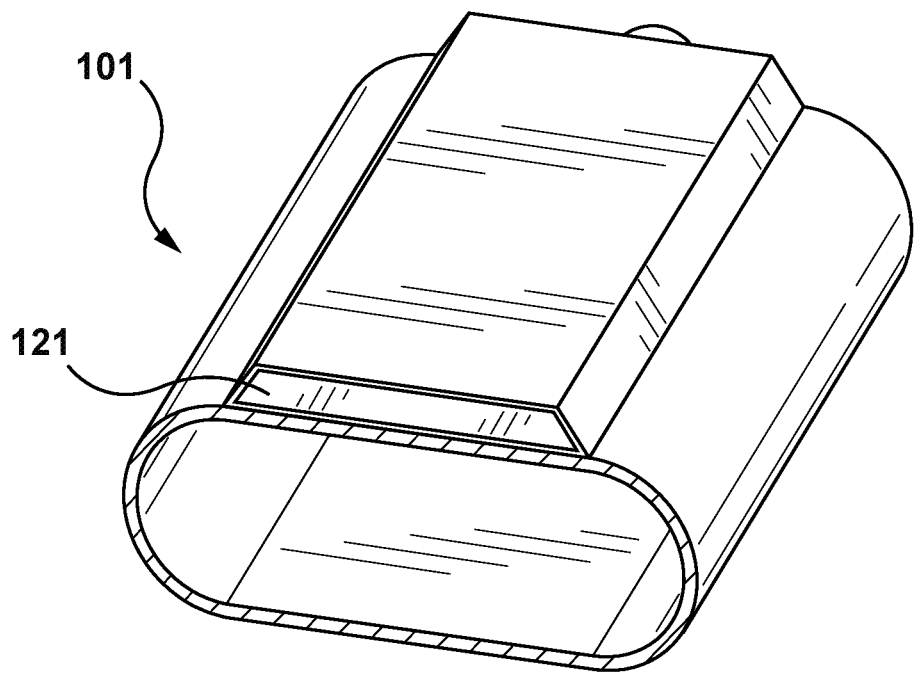
FIG. 24 is an illustration of a heat exchanger with an insulating air balloon outside.
Figure 34:
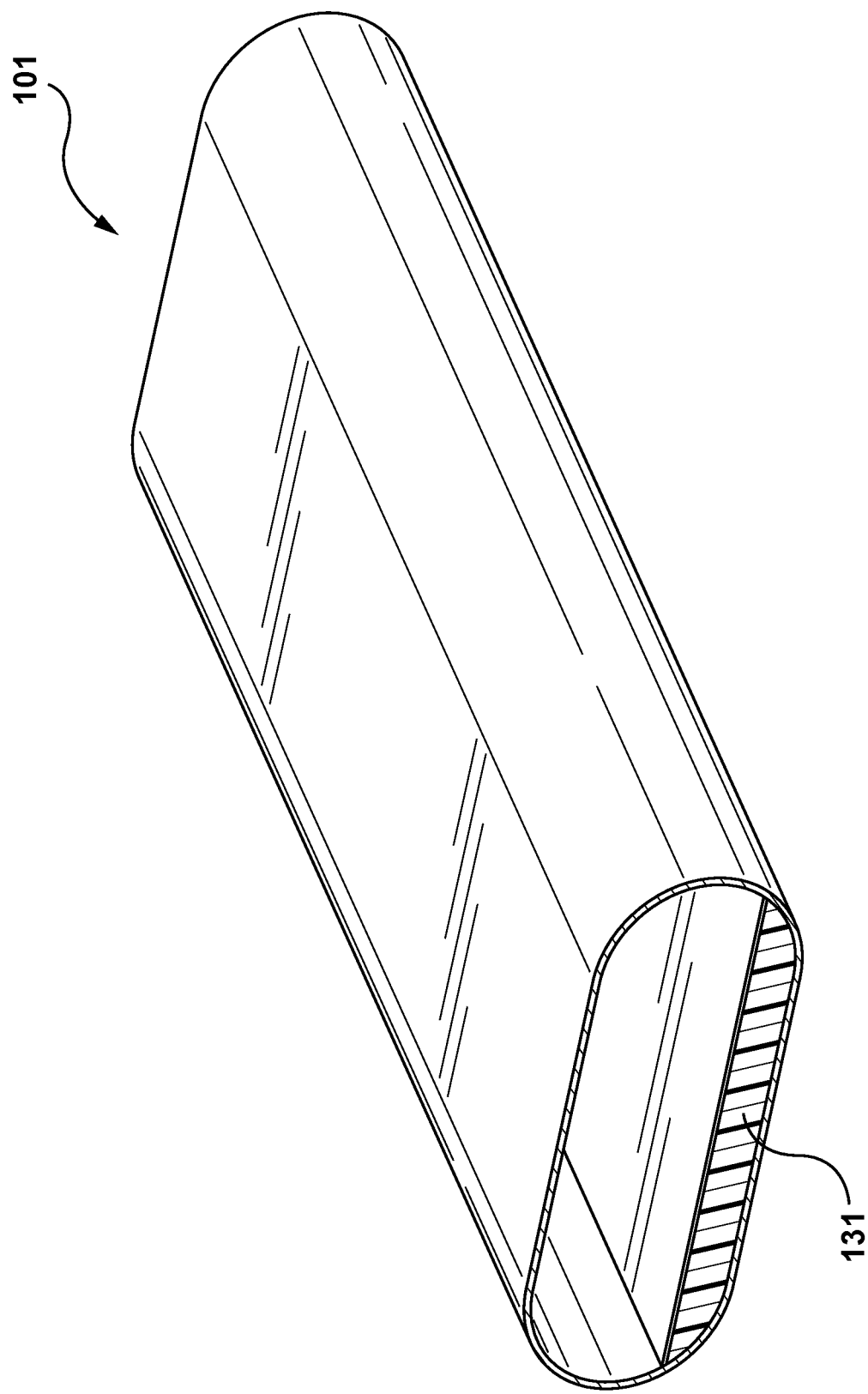
FIG. 34 is an illustration of a heat exchanger with an insulating portion.

(d) Some embodiments of the device may comprise the following insulative features at the non-therapy areas to minimize overall heat exchange and focus heat exchange only in the target area:
  (i) a coating of insulative material,
  (ii) an insulating lubricant or gel,
  (iii) an air filled lumen or space, or
  (iv) an air filled balloon inside (or outside) of the heat exchanger. FIG. 23 illustrates a balloon heat exchanger 101 with an insulating balloon 121 on the inside. FIGS. 24 and 34 illustrates a balloon heat exchanger 101 with an insulating balloon 121 on the outside.

In an ablation procedure, the "non-therapy area" is the side of the esophagus farthest away from the heart. By insulating the side of the esophagus farthest away from the heart, the heat exchange directed away from the "non-therapy area" and focused on the target area, which is the side of the esophagus closest to the heart. FIG. 34 illustrates another embodiment of a heat exchanger 101 which comprises an insulating portion 131. The insulating portion 131 may comprise one or more of an insulating lubricant or gel, a coating of insulating material, or air.

(e) Monitoring core body temperature. The heat exchange device may have a temperature sensor at a location away from the heat exchange area to monitor core body temperature. For example, in some embodiments the temperature sensor is at the distal end of the device and is positioned in the patient's stomach. A control loop may be used to feedback the patient's core temperature to the user and alert the user of dangerous temperatures. Alternately, the control loop could be used to control the amount of heat being exchanged in the patient.

(f) Determining a safe heat exchange operating range based on patient characteristics, the bio-heat equation, and other pertinent information. Some embodiments of the method include monitoring the amount of heat exchanged by the heat exchange device and confirming that it does not exceed the calculated safe amount.

These techniques can be performed during step 4 (FIG. 26) of the above described method.

Ablation Therapy

It is also important that an ablation therapy is not adversely affected by the heat exchange at the esophagus. To eliminate this risk, the user may monitor lesion growth or a physiological parameter at the therapy site using methodologies described above. A feedback loop may also be used to maximize the therapeutic energy delivered while the esophagus is not in danger. This may be achieved by monitoring a physiological parameter indicative of tissue heath/viability as described above, and using that data in a control loop to stop or decrease ablative therapy when the esophageal tissue is in danger, and increase/optimize ablative therapy when the esophageal tissue is not affected. The data may also be used to focus the heat exchange at high risk areas in the esophagus to minimize the impact on the therapeutic energy delivery. The data may also be used to decrease or stop the heat exchange during ablations when the esophagus is not at risk. These techniques can be performed during step 4 (FIG. 26) of the above described method.

Other Steps

Other additional steps in the method may include pacing the heart and performing a cardiac EP exam using the heat exchange device. To facilitate these steps, some embodiments of the heat exchange device comprise pacing and ECG electrodes on the body of heat exchange device. This technique can be performed during step 3 (FIG. 26) of the above described method.

Injury to an esophagus caused by heat or cold being delivered to the left atrium is prevented by regulating the temperature of the esophagus using embodiments of a heat exchange device having a heating/cooling balloon (or sac) which has an inflated cross section corresponding with the collapsed/relaxed/natural cross section of the inside of the esophagus whereby inflation of the balloon maintains the esophagus in its natural shape and location and avoids not displacing the esophagus towards the left atrium. Some alternative embodiments includes altering a configuration of the balloon to conform to or correspond with the cross section of an esophagus by means other than inflation.

The embodiments of the invention described above are intended to be exemplary only. The scope of the invention is therefore intended to be limited solely by the scope of the appended claims.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

EXAMPLES

Example 1

A method of regulating a temperature of an esophagus when heat or cold is delivered to a left atrium comprises altering a heat exchange device from an insertable configuration to a heat exchanging configuration which substantially conforms and corresponds with a cross-section of an inside of the esophagus such that the esophagus is substantially maintained in its natural shape and location whereby the esophagus is substantially not displaced towards the left atrium.

Example 2

A method of regulating a temperature of an esophagus when heat or cold is delivered to a left atrium comprises (a) inflating a heat exchange device from an collapsed configuration to an inflated configuration which substantially conforms and corresponds with a cross-section of an inside of the esophagus such that the esophagus is substantially maintained in its natural shape and location whereby the esophagus is substantially not displaced towards the left atrium and (b) regulating the temperature of the esophagus using the heat exchange device.

Example 3

A method of regulating a temperature of an esophagus when heat or cold is delivered to a left atrium includes the steps of:
(1) measuring the esophagus and selecting a size a heat exchange device which fits the esophagus;
(2) delivering the heat exchange device to a target site;
(3) confirming a desired location of the heat exchange device;
(4) exchanging heat with the esophagus;
(5) confirming that the target site is protected; and
(6) retrieving the heat exchange device.

Example 4

The method of example 3, wherein step (1) comprises using imaging such as fluoroscopy, CT, MRI, or EAM.

Example 5

The method of example 3, wherein the heat exchange device comprises a balloon and a main shaft, and the method includes, before step (2), the step of deflating or collapsing the balloon and wrapping or folding the balloon around the main shaft.

Example 6

The method of example 3, wherein the heat exchange device comprises a balloon, and the method includes, before step (2), the step of priming the heat exchange device to replace air with fluid.

Example 7

The method of example 3, wherein step (2) comprises advancing the heat exchange device through a nostril.

Example 8

The method of example 3, wherein the heat exchange device further comprises imaging markers and step (2) includes using an imaging system to position the heat exchange device.

Example 9

The method of example 3, wherein step (2) comprises advancing an outer sheath with the heat exchange device and pulling back on the outer sheath when the heat exchange device is positioned to expose the heat exchange device.

Example 10

The method of example 3, wherein step (3) comprises confirming an orientation of the heat exchange device relative to a known anatomical marker by imaging of imaging markers on the heat exchange device.

Example 11

The method of example 10, wherein the known anatomical marker is the left atrium.

Example 12

The method of example 3, wherein step (4) includes begin circulating a heat exchange fluid through the heat exchange device before heat or cold is delivered to the left atrium.

Example 13

The method of example 12, wherein step (4) includes stop circulating the heat exchange fluid through the heat exchange device after heat or cold is delivered to the left atrium.

Example 14

The method of example 3, wherein step (5) comprises imaging of a tissue of the esophagus to determine if the tissue has been changed.

Example 15

The method of example 3, wherein step (5) comprises monitoring a physiological parameter which indicates a health factor of a tissue of the esophagus.

Example 16

The method of example 13, wherein prior to step (6), the method includes vacuuming the heat exchange fluid from the heat exchange device.

Example 17

The method of example 9, wherein prior to step (6), the method includes advancing the outer sheath to cover the heat exchange device, thereby reducing a diameter of the heat exchange device.

Example 18

The method of example 3, wherein step (6) includes removing the heat exchange device from a patient.

Example 19

A method of monitoring a temperature of a tissue of an esophagus includes (a) inflating a device from an collapsed configuration to an inflated configuration which conforms and corresponds with a cross-section of an inside of the esophagus such that the esophagus is maintained in its natural shape and location whereby the esophagus is not displaced towards a left atrium and (b) monitoring the temperature of the tissue using sensors on an outside of the device.

Example 20

The method of example 19, wherein step (b) comprises using sensors on one side of the device.

We claim:

1. A heat exchanging device for regulating a temperature of an esophagus when heat or cold is delivered to a left atrium of a heart, comprising:
   an elongated shaft comprising a distal end and a proximal end, the elongated shaft defining at least a first lumen and a second lumen;
   a handle attached to the proximal end of the elongated shaft;
   a heat exchanger attached to the distal end of the elongated shaft, the heat exchanger comprising a distal end, a proximal end, and a cavity therebetween, at least a portion of said cavity being in fluid communication with the first lumen and the second lumen of the elongated shaft, the heat exchanger comprising an insertable configuration and a heat exchanging configuration,
   wherein a cross-section of the heat exchanger in the insertable configuration is smaller than a cross-section of the heat exchanger in the heat exchanging configuration, and
   wherein said heat exchanger comprises a balloon which is expandable, wherein said balloon is constrained by a plurality of welds attaching an anterior surface and a posterior surface of the balloon and forming a plurality of flow channels through the balloon, the balloon being constrained in an axis of the cross-section such that when said balloon is expanded to the heat exchanging configuration the cross-sectional shape of the heat exchanger is substantially oblong in a direction transverse to the longitudinal axis of the balloon and said cross-section of the heat exchanger in the heat exchanging configuration substantially conforms to and corresponds with a cross-section of an inside surface of the esophagus such that the esophagus is substantially maintained in its natural shape and location when the heat exchanger is in its heat exchanging configuration, the plurality of channels oriented as a series along the longitudinal axis of the balloon such that the heat exchange fluid flowing through the heat exchanger is channeled to a pair of side edges of the heat exchanger.

2. The heat exchanging device of claim 1, wherein the plurality of welds are oriented as a series of consecutive chevrons along the length of the heat exchanger.

3. The heat exchanging device of claim 1, wherein the first lumen comprises a fluid inflow port to allow heat exchange fluid to flow into said heat exchanger.

4. The heat exchanging device of claim 3, wherein the fluid inflow port is proximate a distal end of said heat exchanger.

5. The heat exchanging device of claim 1, wherein the second lumen comprises a fluid outflow port to allow heat exchange fluid to flow out of said heat exchanger.

6. The heat exchanging device of claim 5, wherein the fluid outflow port is proximate a proximal end of said heat exchanger.

7. The heat exchanging device of claim 1, wherein the anterior surface is positioned proximate an anterior wall of the esophagus and the posterior surface is positioned proximate a posterior wall of the esophagus, and wherein the posterior wall comprises a heat insulating layer for insulating the posterior wall of the esophagus from heat exchange fluid circulating through the heat exchanger.

8. The heat exchanging device of claim 1, wherein the heat exchanger further comprises temperature sensors for measuring the temperature of a target site within the esophagus.

9. The heat exchanging device of claim 1 further comprising at least two radiopaque markers, one of said at least two radiopaque markers being positioned adjacent the proximal end of the heat exchanger, and one of said at least two radiopaque markers being positioned adjacent the distal end of the heat exchanger.

10. The heat exchanging device of claim 1 further comprising force sensors attached to the heat exchanger for determining the amount of force being applied by the heat exchanger to the esophagus.

11. The heat exchanging device of claim 1 further comprising at least two electroanatomic mapping electrodes for determining the position of the heat exchanger relative to a target therapy site, one of said at least two electrodes being positioned adjacent the proximal end of the heat exchanger, and one of said at least two electroanatomic mapping electrodes being positioned adjacent the distal end of the heat exchanger.

12. The heat exchanging device of claim 1 further comprising at least one pacing electrode for delivering a pacing signal to the heart.

13. The heat exchanging device of claim 1 further comprising at least one electrocardiogram electrode for detecting electrocardiogram signals.

14. The heat exchanging device of claim 1 further comprising an outer sheath, wherein the outer sheath is movable between a first position and a second position, wherein when the outer sheath is in the first position, the heat exchanger is within the outer sheath, and when the outer sheath is in the second position, the heat exchanger is exposed.

15. The heat exchanging device of claim 1 further comprising an outer balloon surrounding the heat exchanger.

16. The heat exchanging device of claim 1, wherein the handle further comprises:
- a fluid inflow connector in fluid communication with the first lumen for connection with a heat exchange fluid source; and
- a fluid outflow connector in fluid communication with the second lumen for connection with a heat exchange fluid return repository.

17. The heat exchanging device of claim 16, wherein heat exchange fluid is circulated in a closed loop.

18. The heat exchanging device of claim 1, wherein the plurality of welds have curved ends that correspond with an outer contour of the balloon.

\* \* \* \* \*